United States Patent
Moe et al.

(10) Patent No.: US 10,576,137 B2
(45) Date of Patent: Mar. 3, 2020

(54) OLIGOSIALIC ACID DERIVATIVES, METHODS OF MANUFACTURE, AND IMMUNOLOGICAL USES

(71) Applicant: Children's Hospital & Research Center at Oakland, Oakland, CA (US)

(72) Inventors: Gregory R. Moe, Alameda, CA (US); Brent T. Hagen, Oakland, CA (US)

(73) Assignee: Children's Hospital Research Center at Oakland, Oakland, CA (US)

( * ) Notice: Subject to any disclaimer, the term of this patent is extended or adjusted under 35 U.S.C. 154(b) by 0 days.

(21) Appl. No.: 15/082,905

(22) Filed: Mar. 28, 2016

(65) Prior Publication Data

US 2017/0056489 A1   Mar. 2, 2017

Related U.S. Application Data

(63) Continuation of application No. 12/168,004, filed on Jul. 3, 2008, now Pat. No. 9,333,247.

(60) Provisional application No. 60/958,342, filed on Jul. 3, 2007.

(51) Int. Cl.

| | |
|---|---|
| *A61K 39/095* | (2006.01) |
| *A61K 47/64* | (2017.01) |
| *A61K 39/108* | (2006.01) |
| *A61K 31/715* | (2006.01) |
| *C07K 16/12* | (2006.01) |
| *A61K 39/00* | (2006.01) |
| *C08B 37/00* | (2006.01) |
| *C07H 1/00* | (2006.01) |
| *C07H 7/027* | (2006.01) |
| *C07H 13/04* | (2006.01) |

(52) U.S. Cl.
CPC ........ *A61K 39/0258* (2013.01); *A61K 39/095* (2013.01); *C07H 1/00* (2013.01); *C07H 7/027* (2013.01); *C07H 13/04* (2013.01); *C07K 16/1217* (2013.01); *C07K 16/1282* (2013.01); *C08B 37/0006* (2013.01); *A61K 2039/55505* (2013.01); *A61K 2039/55544* (2013.01); *A61K 2039/6037* (2013.01); *G01N 2333/22* (2013.01); *G01N 2333/245* (2013.01); *G01N 2400/02* (2013.01)

(58) Field of Classification Search
CPC ........ A61K 39/0011; A61K 2039/6037; A61K 39/0258; A61K 39/095; A61K 31/715; A61K 2039/6012; A61K 39/395; A61K 39/39558; A61K 39/40; A61K 39/44; A61K 47/6851; A61K 2039/55505; A61K 2039/55544; A61K 2039/585; A61K 31/7008; A61K 47/48569; A61K 2039/5152; A61K 2039/545; A61K 31/70; C07K 16/1217; C07K 16/3076; C07K 16/3084; C07K 19/00; C07K 2317/14; C07K 2317/20; C07K 2317/31; C07K 2317/33; C07K 2317/40; C07K 2317/56; C07K 2317/565; C07K 2317/622; C07K 2317/73; C07K 2319/00; C07K 16/1282; C08B 37/0063; C08B 37/0006; C08L 5/00; C07H 13/04; C07H 1/00; C07H 7/027; G01N 2333/22; G01N 2333/245; G01N 2400/02; G01N 33/57484; C12N 2500/34; C12N 5/0693; Y02A 50/474

See application file for complete search history.

(56) References Cited

U.S. PATENT DOCUMENTS

| | | | |
|---|---|---|---|
| 4,021,542 | A | 5/1977 | Schmidt et al. |
| 4,062,950 | A | 12/1977 | Frommer et al. |
| 4,175,123 | A | 11/1979 | Junge et al. |

(Continued)

FOREIGN PATENT DOCUMENTS

| | | |
|---|---|---|
| EP | 2173759 | 4/2010 |
| JP | 2009523736 | 6/2009 |

(Continued)

OTHER PUBLICATIONS

Angata, et al., "Chemical Diversity in the Sialic Acids and Related α-Keto Acids: An Evolutionary Perspective," 102 (2): 439-470 (2002).

(Continued)

*Primary Examiner* — Sarvamangala Devi
(74) *Attorney, Agent, or Firm* — Rudy J. Ng; Carol L. Francis; Bozicevic, Field & Francis LLP

(57) ABSTRACT

The invention relates to methods of producing, and compositions comprising, an isolated alpha (2→8) or (2→9) oligosialic acid derivative bearing a non-reducing end enriched for one or more de-N-acetyl residues and resistant to degradation by exoneuraminidase. A representative production method involves: (i) treating an alpha (2→8) or (2→9) oligosialic acid precursor having a reducing end and a non-reducing end with sodium borohydride under conditions for de-N-acetylating the non-reducing end; and (ii) isolating alpha (2→8) or (2→9) oligosialic acid derivative having one or more de-N-acetylated residues and a non-reducing end that is resistant to degradation by exoneuraminidase. Isolated alpha (2→8) or (2→9) oligosialic acid derivatives that comprise a non-reducing end de-N-acetyl residue are provided, as well as antibodies specific for the derivatives, compositions comprising the derivatives, kits, and methods of use including protection against and detection of *E. coli* K1 and *N. meningitidis* bacterial infection, and in diagnosing and treating cancer.

17 Claims, 21 Drawing Sheets

Figure 1:
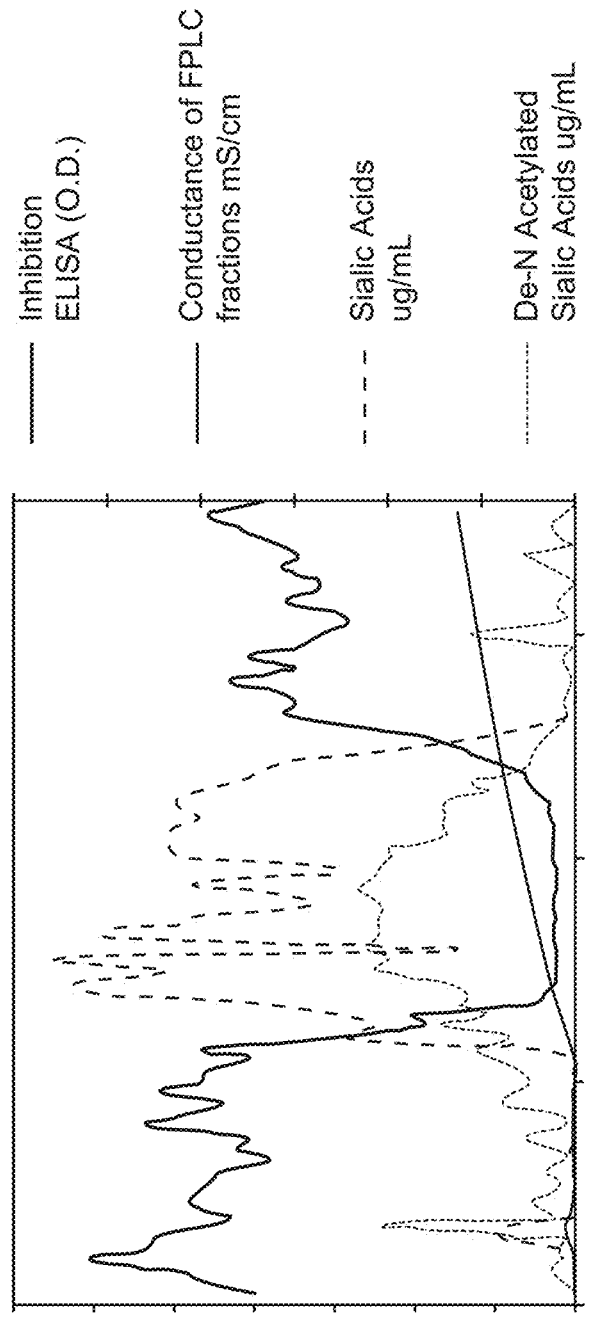

Specification includes a Sequence Listing.

(56) References Cited

U.S. PATENT DOCUMENTS

| | | |
|---|---|---|
| 4,216,208 A | 8/1980 | DeBarbieri |
| 4,254,256 A | 3/1981 | Otani et al. |
| 4,314,999 A | 2/1982 | DeBarbieri |
| 4,656,159 A | 4/1987 | Mcpherson et al. |
| 4,713,374 A | 12/1987 | Della Valle et al. |
| 4,797,477 A | 1/1989 | Yoshimura et al. |
| 4,803,303 A | 2/1989 | Horii et al. |
| 4,840,941 A | 6/1989 | Ueno et al. |
| 4,914,195 A | 4/1990 | Ogawa et al. |
| 4,968,786 A | 11/1990 | Ogawa et al. |
| 4,983,725 A | 1/1991 | Miyaji et al. |
| 5,231,177 A | 11/1993 | Saito et al. |
| 5,264,424 A | 11/1993 | Della Valle et al. |
| 5,243,035 A | 12/1993 | Nakabayashi et al. |
| 5,272,138 A | 12/1993 | Hakomori et al. |
| 5,332,756 A | 7/1994 | Mongelli et al. |
| 5,667,285 A | 9/1997 | Seetharaman et al. |
| 5,674,988 A | 10/1997 | Sabesan |
| 5,759,823 A | 6/1998 | Wong et al. |
| 5,962,434 A | 10/1999 | Schnaar et al. |
| 6,048,527 A | 4/2000 | Granoff et al. |
| 6,075,134 A | 6/2000 | Bertozzi et al. |
| 6,110,897 A | 8/2000 | Unverzagt et al. |
| 6,274,568 B1 | 8/2001 | Schnaar et al. |
| 6,407,072 B1 | 6/2002 | Valle et al. |
| 6,458,937 B1 | 10/2002 | Bertozzi et al. |
| 6,548,476 B1 | 4/2003 | Wu et al. |
| 6,680,054 B1 | 1/2004 | Reece et al. |
| 6,697,251 B1 | 2/2004 | Aisenberg |
| 6,936,701 B2 | 8/2005 | Bertozzi et al. |
| 7,070,801 B2 | 7/2006 | Yamazaki et al. |
| 8,642,562 B2 * | 2/2014 | Moe ............... A61K 31/7008 514/23 |
| 2004/0052805 A1 * | 3/2004 | Seid ............... A61K 39/095 424/184.1 |
| 2006/0035284 A1 | 2/2006 | Granoff et al. |
| 2006/0029621 A1 | 9/2006 | Granoff et al. |
| 2007/0010482 A1 | 1/2007 | Moe et al. |
| 2009/0010949 A1 | 1/2009 | Moe et al. |
| 2009/0012043 A1 | 1/2009 | Moe et al. |
| 2010/0068728 A1 | 3/2010 | Moe et al. |
| 2010/0260762 A1 | 10/2010 | Moe et al. |

FOREIGN PATENT DOCUMENTS

| | | |
|---|---|---|
| WO | 200109298 | 2/2001 |
| WO | 200209744 | 2/2002 |
| WO | 2006002402 | 1/2006 |
| WO | 2007075921 | 7/2007 |
| WO | 2009006620 | 1/2009 |
| WO | 2009047792 | 4/2009 |

OTHER PUBLICATIONS

Bardor, et al., "Mechanism of Uptake and Incorporation of the Non-human Sialic Acid N-Glycolylneuraminic Acid into Human Cells," Biol. Chem., 280(6): 4228-4237 (2005).
Chamas, et al., Cancer Res., 59: 1337-1346 (1999).
Collins, et al., "Conversion of cellular sialic acid expression from N-acetyl- to N-glycolylneuraminic acid using a synthetic precursor, N-glycolylmannosamine pentaacetate: inhibition of myelin-associated glycoprotein binding to neural cells" Glycobiology, 10(1): 11-20 (2000).
Dall'Olio, "Protein glycosylation in cancer neology:an overview," 49:M126-M135 (1996).
Djanashvili, et al., "Molecular Recognition of Sialic Acid End Groups by Phenylboronates" Chem. Eur. J., 11: 4010-4018 (2005).
Fondy, et al., "Haloacetamindo analogs of 2-amino-2-deoxy-D-mannose. Syntheses and effects on tumor-bearing mice.," J. Med. Chem., 24 (7): 848-852 (1981).
Hakomori "Tumor Malignancy Defined by Aberrant Glycosylation and Sphingo(glycol)lipid Metabolism" Cancer Research 56: 5309-5318 (1996).
Hanai, et al., "A novel Ganglioside, De-N-acetyl-GM3 (II 3 NeuNH2LacCer), Acting as Strong Promoter for Epidermal Growth Factor Receptor Kinase and as stimulator for Cell Growth," J. Biol. Chem. 263(13): 6296-6301 (1988).
Jennings, et al., "Determinant Specificities of the Group B and C Polycaccharides of Neisseria Meningitidis," J. Immunology, 134 (4): 2651-2657 (1985).
Kayser, et al., "Biosynthesis of a Nonphysiological Sialic Acid in Different Rat Organs, Using N-Propanoyl-D-hexosamines as Precursors," J. Biol. Chem., 267(24): 16934-16938 (1992).
Keppler, et al., "Biochemical engineering of the N-acyl side chain of sialic acid: biological implications," Glycobiology,11(2): 11R-18R (2001).
Kim and Varki "Perspectives on the significance of altered glycosylation of glycoproteins in cancer," Glycoconjugate Journal, 14: 596-576 (1997).
Luchansky, et al., "Cell Surface Labeling with Azides,"Meth Enzymol. 326: 249-272 (2003).
Manzi, et al., "Biosynthesis and Turnover of O-Acetyl and N-Acetyl Groups in the Gangliosides of Human Melanoma Cells," J. Biol. Chem,. 265(22) 13091-13103 (1990).
Moe, et al. "Epitopes Recognized by a Nonautoreactive Murine Anti-N-Propionyl Meningococcal Group B Polysaccharide Monoclonal Antibody," 73(4): 2123-2128 (2005).
Oetke, et al., "Evidence for efficient uptake and incorporation of sialic acid by eukaryotic cells," Eur. J. Biochem., 268:4553-4561 (2001).
Popa, et al. "Purification and structural characterization of de-N-acetylated form of GD3 ganglioside present in human melanoma tumors," Glycobiology, 17(4): 367-373 (2007).
Shimamura, et al., "Reductive Cleavage of Xaa-Proline Peptide Bonds by Mild Alkaline Borohydride Treatment Employed to Release O-Glycosidically Linked Carbohydrate Units of Glycoproteins," Arch. Biochem and Biophy., 232 (2): 699-706 (1984).
Sjoberg, et al., "Expression of De-N-acetyl-gangliosides in Human Melanoma Cells is Induced by Genistein or Nocodazole," J. Biol. Chem, 270(7): 2921-2930 (1995).
Granoff, et al., "Bactericidal Monoclonal Antibodies That Define Unique Meningococcal B Polysaccharide Epitopes That Do Not Cross-React with Human Polysialic Acid," J. Immunology, 160: 5028-5036 (1998).
Guo, et al., In: Meningococcal vaccines: Methods and Proticols. Pollard AJ (Ed). Humana Press, Inc. Totowa, N.J., 55-60 (2001).
Ashwell, et al., "α2-8 Sialic Acid Polymers: Size, Structure, and Compositional Analysis" Analytical Biochemistry, 222(2):495-502 (1994).

* cited by examiner

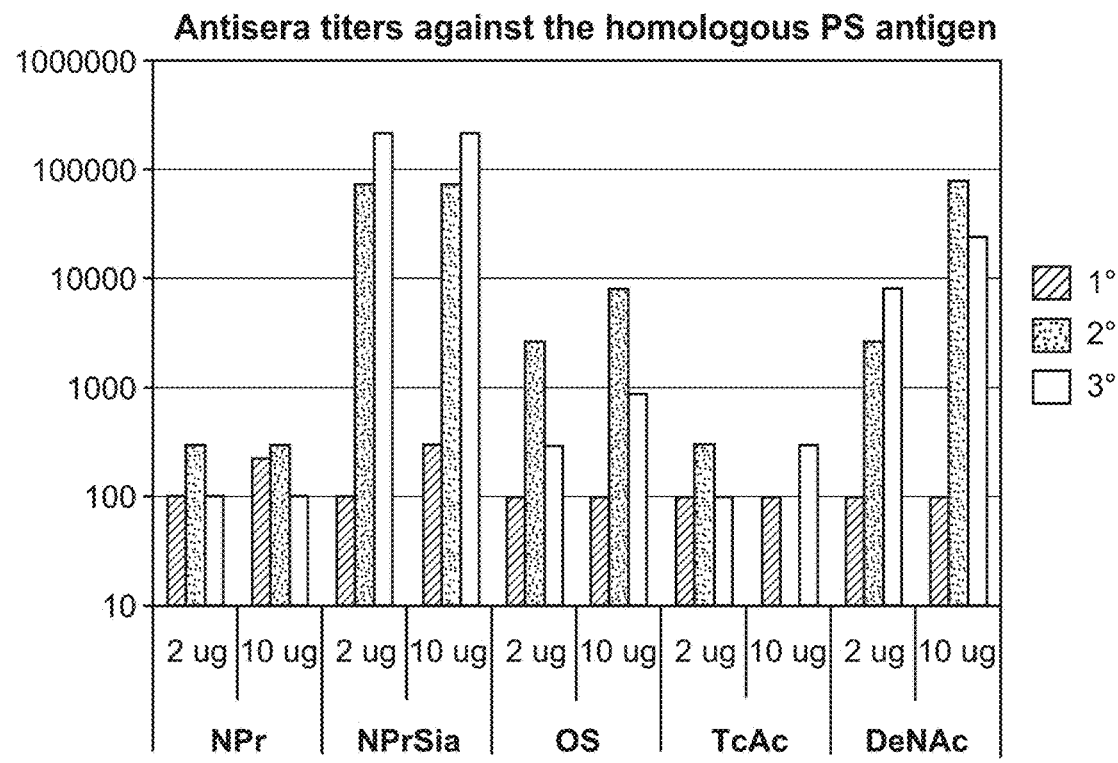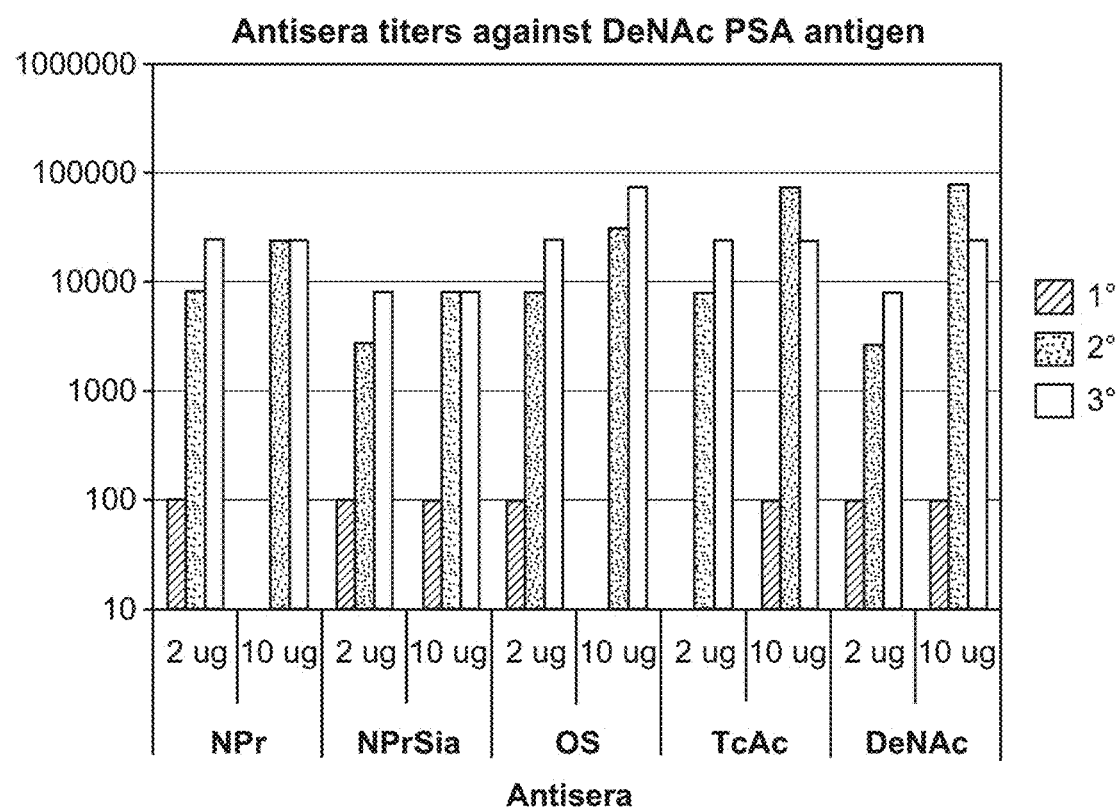
FIG. 10

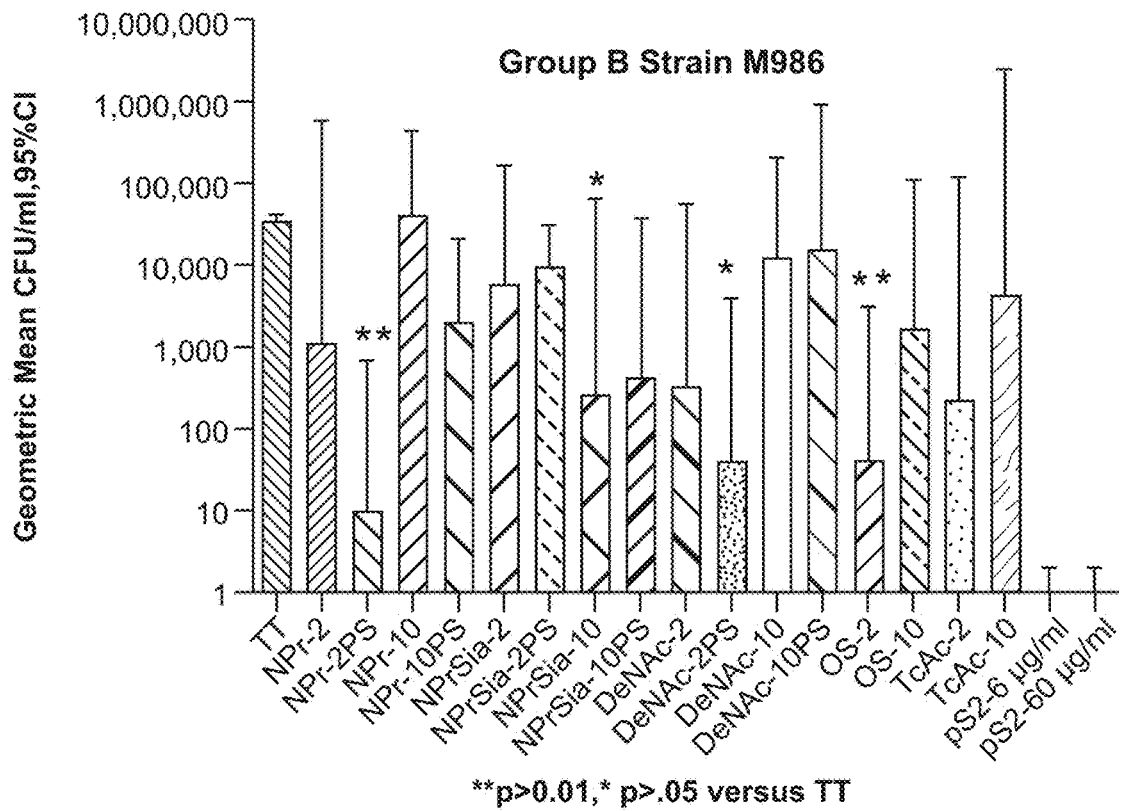
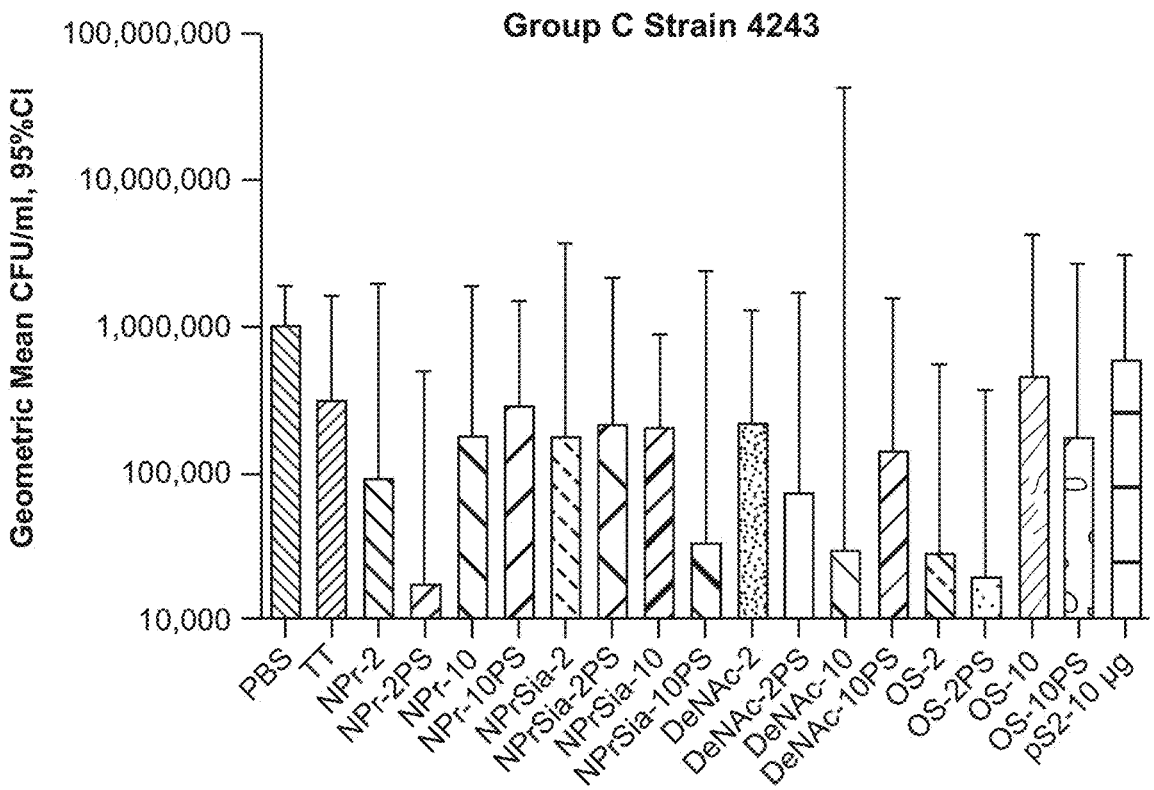
FIG. 13

```
                                                                   FR1 - IMGT
         <-----------------------------------------------                  15
         1           5            10              P   E   L   G   K   P
         E   V   K   L   E   Q   T   R   P   cct ... gaa ctg ggg aag cct
DA2HC    gag gtg aag ctg gaa cag act cga
                                                               <-
                                        25                           30
                     20          T   I   S   C   K   V   S   G   Y   S   F
         G   A   L   M   T                       aag gtt tct ggt tac tct ttc
DA2HC    ggg gct ttg atg acg ata tcc tgc
         CDR1 - IMGT
                                        35                 40              45
                                                           M   S   *   V   K   Q   S
         T   G   Y   Y                                     atg agc tga gtg aag caa agt
DA2HC    act ggc tac tac                                                              CDR2
         FR2 - IMGT                                        <-
                                        55                 60              T
                     50          L   E   W   I   G   E   I   N   P   S   T
         P   E   N   S                   gag att gga gag att aat cct agc act
DA2HC    cct gaa aat agc ctt
         - IMGT
                                        65                 70              75
                                                           Q   K   F   K   A   K
         G   G   S                       acc tac aac cag aag ttc aag ... gcc aag
DA2HC    ggt ggt agt
                                        FR3 - IMGT
                                        85                 90
                     80          V   D   K   S   S   T   A   V   Y   M   Q
         A   T   L   T                   gac aaa tcc agc aca gcc tac atg cag
DA2HC    gcc aca ttg act gta
                                        95                 100             104
                                                           S   A   V   Y   Y   C   A
         L   K   S   L   T   S   E   D   tct gag gac tct gca gtc tat tac tgt gca
DA2HC    ctc aag agc ctg aca
         CDR3 - IMGT
         R   R   G   F   S   Y   A   M   D   Y   W   G   Q   G   T
DA2HC    aga agg gga ttc tcc tat gct atg gac tac tgg ggt caa gga acc
```

FIG. 19

```
                                                          FR1 - IMGT
       1               5                10               15
       D   I   V   M   T   Q   T   A   S   L   A   V   S   L
DA2LC  gac att gtg atg aca cag act aca gct tct ttg gct gtg tct cta 20                25               30
       G   Q   R   A   T   I   S   C   R   A   S   E   S   V   E
DA2LC  ggg cag aga gcc acc atc tcc tgc aga gcc agt gaa agt gtt gaa
               CDR1 - IMGT                <-----

35                40                45
       Y   Y   G   T   S   L           M   Q   W   Y   Q   Q   K
DA2LC  tat tat ggc aca agt tta ... ... atg cag tgg tac caa cag aaa
       FR2 - IMGT                                              CDR2
                       ----->

50                55                60
       P   G   Q   P   P   K   L   L   I   Y   A   A   S
DA2LC  cca gga cag cca ccc aaa ctc ctc atc tat gct gca tcc ... ...
       - IMGT          <-----

65                70                75
                               N   V   E   S   G   V   P   A   R
DA2LC  ... ... ... ... ... ... aac gta gaa tct ggg gtc cct ... gcc agg
                                                    FR3 - IMGT 80                85                90
       F   S   G   S           G   T   D   F   S   L   N
DA2LC  ttt agt ggc agt ggg ... tct ggg aca gac ttc agc ctc aac
                                                              ----->

95               100               104
       I   H   P   V   E   E   D   D   I   A   M   Y   F   C   Q
DA2LC  atc cat cct gtg gag gag gat gat att gca atg tat ttc tgt cag
                      CDR3 - IMGT Q   S   R   K   V   P   Y   T   F   G   G   G   T   K   L
DA2LC  caa agt agg aag gtt cct tac acg ttc gga ggg ggg acc aag ctg
```

FIG. 20

OLIGOSIALIC ACID DERIVATIVES, METHODS OF MANUFACTURE, AND IMMUNOLOGICAL USES

CROSS-REFERENCE TO RELATED APPLICATION

This application is a continuation of U.S. Application Ser. No. 12/168,004 filed Jul. 3, 2008, now U.S. Pat. No. 9,333,247, which claims priority benefit of U.S. provisional application Ser. No. 60/958,342, filed Jul. 3, 2007, the disclosures of which applications are incorporated herein by reference in their entirety.

STATEMENT REGARDING FEDERALLY SPONSORED RESEARCH

This invention was made with government support under grant no. AI64314 awarded by the National Institute of Allergy and Infectious Diseases, and the National Institutes of Health. The government has certain rights in the invention.

TECHNICAL FIELD

This present disclosure relates to oligosialic acid derivatives, compositions containing the same, methods of their manufacture and use.

BACKGROUND

Sialic acid is an N- or O-substituted derivative of neuraminic acid. The N-substituted versions generally bear either an acetyl or a glycolyl group. In contrast, the O-substituted hydroxyl group may vary considerably, e.g., acetyl, lactyl, methyl, sulfate and phosphate groups. Polysialic acids are also quite common in which N-acetyl neuraminic acid residues are linked via the C2 ketal OH to another molecule by a glycosidic bond, e.g., poly alpha (2→8)N-acetyl neuraminic acid.

The sialic acids are biologically important carbohydrates found in organisms ranging from bacteria to humans. They are common features decorating the terminal ends of glycoproteins, glycans and glycosphingolipids, as well as other molecules. They mediate myriad normal cellular activities. This includes stabilizing glycoconjugates in cell membranes, regulating cell-cell interactions, acting as chemical messengers, regulating transmembrane receptor function, affecting membrane transport, controlling the half-lives of circulating glycoproteins and cells, and contributing to the permselectivity of the glomerular endothelium. See for review: Angata and Varki Chem. Rev. (2002) 102:439.

Given their prominent role in normal cellular activity, sialic acid and its derivatives have been used as markers for abnormal cellular processes such as cancer. (O'Kennedy et al., Cancer Lett., 1991 58:91; Vedralova et al. Cancer Lett. 1994 78:171; and Horgan et al., Clin. Chim. Acta., 1982 118:327; and Narayanan, S. Ann. Clin. Lab. Sci. 1994 24:376). For instance, cancer cells that can metastasize often have larger amounts of sialic acid-modified glycoproteins, which may help them enter the blood stream. Also, the sialic acid of tumor cells is modified in ways that differ from normal cells (Hakamori Cancer Res. 1996, 56:5309, Dall'Olio Clin. Mol. Pathol. 1996, 49:M126, Kim and Varki Glycoconj. J. 1997, 14:569).

One sialic acid derivative thought to be uncommon in normal cells, but present on cancer cells is de-N-acetyl sialic acid (Hanai et al J. Biol. Chem. 1988, 263:6296, Manzi et al J. Biol. Chem. 1990, 265:1309, Sjoberg et al J. Biol. Chem. 1995, 270:2921, Chamas et al 1999, Cancer Res. 59:1337; and Popa et al Glycobiology. 2007 17:367).

SEAM 3 is a murine monoclonal antibody that binds to poly alpha (2→8)N-acetyl neuraminic acid (polysialic acid or PSA) that contains de-N-acetyl residues (i.e., neuraminic acid) (Moe et al, Infect. Immun., 2005, 73:2123). SEAM 3 mediates bacteriolysis of *Neisseria meningitidis* group B (NmB) bacteria in the presence of exogenous complement and provides passive protection in an in vivo infant rat model of meningococcal bacteremia. SEAM 3 also binds to PSA antigens expressed in a variety of human tumors resulting in arrest of cell growth and a reduction in viability by inducing apoptosis and cell death.

Sodium borohydride is a reducing agent used to reduce aldehydes, ketones, imines, acid chlorides, and anhydrides. However, under mild basic conditions, it has also been shown to de-N-acetylate glycosaminoglycuronans (Hirano et al, Connect Tissue Res, 1975, 3:73) and cleave amide bonds in polypeptides (Shimamura et al, Arch Biochem Biophys, 1984, 232:699). A product of the sodium borohydride reduction is sodium borate. Borates and boranes are known to form cyclic esters with a variety of 1,2 or 1,3-diols in a 1:1 or 1:2 ratio. At pH<9 borates form complexes with the alpha caroboxylate of N-acetyl neuraminic acid and at pH>9 with the glycerol moiety at the non-reducing end (Djanashvili et al, Chem Eur J, 2005, 11:4010).

RELEVANT LITERATURE

Amino sugars, derivatives and related literature of interest are reported in the following U.S. Pat. Nos. 4,021,542; 4,062,950; 4,175,123; 4,216,208; 4,254,256; 4,314,999; 4,656,159; 4,713,374; 4,797,477; 4,803,303; 4,840,941; 4,914,195; 4,968,786; 4,983,725; 5,231,177; 5,243,035; 5,264,424; 5,272,138; 5,332,756; 5,667,285; 5,674,988; 5,759,823; 5,962,434; 6,075,134; 6,110,897; 6,274,568; 6,407,072; 6,458,937; 6,548,476; 6,697,251; 6,680,054; 6,936,701; and 7,070,801, and in the following references: Angata and Varki Chem. Rev. 2002, 102:439; Hakamori Cancer Res. 1996, 56:5309; Dall'Olio Clin. Mol. Pathol. 1996, 49:M126; Kim and Varki Glycoconj. J. 1997, 14:569; Hanai et al J. Biol. Chem. 1988, 263:6296; Manzi et al J. Biol. Chem. 1990, 265:1309; Sjoberg et al J. Biol. Chem. 1995, 270:2921; Chamas et al Cancer Res. 1999, 59:1337; Popa et al Glycobiology. 2007 17:367; Kayser et al J. Biol. Chem. 1992 267:16934; Keppler et al Glycobiology 2001, 11:11R; Luchansky et al Meth. Enzymol. 2003, 362:249; Oetke et al Eur. J. Biochem. 2001, 268:4553; Collins et al Glycobiology 2000, 10:11; and Bardor et al J. Biol. Chem. 2005, 280:4228.

The antibody SEAM 3 is reported in Moe et al, Infect. Immun., 2005, 73:2123. Sodium borohydride reactions and related are reported in various references, such as Hirano et al, Connect Tissue Res, 1975, 3:73; Shimamura et al, Arch Biochem Biophys, 1984, 232:699; and Djanashvili et al, Chem Eur J, 2005, 11:4010. See also See also US 2007/0010482; U.S. application Ser. No. 11/645,255, filed Dec. 22, 2006; WO 2006/002402; and PCT application serial no. PCT/US2006/04885, filed Dec. 22, 2006.

SUMMARY

The present invention relates to a method of producing, and compositions comprising an isolated alpha (2→8) and alpha (2→9) oligosialic acid derivative bearing a reducing end that is enriched for one or more de-N-acetyl residues and resistant to degradation by exoneuraminidase. This includes compositions that are enriched with alpha (2→8) or (2→9) oligosialic acid derivatives that bear a non-reducing end enriched for de-N-acetyl residues and resistant to degradation by exoneuraminidase, as well as aggregates of the derivatives. A representative method of production involves: (i) treating an alpha (2→8) or (2→9) oligosialic acid precursor having a reducing end and a non-reducing end with sodium borohydride under conditions for de-N-acetylating the non-reducing end; and (ii) isolating alpha (2→8) or (2→9) oligosialic acid derivative having one or more de-N-acetylated residues and a non-reducing end that is resistant to degradation by exoneuraminidase. An isolated alpha (2→8) or (2→9) oligosialic acid derivative produced by this method also is provided, as well as antibodies specific for the derivative, and compositions comprising the derivatives. The compositions comprising the aggregates are produced by the additional step of (iii) exposing the isolated alpha (2→8) or (2→9) oligosialic acid derivative to aggregating conditions, so as to form the aggregate, and, optionally, isolating the aggregate.

Also provided are methods of inhibiting growth of a cancerous cell in a subject. This method involves administering to the subject an effective amount of a pharmaceutically acceptable formulation comprising an antibody specific for an alpha (2→8) or (2→9) oligosialic acid derivative bearing a reducing end enriched for de-N-acetyl residues and resistant to degradation by exoneuraminidase, where the administering facilitates reduction in viability of cancerous cells exposed to the antibody.

Also featured is a method of eliciting antibodies to bacteria (e.g., *N. meningitidis, E. coli* K1) and/or to cancerous cells that bear a de-N-acetylated sialic acid (deNAc SA) epitope. This method involves administering to a subject an immunogenic composition comprising an isolated alpha (2→8) or (2→9) oligosialic acid derivative bearing a non-reducing end enriched for de-N-acetyl residues and resistant to degradation by exoneuraminidase, where the administering is effective to elicit production of an antibody that specifically binds to a deNAc SA epitope of the bacterial or cancerous cell. This includes immunogenic compositions that are enriched with alpha (2→8) or (2→9) oligosialic acid derivatives that bear a non-reducing end enriched for de-N-acetyl residues and resistant to degradation by exoneuraminidase. Also, the oligosialic acid derivatives and compositions can be used as a vaccine against bacteria with a de-N-acetyl sialic acid epitopes present in their polysaccharide capsules, such as *Neisseria*, especially *N. meningitidis*, particularly *N. meningitidis* Groups B and C, and *E. coli* K1.

Also provided are methods of detecting a cancerous cell in a subject. This method involves contacting a biological sample obtained from a subject suspected of having cancer with an antibody specific for an alpha (2→8) or (2→9) oligosialic acid derivative bearing a non-reducing end enriched for de-N-acetyl residues and resistant to degradation by exoneuraminidase, where binding of the antibody is indicative of the presence of cancerous cells in the subject.

Kits containing one or more compositions of the present disclosure, as well as those with instructions for use in a method of the present disclosure also are provided.

Accordingly, in one aspect the present disclosure provides methods of producing an isolated alpha (2→8) or (2→9) oligosialic acid derivative comprising generating an alpha (2→8) or (2→9) oligosialic acid derivative having one or more de-N-acetylated residues by treating an alpha (2→8) or (2→9) oligosialic acid precursor having a reducing end and a non-reducing end with sodium borohydride under conditions for de-N-acetylating the non-reducing end; and isolating the alpha (2→8) or (2→9) oligosialic acid derivative having (i) a degree of polymerization of about 2-20, and (ii) one or more de-N-acetylated residues and a non-reducing end that is resistant to degradation by exoneuraminidase, whereby the isolated alpha (2→8) or (2→9) oligosialic acid derivative is produced.

In related embodiments, the non-reducing end of the oligosialic acid derivative is a de-N-acetylated residue, In specific embodiments, the de-N-acetylated residue is neuraminic acid. In related embodiments, the oligosialic acid derivative comprises one or more N-acyl groups other than N-acetyl, In one embodiment, the N-acyl group is trichloroacetyl. In related embodiments, the oligosialic acid precursor is obtainable from acid hydrolysis of a polysialic acid polymer obtainable from a bacterium selected from the group consisting of *E. coli* K1, *Neisseria meningitidis* serogroup B, and *Neisseria meningitidis* serogroup C.

In related embodiments, the oligosialic acid derivative has a degree of polymerization of about 2 to 10. In related embodiments, the oligosialic acid derivative is comprised as an isolated mixture of alpha (2→8) or (2→9) oligosialic acid chains, where in some embodiments the mixture of alpha (2→8) or (2→9) oligosialic acid chains comprises shorter length chains and a ratio of sialic acid to de-N-acetylated sialic acid of 3:1 and/or comprises longer length chains and a ratio of sialic acid to de-N-acetylated sialic acid of 10:1. In related embodiments, the isolated oligosialic acid derivative is capable of inhibiting SEAM 2, SEAM 3, or DA2 binding to dodecylamine N-propionyl NmB polysialic acid or N-propionyl NmB polysialic acid at an IC50 of less than about 0.1 μg/ml.

In related embodiments, the method further comprises conjugating a second molecule to the isolated alpha (2→8) or (2→9) oligosialic acid derivative, wherein the second molecule is selected from the group consisting of protecting group, amino acid, peptide, polypeptide, lipid, carbohydrate, nucleic acid and detectable label. In some embodiments, the second molecule is an immunomodulatory (e.g., a toxin or derivative thereof (e.g., a tetanus toxoid)).

In other embodiments, the method further comprises enriching for alpha (2→8) oligosialic acid derivative having a non-reducing end that is resistant to degradation by exoneuraminidase by exposure of the alpha (2→8) or (2→9) oligosialic acid derivative to exoneuraminidase. In related embodiments, the oligosialic acid derivative is provided in an aggregate (e.g., an aggregate comprising microscopic particles).

The present disclosure also provides isolated alpha (2→8) or (2→9) oligosialic acid derivatives produced according to the methods of the present disclosure, as well as compositions comprising such compounds.

In another aspect, the present disclosure provides compositions comprising an isolated alpha (2→8) or (2→9) oligosialic acid derivative produced according to the method of claim 1, wherein the isolated alpha (2→8) or (2→9) oligosialic acid derivative comprises as mixture of oligosialic acid derivatives of variable chain lengths each having a non-reducing end de-N-acetyl residue.

In another aspect, the present disclosure provides compositions comprising an alpha (2→8) or (2→9) oligosialic acid derivative having a degree of polymerization of about 2-20, and a reducing end and a non-reducing end, wherein the non-reducing end comprises a de-N-acetylated residue that is resistant to degradation by exoneuraminidase. In related embodiments, the non-reducing end of the oligosialic acid derivative is a de-N-acetylated residue. In related embodiments, the de-N-acetylated residue is neuraminic acid. In related embodiments, the oligosialic acid derivative comprises one or more N-acyl groups other than N-acetyl. In related embodiments, the reducing end of the isolated oligosialic acid derivative is reduced. In related embodiments, the oligosialic acid is obtainable from a polysialic acid polymer obtainable from a bacterium selected from the group consisting of E. coli K1, Neisseria meningitidis serogroup B, and Neisseria meningitidis serogroup C. In further related embodiments, 25 the oligosialic acid derivative comprises a degree of polymerization of about 2 to 10.

In related embodiments, the oligosialic acid derivative is comprised as an isolated mixture of oligosialic acid chains where, for example, the mixture of oligosialic acid chains comprises shorter length chains and a ratio of sialic acid to de-N-acetylated sialic acid of about 3:1 and/or the mixture of oligosialic acid chains comprises longer length chains and a ratio of sialic acid to de-N-acetylated sialic acid of about 10:1.

In related embodiments, the oligosialic acid derivative comprises a conjugate, e.g., where the oligosialic acid derivative is conjugated to one or more second molecules selected from the group consisting of protecting group, amino acid, peptide, polypeptide, lipid, carbohydrate, nucleic acid and detectable label. In some embodiments, the second molecule is an immunomodulatory (e.g., a a toxin or derivative thereof (e.g., a tetanus toxoid)). In related embodiments, the oligosialic acid derivative is comprised as a formulation containing one or more immunogenic excipients. In related embodiments, the oligosialic acid derivative is capable of inhibiting SEAM 2, SEAM 3 and DA2 binding to dodecylamine N-propionyl NmB polysialic acid or N-propionyl NmB polysialic acid at an IC50 of less than about 0.1 µg/ml. In related embodiments, the isolated alpha (2→8) or (2→9) oligosialic acid derivative comprises as mixture of oligosialic acid derivatives of variable chain lengths that have a non-reducing end enriched with de-N-acetyl residues. In related embodiments, the oligosialic acid derivative is provided in an aggregate (e.g., aggregates comprising microscopic particles).

In another aspect, the present disclosure provides isolated antibodies specific for an alpha (2→8) or (2→9) oligosialic acid derivative that comprises a non-reducing end enriched for one or more de-N-acetylated residues and is resistant to degradation by exoneuraminidase. In related embodiments, the antibody is specific for alpha (2→8) or (2→9) oligosialic acid derivative in an aggregate, e.g., aggregates comprising a microscopic particle. In related embodiments, the antibody is capable of complement mediated bacteriolysis and opsonophagocytosis of Neisseria meningitidis group B (NmB) and group C (NmC) bacteria. In related embodiments, the antibody is capable of binding neuraminic acid-containing antigens expressed by dividing or non-dividing Jurkat T-cell leukemia cells, and in further related embodiments, the antibody binds the non-dividing Jurkat T-cell leukemia cells better than SEAM 3. In related embodiments, the antibody is of mouse origin. In further related embodiments, the antibody is specific for non-reducing end de-N-acetyl sialic acid residue.

In specific embodiments, the antibody is a monoclonal antibody having a light and heavy chain variable complementarity determining region polypeptide sequence as depicted in FIGS. 19 and 20, and in specific embodiments is a monoclonal antibody having a complementarity determining region (CDR) polypeptide sequence selected from a CDR polypeptide sequence depicted in FIG. 19 or 20. In related embodiments, the monoclonal antibody is a humanized monoclonal antibody.

In related aspects, the present disclosure provides methods of detecting a cancerous cell in a subject, the method comprising contacting a biological sample obtained from a subject suspected of having cancer with an antibody according to the present disclosure, wherein the binding of the antibody is indicative of the presence of cancerous cells in the subject. In further related aspects, the present disclosure provides methods of inhibiting growth of a cancerous cell in a subject comprising administering to the subject an effective amount of a pharmaceutically acceptable formulation comprising an antibody of the present disclosure, wherein the administering facilitates reduction in viability of cancerous cells exposed to the antibody. In still other related aspects, the present disclosure provides methods of eliciting antibodies in a subject, where the antibodies specifically bind a bacteria comprising a de-N-acetylated sialic acid (deNAc SA) epitope comprising administering to a subject an immunogenic composition comprising an alpha (2→8) or (2→9) oligosialic acid derivative having a degree of polymerization of about 2 to 20, and a reducing end and a non-reducing end, wherein the non-reducing end is enriched for one or more de-N-acetylated residues and resistant to degradation by exoneuraminidase, and wherein the administering is effective to elicit production of an antibody that specifically binds a deNAc SA epitope of a bacteria. In related embodiments, the bacteria is Neisseria meningitidis group B, Neisseria meningitidis group C, or Escherichia coli K1.

In another aspect, the present disclosure provides methods of eliciting antibodies to a cancerous cell comprising a de-N-acetylated sialic acid (deNAc SA) epitope in a subject comprising administering to a subject an immunogenic composition comprising an alpha (2→8) or (2→9) oligosialic acid derivative having a degree of polymerization of about 2 to 20, and a reducing end and a non-reducing end, wherein the non-reducing end is enriched for one or more de-N-acetylated residues and resistant to degradation by exoneuraminidase, and wherein the administering is effective to elicit production of an antibody that specifically binds a deNAc SA epitope of the cancerous cell. In related embodiments, the cancer is a melanoma, a lymphoma, or a neuroblastoma.

In related embodiments, the alpha (2→8) or (2→9) oligosialic acid derivative of the immunogenic composition is prepared by selective de-acetylation of non-reducing end residue by sodium borohydride reduction. In related embodiments, the alpha (2→8) or (2→9) oligosialic acid derivative is a conjugate.

In related embodiments, the alpha (2→8) or (2→9) oligosialic acid derivative is administered by infusion or by local injection. In related embodiments, administering can be prior to surgical intervention to remove cancerous cells, at the time of or after surgical intervention to remove cancerous cells, and/or administered in conjunction with at least one of an immunotherapy, a cancer chemotherapy or a radiation therapy. In related embodiments, the isolated alpha (2→8) or (2→9) oligosialic acid derivative comprises an aggregate of the polysialic acid derivative (e.g., aggregates comprising microscopic particles). In related embodiments, In another aspect, the present disclosure provides methods of producing an aggregate comprising an alpha (2→8) or (2→9) oligosialic acid derivative comprising admixing one or more alpha (2→8) or (2→9) oligosialic acid derivatives under aggregating conditions so as to form an aggregate. In related embodiments, the aggregating conditions is heating (e.g., heating from 30° C. to 70° C.) or the addition of an aggregating excipient (e.g., aluminum hydroxide). In related embodiments, the aggregate is a particle, e.g., a microscopic particle. In related embodiments, the polysialic acid derivative has a mixture of N-acetyl and de-N-acetyl residues and is resistant to degradation by exoneuraminidase.

Figure 18:
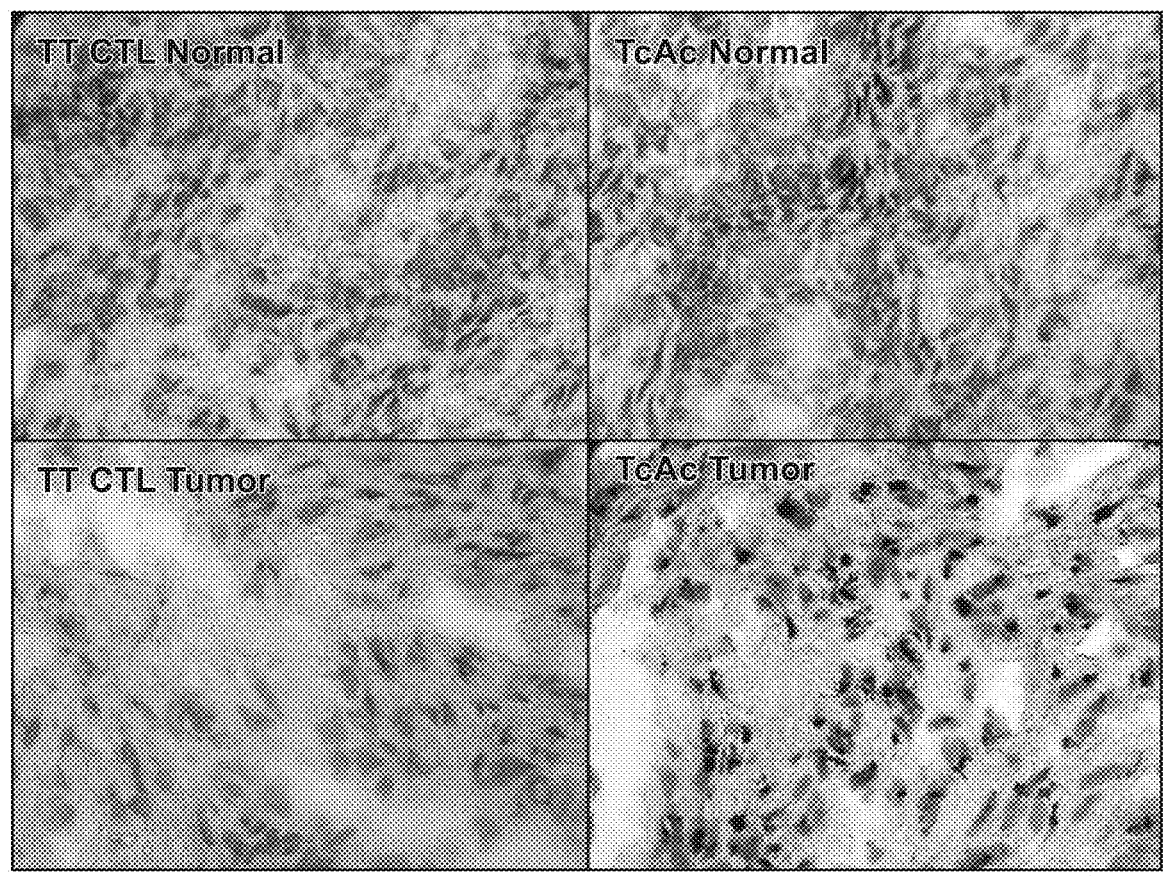

In other aspects, the present disclosure provides, vaccine compositions comprising an isolated alpha (2→8) or (2→9) oligosialic acid derivative having (i) a degree of polymerization of about 2-20, (ii) an IC50 of less than about 0.1 µg/ml for inhibiting SEAM 2, SEAM 3 or DA2 antibody binding to dodecylamine N-propionyl NmB polysialic acid or N-propionyl NmB polysialic acid, and (iii) a non-reducing end de-N-acetyl residue that is resistant to degradation by exoneuraminidase. In related embodiments, the derivative comprises one or more N-trichloroacetyl sialic acid residues. In related embodiments, the derivative comprises one or more N-propionyl sialic acid residues. In related embodiments, the derivative has a degree of polymerization of about 2-10 and/or about 2-6. In related embodiments, the derivative is selected from the group consisting of dimer, trimer and tetramer. In related embodiments, the derivative comprises a conjugate (e.g., is conjugated to a second molecule comprising an immunomodulatory, such as a toxin or derivative thereof (e.g., a tetanus toxoid)). Exemplary immunomodulatory conjugates of derivatives of the present disclosure include NPrSia-TT, OS-TT, and TcAc-TT.

In another aspect, the present disclosure provides vaccine compositions comprising an isolated alpha (2→8) or (2→9) oligosialic acid derivative having (i) a degree of polymerization of about 2-20, (ii) a de-N-acetyl sialic acid content of about 50% to 98%, and (iii) a non-reducing end de-N-acetyl residue that is resistant to degradation by exoneuraminidase. In related embodiments, the derivative has a de-N-acetyl sialic acid content of about 88% to 98%. In related embodiments, the derivative has a degree of polymerization of about 2-10 and/or about 2-6. In related embodiments, the derivative is a dimer, trimer or tetramer. In related embodiments, the derivative vaccine comprises a conjugate (e.g., is conjugated to a second molecule comprising an immunomodulatory, such as a toxin or derivative thereof (e.g., a tetanus toxoid)). Exemplary immunomodulatory conjugates of derivatives of the present disclosure include NPrSia-TT, OS-TT, and TcAc-TT. In related embodiments, the derivative is DeNAc-TT.

In aspects relating to vaccine compositions, related embodiments include vaccine compositions comprising an adjuvant. Furthermore, related embodiments of such aspects include vaccine compositions wherein the derivative is present in the composition in an effective amount to elicit production of an antibody that specifically binds a deNAc SA epitope of a cell in a subject administered the vaccine composition.

Other features of the invention are described herein, and will also be readily apparent to the ordinarily skilled artisan upon reading the present disclosure.

BRIEF DESCRIPTION OF FIGURES

FIG. 1 depicts the results of anion exchange chromatography of sodium borohydride-treated oligosialic acid (OS).

FIG. 2 depicts the results of analysis of column fractions from anion exchange chromatography by high performance anion exchange chromatography with pulsed ampermetric (HPAC-PAD) detection.

FIG. 3 is a Western blot of the OS-tetanus toxoid (OS-TT) conjugate vaccine using SEAM 3 as the primary detecting antibody.

FIG. 4 summarizes the OS-specific antibody titers resulting from immunizing CD1 mice with the OS-TT conjugate vaccine.

FIG. 5 shows the measurement of complement factor deposition on live NmB bacteria by flow cytometry mediated by pooled antisera from mice immunized with the OS-TT conjugate vaccine.

FIG. 6 is a fluorescence micrograph of bacteria show deposition of complement factors on the cells mediated by pooled antisera from mice immunized with the OS-TT conjugate vaccine.

FIG. 7 is a bar graph showing the effect of pooled antisera from mice immunized with the OS-TT conjugate vaccine on the growth of *N. meningitidis* serogroup B (NmB) bacteria in an ex vivo human blood model of meningococcal bacteremia.

FIG. 8 shows the measurement of antibodies elicited by immunization of CD1 mice with the OS-TT conjugate vaccine binding to Jurkat T-cell leukemia cells by flow cytometry.

FIG. 9 is a Western blot of the PS-tetanus toxoid conjugate vaccines using SEAM 18, SEAM 2, or SEAM 3 as primary detecting antibodies.

FIG. 10 summarizes the ELISA titers of antiserum pools from CD1 mice immunized with 1, 2, or 3 doses of 2 μg or 10 μg of total sialic acid of each of the PS-tetanus toxoid conjugate vaccines. The upper panel shows the titers against the homologous PS antigens and lower panel shows the titers against the DeNAc antigen.

FIGS. 11A and 11B summarize the results of measuring control and antiserum antibody binding to N. *meningtidis* group B strain NMB by flow cytometry. FIG. 11A shows of binding of IgG and IgM antibodies for all antiserum pools. FIG. 11B shows binding for each IgG subclass of the 10 μg dose $3^{rd}$ injection DeNAc antiserum pool.

FIGS. 12A and 12B shows the ability of vaccine elicted antibodies to activate complement protein deposition on N. *meningitidis* group B strain NMB (FIG. 12A) and group C strain 4243 (FIG. 12B).

FIG. 13 shows the results of evaluating the ability of PS-conjugate vaccine elicited antisera to passively protect in an infant rat model of meningococcal bacteremia. The upper panel shows the results for challenge with *N. meningitidis* group B strain M986 and the lower panel for group C strain 4243.

FIG. 14 is a bar graph showing the effect of pooled antisera from mice immunized with the PS-conjugate vaccines on the growth of *N. meningitidis* group B strain NZ98/254 bacteria in an ex vivo human blood model of meningococcal bacteremia.

FIG. 15 is a bar graph showing the measurement of antibodies elicted by immunization of CD1 mice with the PS-conjugate vaccines binding to Jurkat T-cell leukemia cells by flow cytometry.

FIG. 16 is a bar graph showing the measurement of the ability of antibodies elicted by immunization of CD1 mice with the PS-conjugate vaccines to activate deposition of human complement proteins on Jurkat T-cell leukemia, SK-MEL 28 melanoma, and CHP-134 neuroblastoma cells by flow cytometry.

FIG. 17 is a bar graph showing the measurement of the ability of antibodies elicted by immunization of CD1 mice with the PS-conjugate vaccines to decrease the viability of Jurkat T-cell leukemia cells.

FIG. 18 is a set of light micrographs of immunohistochemical staining of normal ovary and a primary ovarian tumor with polyclonal antisera elicited by immunization of CD1 mice with tetanus toxoid carrier protein or TcAc-tetanus toxoid vaccine.

FIG. 19 shows the relationship of the DNA sequence (SEQ ID NO:1) and corresponding amino acid sequence translation (SEQ ID NO:2) of the DA2 heavy chain variable region gene to variable region framework and CDRs as defined by International Immunogenetics Information System (IMGT) definitions (Lefranc et al. IMGT, the international ImMunoGeneTics information system®. Nucl. Acids Res., 2005, 33, D593-D597).

FIG. 20 shows the relationship of the DNA sequence (SEQ ID NO:3) and corresponding amino acid sequence translation (SEQ ID NO:4) of the DA2 light chain variable region gene to variable region framework and CDRs as defined by International Immunogenetics Information System (IMGT) definitions (Lefranc et al. IMGT, the international ImMunoGeneTics information system®. Nucl. Acids Res., 2005, 33, D593-D597).

Figure 21:
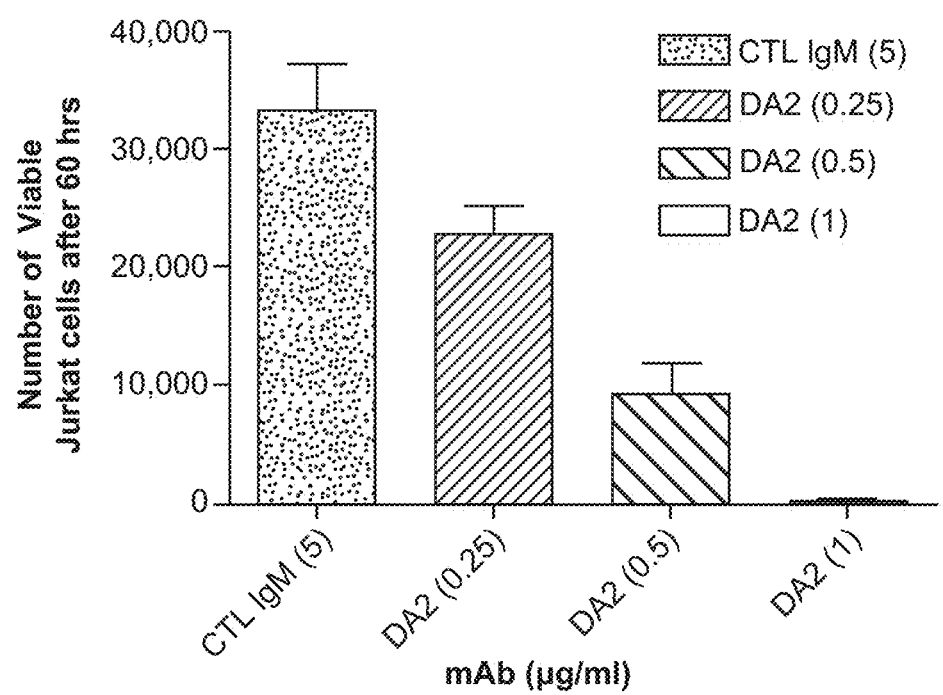

FIG. 21 is a bar graph showing the measurement of the ability of the monoclonal antibody to decrease the viability of Jurkat T-cell leukemia cells compared to an irrelevant IgM control antibody.

DETAILED DESCRIPTION OF EXEMPLARY EMBODIMENTS

It was discovered that oligosialic acid derivatives bearing a non-reducing end de-N-acetyl residue elicit antibodies highly specific for *E. coli* K1, *N. meningitidis*, and cancer cells expressing this immunodominant epitope. The derivatives of the present disclosure can be produced by treatment of oligomers of sialic acid (N-acetyl neuraminic acid oligosaccharides (OS) ranging from dimers to multimers, e.g., of up to about 100 monomer units in length) with sodium borohydride under conditions that produce oligosialic acid product having derivatives with a non-reducing end that is enriched with one or more de-N-acetyl residues and resistant to treatment with exoneuraminidase. The products of the sodium borohydride reaction are highly reactive with antibodies such as SEAM 3. It also has been discovered that the OS derivatives containing the minimal features necessary for activity have (i) a degree of polymerization of about 2-20, particularly sub-ranges thereof of dimer, trimer and/or tetramer, and (ii) an immunodominant non-reducing end de-N-acetyl residue that is resistant to degradation by exoneuraminidase. Compounds have been produced with these and other features that can be exploited for a given end use. When conjugated to a carrier protein and used to immunize mice, the non-reducing end enriched de-N-acetylated oligosaccharide products elicit antibodies that are protective against *N. meningitidis* serogroup B (NmB), as well as other bacteria expressing the immunodominant non-reducing end de-N-acetyl residue. They also bind to neuraminic acid-containing polysialic acid (PSA) antigens expressed by tumor cells. The disclosure is further based on the discovery that the OS derivatives can be composed of alpha (2→8) and/or alpha (2→9) linked oligosialic acid material. The disclosure also is based on the discovery that aggregates of the OS derivatives are more readily taken up by cells and expressed on the cell surface as compared to the corresponding non-aggregated OS derivative. The aggregates can be exploited in conjunction with or in the absence of carrier protein to elicit a strong T-cell dependent immune response. Antibody specific for the immunodominant non-reducing end de-N-acetyl residue epitope have also been discovered. The data support broad use of the methods and compositions, including the diagnosis and treatment of multiple types of cancer in humans, as well as diagnosis of and protection against disease caused by bacteria such as *E. coli* K1 and *Neisseria*.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

When describing the compositions, pharmaceutical formulations containing such, and methods of producing and using such compositions, the following terms have the following meanings unless otherwise indicated. It should also be understood that any of the moieties defined forth below may be substituted with a variety of substituents, and that the respective definitions are intended to include such substituted moieties within their scope.

The term "amino sugar" refers to a sugar or saccharide that contains an amino group in place of a hydroxyl group. Derivatives of amino containing sugars, such as N-acetyl-glucosamine, N-acetyl mannosamine, N-acetyl galactosamine, N-acetyl neuraminic acid and sialic acids in general are examples of amino sugars.

The term "analog" or "analogue" refers to without limitation any compound which has structural similarity to the compounds of the present disclosure and would be expected, by one skilled in the art, to exhibit the same or similar utility as the claimed and/or referenced compounds.

The term "carrier" as used in the context of a carrier conjugated to an alpha (2→8) oligosialic acid derivative generally refers to a peptide or protein carrier, such as an antibody or antibody fragment. "Carrier" encompasses peptides or proteins that enhance immunogenicity of a compound.

The term "cell surface antigen" (or "cell surface epitope") refers to an antigen (or epitope) on surface of a cell that is extracellularly accessible at any cell cycle stage of the cell, including antigens that are predominantly or only extracellularly accessible during cell division. "Extracellularly accessible" in this context refers to an antigen that can be bound by an antibody provided outside the cell without need for permeabilization of the cell membrane.

The term "chemotherapy" as used herein refers to use of an agent (e.g., drug, antibody, etc.), particularly an agent(s) that is selectively destructive to a cancerous cell, in treatment of a disease, with treatment of cancer being of particular interest.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", and encompasses cancer cells of a solid tumor, a semi-solid tumor, a primary tumor, a metastatic tumor, and the like.

The term "conjugated" generally refers to a chemical linkage, either covalent or non-covalent, usually covalent, that proximally associates one molecule of interest with second molecule of interest.

The term "de-N-acetyl sialic acid antigen" (which may also be referred to as "de-N-acetylated sialic acid antigen" or "deNAc SA antigen") refers to a compound having or mimicking a deNAc sialic acid epitope (deNAc SA epitope), which epitope is minimally defined by a dimer of residues of sialic acid or sialic acid derivative, where the dimer contains at least one de-N-acetylated sialic acid residue adjacent an N-acylated (e.g., acetylated or propionylated) sialic acid residue or a sialic acid derivative residue. Examples of de-N-acetyl sialic acid antigens are provided in the present disclosure, and include, without limitation, de-N-acetylated polysaccharide derivatives ("PS derivatives"), de-N-acetylated gangliosides, and de-N-acetylated derivatives of a sialic-acid modified protein, particularly a sialic-acid modified protein that is accessible at an extracellular surface of a mammalian cell, particularly a human cell, more particularly a cancer cell, particularly a human cancer cell. DeNAc SA epitopes are also present in polysaccharide capsules of Neisseria, especially N. meningitidis, particularly N. meningitidis Group B, and E. coli K1. It should be noted that description of a deNAc SA antigen as a derivative of a starting molecule (e.g., PS derivative or ganglioside derivative) is not meant to be limiting as to the method of production of the de-N-acetyl sialic acid antigen, but rather is meant as a convenient way to describe the structure of the exemplary deNAc SA antigen.

The term "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

The term "effective amount" of a compound as provided herein is intended to mean a non-lethal but sufficient amount of the compound to provide the desired utility. For instance, for eliciting an immune response in a subject to generate anti-deNAc SA antibodies, the effective amount is the amount which elicits a useful antibody response, e.g., so as to provide for production of antibodies that can be subsequently isolated (e.g., as in monoclonal antibody production) or to provide for a clinically meaningful immune response in a subject against a bacteria (e.g., as in the context of prophylactic or therapeutic immunization against a disease caused by Neisseria or E. coli K1) or by a cancer characterized by a deNAc SA epitope. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "immunotherapy" refers to treatment of disease (e.g., Neisseria or E. coli K1 bacterial infection, cancer) by modulating an immune response to a disease antigen. In the context of the present application, immunotherapy refers to providing an antibacterial and/or anti-cancer immune response in a subject by administration of an antibody (e.g., a monoclonal antibody) and/or by administration of an antigen that elicits an anti-tumor antigen immune response in the subject.

The term "inactivation" of a cell is used herein to indicate that the cell has been rendered incapable of cell division to form progeny. The cell may nonetheless be capable of response to stimulus and/or biosynthesis for a period of time, e.g., to provide for production of a cell surface molecule (e.g., cell surface protein or polysaccharide).

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art and described more fully below.

The term "non-reducing end" of an oligo or polysaccharide chain is intended the end portion of the chain bearing the non-reducing glycosyl residue.

The term "reducing end" of an oligo or polysaccharide chain is intended the end portion of the chain bearing the reducing glycose residue. This is the end of the chain that, when bearing a free anomeric carbon in basic solution, is capable of forming an aldehyde or ketone.

The term "enriched" as used herein refers to a compound or composition that has an increase in the proportion of a desirable property or element. For example, an alpha (2→8) oligosialic acid derivative that is "enriched" for de-N-acetylation at a non-reducing end is an alpha (2→8) oligosialic acid derivative in which the de-N-acetylated residues are primarily present, including only present, at a non-reducing end, including the non-reducing terminal end. A composition is "enriched" for alpha (2→8) oligosialic acid derivatives having de-N-acetylated non-reducing ends where the majority of alpha (2→8) oligosialic acid derivatives in the composition (e.g., more than 50%, 55%, 60%, 65%, 70%, 75%, 80%, 85%, 90%, 95% or more up to 100%) have a de-N-acetylated residue at a non-reducing end, particularly at a non-reducing terminal end.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "SEAM 3-reactive antigen" refers to an antigen having an epitope that is specifically bound by the monoclonal antibody (mAb) SEAM 3 (ATCC Deposit No. HB-12170). The term "DA2-reactive antigen" refers to an antigen having an epitope that is specifically bound by the monoclonal antibody (mAb) DA2 (described herein). The monoclonal antibody DA2 is highly specific for any non-reducing end neuraminic acid residue, regardless of the adjacent residue or glycosidic linkage. Exemplary SEAM 3 and/or DA2-reactive antigens are provided in the working examples. The antibodies disclosed herein generated by an oligosialic acid-conjugate vaccine (OS-conjugate vaccine) also include those that have antigen specificity other than binding to an epitope bound by SEAM 3, and may bind the same or different antigen, but does not bind normal PSA control (i.e., normal polysialic acid that is devoid of de-N-acetyl residues), and binds to OS-conjugate vaccine-generated antigen better than SEAM 3 relative to normal PSA control. For example, DA2 binds the immunodominant de-N-acetyl residue epitope better than SEAM 3, and as noted above, recognizes with high specificity any non-reducing end neuraminic acid residue, regardless of the adjacent residue or glycosidic linkage.

By "degree of polymerization" or Dp is intended the number of repeat units in an average polymer chain. Chain length can be reported in monomer units, as molecular weight, or both.

The term "subject" is intended to cover humans, mammals and other animals which contain polysialic acid in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor, where the cancer is one associated with cancerous cells expressing a de-N-acetyl sialic acid antigen. Samples obtained from such subject are likewise suitable for use in the methods of the present disclosure.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

Exemplary methods and compositions employable therein are described first in greater detail, followed by a review of the various specific compositions, formulations, kits and the like that may find use in the methods of the present disclosure, as well as a discussion of representative applications in which the methods and compositions of the present disclosure find use.

Methods of Production and Compositions

As summarized above, the present disclosure provides oligosialic acid (OS) derivatives bearing a non-reducing end de-N-acetyl residue that elicit antibodies highly specific for *E. coli* K1, *N. meningitidis*, and cancer cells expressing this immunodominant epitope. The OS derivatives generally have (i) a degree of polymerization of about 2-20, particularly sub-ranges thereof of dimer, trimer and/or tetramer, and (ii) an immunodominant non-reducing end de-N-acetyl residue that is resistant to degradation by exoneuraminidase. The OS derivatives can be composed of alpha (2→8) and/or alpha (2→9) linked oligosialic acid material. Also provided are methods of producing an isolated alpha (2→8) or alpha (2→9) oligosialic acid derivative bearing a non-reducing end enriched for one or more de-N-acetyl residues and that is resistant to degradation by exoneuraminidase. This also includes a method for the production of aggregates of the oligosialic acid derivatives, as well as compositions and pharmaceutical formulations thereof. The products of the process find use in the production of oligosialic acid derivative compositions and antibodies specific for the derivatives for a variety of applications, including use in various methods of treating a host suffering from disease or condition in need thereof, e.g., for the diagnosis and/or treatment of a subject using an immunogenic and/or vaccine composition and/or antibody derived from an oligosialic acid derivative of the present disclosure (as described in greater detail below).

As noted above, compositions of the present disclosure include an isolated alpha (2→8) or (2→9) oligosialic acid derivative having a degree of polymerization of about 2-20, and a non-reducing end comprising a de-N-acetylated residue that is resistant to degradation by exoneuraminidase. Thus, for example, an oligosialic acid derivatives include those that comprise a polymer of sialic and neuraminic acid monomers joined essentially through alpha (2→8) or alpha (2→9) glycosidic linkages. One or more of the sialic and neuraminic acid monomers of a polysialic acid may be modified or conjugated to a second molecule, such as a partially or fully O-acetylated monomer of sialic and/or neuraminic acid. In general, the oligosialic acid is obtainable from a polysialic acid polymer, for example, from a bacterium such as *E. coli* K1, *Neisseria meningitidis* serogroup B, and *Neisseria meningitidis* serogroup C, or can be synthesized de novo by other methods as described in more detail below.

In some embodiments, the oligosialic acid derivative is comprised essentially of a mixture of N-acetyl and de-N-acetyl sialic acid residues, such as N-acetyl neuraminic acid and de-N-acetyl neuraminic acid. In other embodiments, the oligosialic acid derivative comprises one or more N-acyl groups other than N-acetyl, such as a trichloroacetyl or propionyl group.

In particular embodiments, the oligosialic acid derivative comprises a particular degree of polymerization, such as degree of polymerization of about 2 to 10, and sub-ranges thereof of dimer, trimer and/or tetramer. In some embodiments, the oligosialic acid derivative is comprised as an isolated mixture of oligosialic acid chains. In particular embodiments, the mixture of oligosialic acid chains comprise shorter length chains. In other embodiments, the mixture of oligosialic acid chains comprises longer length chains. In certain embodiments, the oligosialic acid derivative is purified so as to be enriched for the desired mixture of chains, or is purified to consist essentially of a single species of chain.

The compositions of the present disclosure include an effective amount of the oligosialic acid derivative to achieve the desired end result. For example, the compositions generally include an effective amount of the derivative to elicit production of an antibody that specifically binds a deNAc SA epitope of a cell in a subject administered the vaccine composition. In some instances, the antibody is immunoglobulin G (IgG), which may include a predominant response in which one or more subclasses of IgG are elicited, such as IgG1, IgG2, IgG3, and IgG4. Of specific interest are IgG3 and IgG1. In other embodiments, the compositions of the present disclosure include an isolated oligosialic acid derivative in which the composition is substantially free of other oligosialic acid material, and in certain embodiments, is substantially free of oligosialic acid derivative having an N-acetyl sialic acid residue.

A featured aspect is a vaccine composition that includes an oligosialic acid derivative of the present disclosure. The vaccine compositions may include oligosialic acid that is conjugated or unconjugated, and may optionally further include an adjuvant to enhance the effectiveness of the vaccine composition.

In certain embodiments, the vaccine composition comprises an isolated alpha (2→8) or (2→9) oligosialic acid derivative having (i) a degree of polymerization of about 2-20, (ii) an IC50 of less than about 0.1 μg/ml for inhibiting SEAM 2, SEAM 3, or DA2 antibody binding to dodecylamine N-propionyl NmB polysialic acid or N-propionyl NmB polysialic acid, and (iii) a non-reducing end de-N-acetyl residue that is resistant to degradation by exoneuraminidase. A featured aspect of this embodiment is where the oligosialic acid derivative comprises one or more N-acyl groups other than N-acetyl, such as one or more N-trichloroacetyl sialic acid residues or N-propionyl sialic acid residues.

In other embodiments, the vaccine composition comprise an isolated alpha (2→8) or (2→9) oligosialic acid derivative having (i) a degree of polymerization of about 2-20, (ii) a de-N-acetyl sialic acid content of about 50% to 98%, and (iii) a non-reducing end de-N-acetyl residue that is resistant to degradation by exoneuraminidase. In this particular embodiment, the oligosialic acid derivative is generally composed essentially of a mixture of N-acetyl sialic acid and de-N-acetyl sialic acid residues. A featured aspect of this embodiment it where the oligosialic acid derivative has a de-N-acetyl sialic acid content of about 88% to 98%, usually about 95% to about 98%.

The vaccine compositions of specific interest include those where the oligosialic acid derivative has a degree of polymerization of about 2-10, about 2-6, or less, and subranges thereof of dimer, trimer and tetramer. In some embodiments, the vaccine compositions are composed of essentially a single species of oligosialic acid derivative, for example, dimer, trimer or tetramer.

The vaccine compositions of the present disclosure may further include a conjugate of an oligosialic acid derivative as disclosed herein. Of specific interest is an oligosialic acid derivative conjugated to a second molecule that is an immunomodulator. In particular embodiments, the immunomodulator is a toxin or derivative thereof, such as tetanus toxoid. Examples of tetanus toxoid conjugate vaccine compositions of specific interest are those selected from NPrSia-TT, DeNAc-TT, OS-TT, and TcAc-TT, as described in the experimental examples, and derivatives thereof in which a single species of the oligosialic acid derivative is provided, for example, dimer, trimer or tetramer.

As summarized above, the disclosure provides methods of producing the alpha (2→8) and alpha (2→9) oligosialic acid derivatives disclosed herein. One feature of the methods is the use of sodium borohydride in a reduction reaction to generate an alpha (2→8) or (2→9) oligosialic acid derivative bearing a reducing end enriched for de-N-acetyl residues. This method involves (i) treating an alpha (2→8) or (2→9) oligosialic acid precursor having a reducing end and a non-reducing end with sodium borohydride under conditions for de-N-acetylating the non-reducing end, and (ii) isolating alpha (2→8) or (2→9) oligosialic acid derivative having one or more de-N-acetylated residues and a non-reducing end that is resistant to degradation by exoneuraminidase. A composition of particular interest that is generated by this method includes an isolated alpha (2→8) or (2→9) oligosialic acid derivative having (i) a degree of polymerization of about 2-20, and (ii) a non-reducing end that is enriched for de-N-acetyl residues and resistant to degradation by exoneuraminidase.

The sodium borohydride reduction reaction can be adjusted to generate oligosialic acid product with variable degrees of de-N-acetylation and sialic acid content. The reduction reaction is usually carried out in aqueous solution with the pH around or above pH 8. Most typically the reaction is allowed to proceed at a pH above 9, usually about 9 to 11, and most typically around 10. When the reaction is carried out around 10, the de-N-acetylation appears to be preferential for the non-reducing end of the sialic acid precursor material. The pH also can be adjusted or allowed to rise over the course of the reaction. In this embodiment the pH of the initial reaction conditions can be about 8, and the pH may be adjusted or allowed to generally rise over the course of the reaction to about 10.

Duration of the sodium borohydride reaction and temperature are useful variables for adjusting the desired conditions. For example, a sialic acid precursor material such as oligosialic acid can be admixed with sodium borohydride and water and left at a suitable temperature (e.g., ambient) and period of time (e.g., overnight) until the reaction reaches its desired endpoint (e.g., oligosialic acid derivative having a reducing end that is enriched for de-N-acetyl residues and resistant to degradation by exoneuraminidase).

The reaction mixture can then be purified by standard methods (e.g., dialysis in water and lyophilized followed by ion exchange) so as to isolate the desired material from byproduct, side reactions and the like, for analysis, storage, formulation, further modification and/or immediate use. For example, the amount of sialic acid and de-N-acetyl sialic acid in the oligosialic acid product may be determined (e.g., by resorcinol assay, such as described in the Examples), and/or tested for its ability to inhibit binding of an antibody such as SEAM 2, SEAM 3 and/or DA2 to a target antigen by inhibition ELISA, such as described below, for characterization, determination of IC50, and release purposes and the like.

A feature of the sodium borohydride reaction carried out on oligosialic acid precursor material is the majority (e.g., essentially all) of the oligosialic acid derivative generated by the method contains both sialic acid and de-N-acetyl sialic acid, as opposed to only de-N-acetylated material. Another feature of the sodium borohydride reaction with oligosialic acid precursor is that the de-N-acetylation reaction may occur selectively at the non-reducing end. For instance, treatment of the reaction product with excess amounts of an exoneuraminidase does not decrease the amount of oligosialic acid derivative, nor does it affect the ability of the oligosialic acid derivative to inhibit SEAM 3 binding to N-propionyl NmB polysialic acid.

Thus in another embodiment, the sodium borohydride de-N-acetylation reaction itself can be exploited to enrich for alpha (2→8) or (2→9) oligosialic acid derivative having a non-reducing end that is resistant to degradation by exoneuraminidase. This includes a specific embodiment in which the method is exploited to produce an alpha (2→8) or (2→9) oligosialic acid having a non-reducing end that is a de-N-acetylated residue, such as a neuraminic acid residue. The present disclosure thus provides both alpha (2→8) or (2→9) oligosialic acid derivatives that are enriched for de-N-acetylation at a non-reducing end, as well as compositions containing alpha (2→8) or (2→9) oligosialic acid derivatives, which compositions are enriched for alpha (2→8) or (2→9) oligosialic acid derivatives having a de-N-acetylated residue at the non-reducing end.

In another aspect, the sodium borohydride reaction is capable of generating a non-reducing end of an oligosialic acid derivative that is in a complex with boron. As sodium borohydride is a strong reducing agent, the reduction reaction may also be used to generate material in which the reducing end of the oligosialic acid derivative is reduced. In each instance, the desired material can be readily characterized by its ability to inhibit SEAM 2, SEAM 3 and/or DA2 3 binding to N-propionyl NmB polysialic acid. In other embodiments, the desired material is characterized by de-N-acetyl residue content. In certain embodiments, the desired material is characterized by one or more of antibody inhibition, de-N-acetyl residue content, N-acetyl residue content, degree of polymerization, purity, complement-mediated deposition, bacterial lysis, and reduction of cell viability, such as described in the experimental examples herein. And the compositions of the present disclosure may include these embodiments.

While the sodium borohydride method of the present disclosure can be optimally applied to generate oligosialic acid derivatives, the method may optionally include the additional step of enriching for oligo or polysialic acid derivative having a non-reducing end that is resistant to degradation by exoneuraminidase. The additional enriching step can be carried out by various purification methods, but advantageously by treatment with exoneuraminidase followed by isolation of material that is resistant to exoneuraminidase degradation, so as to simplify the process and improve step yield and product quality. This aspect can facilitate further extension of the method in the generation of de-N-acetylated product of increasingly longer chain length while retaining a desired attribute of the end product, namely, oligosialic acid derivative bearing a non-reducing end that is enriched for de-N-acetyl residues and resistant to degradation by exoneuraminidase.

In another embodiment, the sodium borohydride method also finds use in generating product that is comprised as an isolated mixture of alpha (2→8) or (2→9) oligosialic acid chains. For instance, when the reaction employs a precursor material that is polydisperse, such as an acid hydrolysis product of colominic acid, the end product is typically polydisperse. Thus in one embodiment, the oligosialic acid derivative is derived or obtainable from a precursor material which is itself derived or obtainable from colominic acid or the acid hydrolysis product of colominic acid.

The mixtures also may have varying degrees of polymerization. Examples include oligosialic acid derivatives having a degree of polymerization ranging from 2, 3, 4, 5, 6, 7, 8, 9, 10, 11, 12, 13, 14, 15, 16, 17, 18, 19, 20 and above, including 20 to 25, 25 to 30, 35 to 50, 50 to 75, 75 to 100, and 100 to 200 and above, depending on the oligosialic acid precursor material employed in the sodium borohydride reaction. Of specific interest are oligo and polysialic acid derivatives (and the compositions of the present disclosure that contain them) that include a degree of polymerization ranging from 2 to 200, with the degree of polymerization of oligosialic acid derivative of particular interest being from about 2 to 75, 2 to 70, 2 to 65, 2 to 60, 2 to 55, 2 to 50, 2 to 45, 2 to 40, 2 to 35, 2 to 30, 2 to 25, and more specifically 2 to 20. A particular embodiment is an oligosialic acid derivative with a degree of polymerization that is a positive integer ranging from about 2 to 20, as well as sub-ranges. For instance, the degree of polymerization for oligosialic acid derivative can be about 2 to 6, 4 to 8, 6 to 10, 8 to 12, 10 to 14, 12 to 16, and about 14 to 20. In a specific example, the degree of polymerization is in a range selected from about 4 to 6, 5 to 7, 6 to 9, 7 to 10, 8 to 11, 9 to 12, 10 to 13, 11 to 15, 12 to 18 and 13 to 20. In other embodiments, the degree of polymerization can be within or overlapping with the above ranges. As noted above, the degree of polymerization can be adjusted by selection of the precursor material used in the sodium borohydride reaction, as well as downstream purification by various chromatography techniques know in the art (e.g., dialysis, high performance liquid chromatography, affinity chromatography, size exclusion chromatography, ion exchange etc.).

As noted above, the oligosialic acid material generated from the sodium borohydride reaction will contain both sialic acid and de-N-acetyl sialic acid, and the ratio of sialic acid and de-N-acetyl sialic acid can vary depending on chain length. By way of example, a typical ratio for short oligosialic acid derivatives ranges from roughly 3:1 to 10:1 or more for the longer oligosialic acids. Thus the oligosialic acid derivatives include those having a sialic acid to de-N-acetyl sialic acid ratio of 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 and 20:1. Specific oligosialic acid derivatives of interest have a sialic acid to de-N-acetyl sialic acid ratio of 2:1, 3:1, 4:1, 5:1, 6:1, 7:1, 8:1, 9:1, 10:1, 11:1, 12:1, 13:1, 14:1 and 15:1, with those having a ration of 3:1, 4:1, 5:1, 6:1, 7:1, 8:1, 9:1 and 10:1 being of particular interest. Thus in one embodiment, the method generates, and thus compositions of the present disclosure include, a mixture of alpha (2→8) or (2→9) oligosialic acid chains that contains shorter length chains and a ratio of sialic acid to de-N-acetylated sialic acid of about 3:1. In another related embodiment, the desired product is a mixture of alpha (2→8) or (2→9) oligosialic acid chains that contains longer length chains and a ratio of sialic acid to de-N-acetylated sialic acid of about 10:1. Specific examples are shorter length chains that have a degree of polymerization ranging from about 2 to 6. Another example relates to longer length chains that comprise a degree of polymerization ranging from about 15 to 20. Yet another example is a mixture of alpha (2→8) or (2→9) oligosialic acid chains that comprise medium length chains having a degree of polymerization of about 6 to 15.

In some embodiments, production of an isolated oligosialic acid derivative involves: (i) providing a first composition comprising de-N-acetylated oligosialic acid; (ii) re-N-acylating the de-N-acetylated oligosialic acid to generate a second composition comprising partially re-acylated oligosialic acid having a mixture of N-acyl and de-N-acetyl residues; and then (iii) isolating from the second composition oligosialic acid derivative resistant to degradation by exoneuraminidase. In this embodiment, the re-acylation may be carried out with anhydrides, halogen functionalized, or otherwise activated acyl derivatives for coupling to the free amine of the partially de-N-acetylated oligosialic acid material. In another method, production of an isolated oligosialic acid derivative involves: (i) providing a first composition comprising polysialic acid precursor; (ii) partially de-N-acetylating the first composition to generate a second composition comprising partially de-N-acylated oligosialic acid having a mixture of N-acyl and de-N-acetyl residues, and then (ii) isolating from the second composition oligosialic acid derivative resistant to degradation by exoneuraminidase.

Oligosialic acid precursors of particular interest are homopolymers, such as a homopolymer of sialic acid, for example, colominic acid, and can be derived from natural sources or synthetic. In another embodiment, the polysialic acid precursors can be obtained from polysialic acid materials of *Escherichia coli* K1, *Escherichia Coli* K92, *Neisseria meningitidis* Serogroup B, *Neisseria meningitidis* Serogroup C, *Haemophilus ducreyi, Campylobacter jejuni, Moraxella catarrhalis, Streptococcus algalactiae,* and *Paterurella multocidae*. Additional suitable polysialic acid materials may be employed (Troy, F., *Sialobiology and the Polysialic Acid Glycotype: Occurrence, Structure, Function, Synthesis, and Glycopathology*, Chpt. 4, pp. 95-133, In Biology of Sialic Acids, Ed., Abrahman Rosenburg, Springer, 1995). Thus, depending on the precursor material selected, the N-acetyl and de-N-acetyl residues can be advantageously selected. For example, in one embodiment, the de-N-acetyl residue is neuraminic acid. In another embodiment the N-acetyl residue is sialic acid. In another embodiment, the polysialic acid derivative is a homopolymer of neuraminic acid and sialic acid. In other embodiments, the N-acetyl and/or de-N-acetyl neuraminic acid is O-acetylated at one or more positions, such as for a polysialic acid precursor obtained from polysialic acid of *N. meningitidis* Serogroup C in which C7 and C8 are O-acetylated in the naturally occurring material. In this regard, the present disclosure provides for control of the level of acylation of the final product, and in particular, the ability to generate oligosialic acid derivative that contains the desired mixture of residues.

This includes a related embodiment in which the polysialic acid precursor is selected so as to generate oligosialic acid derivative that contains about 10% to 98% de-N-acetyl residues, usually about 10% to about 60%, and in certain embodiments, about 1, 2, 3, 4 or 5 de-N-acetyl residues per oligosialic acid chain, and in specific embodiments, about 1 de-N-acetyl residues per oligosialic acid chain. Thus also contemplated herein are polysialic acid precursor selected so as to generate oligosialic acid derivative that contains a non-reducing end de-N-acetyl residue linked through a glycosidic bond to a residue selected from an N-acetyl residue and an N-acylated residue other than an N-acetyl group, and where the oligosialic acid derivative is substantially unoxidized and purified oligosaccharide having a degree of polymerization of about 2-10.

In a related embodiment, the polysialic acid precursor of the present disclosure can also be modified with various non-natural N-acyl groups. For instance, the polysialic acid precursor may re-N-acylated as noted above, or be the product of biosynthesis of a polysialic acid in cell culture where the growth media is supplemented with a mixture of mannosamine derivatives (e.g., N-trihaloacyl mannosamine) and acyl mannosamine (e.g., N-trihaloacetyl and N-acetyl mannosame) in a desired ratio such that the precursor material expressed by the cells contains the desired mixture of de-N-acetyl and N-acetyl residues, as well as the desired amount of non-natural N-acyl groups.

In the re-N-acylation step, partial re-N-acylation provides for production of a polysialic acid derivative having fewer than 90%, fewer than 85%, fewer than 84%, fewer than 80%, fewer than 75%, fewer than 70%, fewer than 60%, or fewer than 55%, usually about 10%, about 15%, about 16%, about 20%, about 25%, about 30%, about 40%, or about 45% N-acylated residues relative to the total residues of the compound. In this regard, the present disclosure provides for control of the level of acylation of the final product, so as to provide oligosialic acid derivative having a desired level of acylation. In general, reacylation is controlled or prevented by limiting the amount of acylating reagent. A particular embodiment of interest is oligosialic acid derivative having about about 1, 2, 3, 4 or 5 re-N-acylated residues per oligosialic acid chain, and in specific embodiments, about 1 re-N-acylated residues per oligosialic acid chain.

Other approaches are possible as well, including re-N-acylation with a mixture of amine protected group and acyl groups (e.g., trihaloacetyl and acetyl groups) in a desired ratio such that the polysialic acid derivative contains fewer than 90%, fewer than 85%, fewer than 84%, fewer than 80%, fewer than 75%, fewer than 70%, fewer than 60%, fewer than 55% amine protected residues, usually about 10%, about 15%, about 16%, about 20%, about 25%, about 30%, about 40%, or about 45% amine protected residues (e.g., N-trihaloacylated residues) relative to the total residues of the compound (where the compound generally contains at least 10 or at least 20 residues). In this regard, the present disclosure provides for control of the level of acylation of the final product after removal of the amine protecting group and avoiding undesirable side reactions with free amino groups, so as to provide a polysialic acid derivative having a desired level of acylation. Removal of the amine protecting groups for a free amine at the deprotected residue. In general, the proportion of de-N-acetyl residues is controlled by limiting the amount of amine protecting reagent (e.g., the amount of a trihaloacylting reagent). Here again, one embodiment of specific interest is the generation of oligosialic acid derivative containing the desired mixture of de-N-acetyl and N-acetyl residues, as well as the desired amount of non-natural N-acyl group as noted above.

In a specific embodiment, the first composition of the method of production is provided by treating a polysialic acid precursor with a strong reducing agent (e.g., sodium borohydride) in conjunction with or followed by a strong base (e.g., sodium hydroxide) under conditions suitable for de-N-acetylating the precursor.

The reaction mixture can then be purified by standard methods (e.g., dialysis in water and lyophilized followed by ion exchange) so as to isolate the desired material from byproduct, side reactions and the like. For example, the quality of the material and amount of particular residues in the oligosialic acid product may be determined at this point (e.g., by resorcinol assay, such as described in the Examples), and/or tested for its ability to be taken up and expressed as antigen on the surface of a cell, such as described below, for characterization, and release purposes and the like.

When coupled to the isolation of oligosialic acid derivatives resistant to degradation by exoneuraminidase, the products are enriched with the desired material and particularly well suited for increasing the antigen content on the surface of a cell. A composition of particular interest generated by this method includes an isolated oligosialic acid derivative having a non-reducing end that is enriched for de-N-acetyl residues and resistant to degradation by exoneuraminidase, as well as compositions that are enriched with mixtures of oligosialic acid derivatives having a non-reducing end enriched for de-N-acetyl residues.

For instance, the method of production step of isolating oligosialic acid derivative resistant to degradation by exoneuraminidase from the second composition typically involves exposing the partially re-acylated oligosialic acid to exoneuraminidase, and then purifying the desired oligosialic acid derivative. Exoneuraminidase of particular interest is an exosialidase from *Arthrobacter ureafaciens* (SIALIDASE A™, Prozyme, Hayward, Calif.). In this aspect, exoneuraminidase (exosialidase) cannot degrade polysialic acid that terminates on the non-reducing end with a de-N-acetyl sialic acid residue (i.e., neuraminic acid) or one that is otherwise chemically blocked. Therefore, digestion of a preparation of oligosialic acid derivative that contains de-N-acetyl residues located throughout the polymer with an exoneuraminidase will result in degradation of the polysialic acid except when the exoneuraminidase encounters a de-N-acetyl residue. At that point, no further degradation of the polymer will occur. Also, the oligosialic acid molecules that are not degraded are likely to have a de-N-acetyl sialic acid residue at the non-reducing end. Alternatively, the desired material can be isolated by standard purification of derivative under conditions that select for a terminal non-reducing end that is blocked from degradation by exoneuraminidase, such as a terminal neuraminic acid residue and the like.

Thus, in certain embodiments, the method of production can be used to directly produce a desired polysialic acid derivative resistant to degradation by exoneuraminidase from precursor material appropriate for this purpose. This method involves: (i) treating a first composition comprising oligosialic acid derivative having a mixture of N-acetyl and de-N-acetyl residues with exoneuraminidase; and (ii) isolating from the first composition oligosialic acid derivative resistant to degradation by the exoneuraminidase. This method is particularly suited when the precursor material is appropriately selected and/or prepared to contain a mixture of N-acetyl and de-N-acetyl residues, and then the desired product purified and isolated away from the degradation products so as to avoid unwanted side reactions such as re-acetylation, aldehyde and ketone side reactions, unwanted cross linking, as well as a wide range of other unwanted contaminants such as monomer and intermediates susceptible to exoneuraminidase degradation, or that otherwise alter the desired properties of the material.

In another specific embodiment, compositions of the present disclosure can be produced by (i) providing a solution comprising a mixture of oligosialic acid derivatives each having: a different degree of polymerization, a different mixture of N-acyl residues and de-N-acetyl residues, and a non-reducing end N-acetyl sialic acid residue; (ii) subjecting the solution to ion exchange chromatography to generate fractions; and (iii) isolating from one or more of the fractions oligosialic acid derivative having a defined degree of polymerization and a non-reducing end de-N-acetyl residue resistant to degradation by exoneuraminidase. In certain aspects, the mixture of oligosialic acid derivatives further includes oligosialic acid molecules having a non-reducing end N-acetyl group. In some embodiments, the oligosialic acid derivative having a defined degree of polymerization is isolated in an individual fraction, or a pool of fractions formed by pooling selected fractions containing a polysialic acid derivative having a desired activity of interest.

In particular embodiments, ion exchange chromatography is carried out at a pH of between about 6.5 and about 10.0. In a specific embodiment, the ion exchange chromatography is anion exchange chromatography. In some embodiments, the anion exchange chromatography is high pH anion-exchange chromatography (HPAC). In certain embodiments, the anion exchange chromatography utilizes DEAE, TMAE, QAE, or PEI. In other embodiments, the anion exchange chromatography utilizes TOYOPEARL SUPER Q® 650M, MONO Q®, SOURCE Q® or FRACTOGEL® TMAE. A particular ion exchange chromatography procedure of interest employs a resin such as Q Sepharose™Fast Flow (strong anion), SP Sepharose™Fast Flow (strong cation), CM Sepharose™Fast Flow (weak cation), DEAE Sepharose™Fast Flow (weak anion), and ANX Sepharose™4 Fast Flow (high sub) (weak anion) (e.g., available from GE Healthcare Bio-Sciences Corp., Piscataway, NJ). Of specific interest are strong anion exchangers, such as Q Sepharose™Fast Flow. Sample/loading buffer and elution system for such ion exchange columns and systems are generally selected for resolving the isolation of a particular compound of interest.

An example of a general buffer system for a Q Sepharose™ Fast Flow anion exchange resin is a sample/loading buffer system of 20 mM Bis-Tris buffer, pH 8, and an elution buffer system composed of a 0M to 0.2M gradient of sodium chloride in 20 mM Bis-Tris buffer, which can be eluted at different flow rates depending on column dimensions and the like. The ion exchange fractions containing a de-N-acetyl and N-acetyl sialic acid material of interest can be analyzed with great sensitivity by high pH anion-exchange chromatography with pulsed amperometric detection (HPAC-PAD)(e.g., Townsend, R. R. (1995) Analysis of glycoconjugates using high-pH anion-exchange chromatography. J. Chromatog. Library 58, 181-209; and Manzi et al., (1990) HPLC of sialic acids on a pellicular resin anion exchange column with pulsed amperometry. Anal. Biochem. 188, 20-32). The isolated material may be purified further by one or more orthogonal chromatography techniques such as gel permeation, size exclusion, RP-HPLC and the like. If desired, the isolated oligosialic acid material can be subjected to one or more of further preparatory steps, such dialysis, lyophilization, crystallization, formulation and the like.

The ion exchange and purification method described above can be carried out on a mixture of oligosialic acid derivative that is produced by treating a first composition comprising oligosialic acid derivative having a mixture of N-acetyl and de-N-acetyl residues with exoneuraminidase. The method may also be carried out on a mixture of re-acetylated oligosialic acid derivatives, such as produced by re-acylating a first composition comprising de-N-acetylated oligosialic acid to generate a second composition, the second composition comprising partially re-acylated oligosialic acid having: a mixture of N-acyl and de-N-acetyl residues, and which is resistant to degradation by exoneuraminidase.

In a particular embodiment of interest, the ion exchange and purification method described above is applied in the production and purification of isolated oligosialic acid derivative that is substantially unoxidized and defined so as to have few side products in the initial material subjected to ion exchange purification. For instance, unwanted oxidation of oligosialic acid generates multiple overlapping degradation and side reaction products that can be difficult to resolve and separate from the desired material by ion exchange chromatography. As such, "substantially unoxidized" is intended mean that the oligosialic acid derivative, excepting normal isomer or tautomer equilibriums, contains less than about 20%, less than about 15%, less than about 10%, less than about 5% oxidized saccharide residues, and usually about 80%, about 85%, about 90%, about 95% or greater unoxidized saccharide residues. Of specific interest is a total chemical synthesis method that generates an initial product containing few side reaction products, and facilitates the purification of smaller oligosialic acid derivatives of defined length and composition.

In certain embodiments, the substantially unoxidized and defined oligosialic acid derivative is produced by time-controlled de-N-acetylation and/or non-oxidizing acid hydrolysis of a oligosialic acid precursor material of interest. A featured aspect is a chemical synthesis method for the production of a substantially unoxidized and defined oligosialic acid derivative, where the method involves either (i) non-oxidizing acid hydrolysis of partially de-N-acetylated oligosialic acid prepared by reduced time-controlled alkaline hydrolysis, or (ii) partial de-N-acetylation of oligosialic acid by reduced time-controlled alkaline hydrolysis followed by non-oxidizing acid hydrolysis.

Partial de-N-acetylation of oligosialic acid by time-controlled alkaline hydrolysis involves (i) treating a oligosialic acid precursor with a strong reducing agent in a strong base under conditions suitable for partially de-N-acetylating the precursor, where the treating is for a period of time effective to generate a minimally degraded product of partially de-N-acetylated oligosialic acid. In certain embodiments, the period of time for treatment is about 1 hour or less, generally ranging from about 5-55 minutes in one minute increments, such as ranging from about 10-50 minutes, 15-45 minutes, 20-40 minutes, and usually about 40 minutes. Thus, the reaction time can be selected to provide for minimally degraded product, generating desired fractions of partially de-N-acetylated polysialic acid separatable by ion exchange chromatography. An example of a suitable strong reducing agent for this procedure is sodium borohydride, sodium cyanogen borohydride and the like (i.e., reagents that easily lose (or donate) electrons, such as in approximate increasing order of strength: sodium cyanogen borohydride~sodium triacetoxyborohydride, sodium borohydride, lithium tri-sec-butylborohydride, and lithium aluminum hydride). An example of a suitable strong base is sodium hydroxide (i.e., a base which hydrolyzes completely, raising the pH of the solution towards 14, and thus a base having a pKa of more than about 13, such as in approximate increasing order of strength: potassium hydroxide, barium hydroxide, cesium hydroxide, sodium hydroxide, strontium hydroxide, calcium hydroxide, lithium hydroxide, and rubidium hydroxide). The reaction may also be aided by selecting an appropriate temperature, usually ranging from about 70° C.-120° C., about 80° C.-110° C., and more typically about 90° C.-100° C. As such, alkaline de-N-acetylation can be carried out for different reaction times to generate de-N-acetyl polysialic acid containing defined amounts of de-N-acetyl sialic acid residues throughout the polymer precursor, and to generate discrete fractions with minimal overlapping degradation products. In addition, the time-controlled partial alkaline de-N-acetylation procedure can generate oligosialic acid derivative containing desired amounts of de-N-acetyl residues, for example, about 25%-60% de-N-acetyl residues.

Non-oxidizing acid hydrolysis can be carried out to increase the fraction of chains containing de-N-acetyl sialic acid at the non-reducing end, since the glycosidic bond at the reducing end of a de-N-acetyl sialic acid residue in oligosialic acid is resistant to hydrolysis while the bond at the non-reducing end of the residue is not. In addition, performing the acid hydrolysis reaction under such non-oxidizing conditions minimizes oxidative damage to the polysaccharide that can occur in the presence of strong acid or high concentrations (10%) of acetic acid. Furthermore, non-oxidizing acid hydrolysis facilitates the production of smaller oligosialic acid (or oligosaccharide) derivatives enriched for de-N-acetyl sialic acid residues at the non-reducing end. This aspect of the present disclosure involves (i) exposing a polysialic acid precursor or a partially de-N-acetylated polysialic acid under acidic conditions capable of selectively hydrolyzing a glycosidic bond of the polysialic acid, where the acidic conditions include a buffer solution in which dissolved gasses have been evacuated (e.g., by alternately freezing and thawing the solution under vacuum). Anti-oxidants and free radical scavengers may also be added to the reaction mixture to further reduce the oxidizing environment of the reaction solution. In addition to the non-oxidizing conditions, the acidic buffer system generally includes those suitable for acid-based polysialic acid hydrolysis reactions, for example, 0.1 M sodium acetate buffer, pH 5.5. Additional examples of acidic conditions include hydrochloric acid (e.g., 20 mM HCl) and trifluroacetic acid (e.g., 0.1 M TFA). The non-oxidizing acid hydrolysis reaction can be carried out for different periods of time, for a given end use, which is usually about 1-30 hours, 5-25 hours, 10-20 hours, and generally about 15-18 hrs. The temperature of the reaction may also be adjusted to aid control of the reaction. Examples of suitable a temperature range is about 25° C. or greater, such as a temperature of about 40° C. to 90° C., usually about 50° C. to 70° C. As such, the non-oxidizing acid hydrolysis method is well suited for generating shorter length oligosialic acid derivatives having a non-reducing end de-N-acetyl residue and a desired degree of polymerization, including for example, products with a defined degree of polymerization of about 2-20, usually of about 2-10.

Hence the products produced by the methods include certain features to generate product that is substantially free of contaminants, and thus enriched for the desired derivative relative to non-enriched controls. This includes oligosialic acid derivatives that have an increase in the proportion of a desirable property or element. For example, isolation of a desired oligosialic acid derivative is where the oligosialic acid of interest represents the majority of the desired material (e.g., more than 50%, 55%, 60%, 65%, 70%, 75%, 80%, 85%, 90%, 95% or more up to 100%). This of course includes mixtures of oligosialic acid derivatives having variable chain lengths, provided that the majority of chains each individually contain a mixture of de-N-acetyl and N-acyl residues and that is resistant to degradation to exoneuraminidase, as well as mixtures with these features and the additional feature of having a non-reducing end that is enriched for de-N-acetyl residues, including for instance a de-N-acetylated residue at the non-reducing terminal end (i.e., a non-reducing end de-N-acetyl sialic acid residue).

Again, depending of the specific approach, oligosialic acid derivative can be produced to have various beneficial structural and related functional properties, such as a non-reducing end having one or more de-N-acetyl residues, a terminal de-N-acetyl residue and the like. As noted above, a de-N-acetyl residue of specific interest is neuraminic acid, and thus the terminus of the non-reducing end can be neuraminic acid. As also noted above, the methods can be exploited to produce oligosialic acid derivative in which the non-reducing end is enriched with de-N-acetyl residues, as well as homopolymers of neuraminic and sialic acid and the like.

The production methods of present disclosure also feature additional products that can be produced or derived from the methods. In particular, the methods may further include the step of conjugating a second molecule. In this aspect, the isolated alpha (2→8) or (2→9) oligosialic acid derivative is conjugated to a second molecule, such as a protecting group, amino acid, peptide, polypeptide, lipid, carbohydrate, nucleic acid, detectable label and the like.

An advantage of oligosialic acid derivatives that are conjugated to another molecule includes the ability to retain the desired activity, while exploiting properties of the second molecule of the conjugate to impart an additional desired characteristic. For example, the oligosialic acid derivatives can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like. More specifically, the oligosialic acid derivatives described herein can be conjugated to a second molecule such as a peptide, polypeptide, dye, fluorophore, nucleic acid, carbohydrate, lipid and the like (e.g., at either the reducing or non-reducing end), such as the attachment of a lipid moiety, including N-fatty acyl groups such as N-lauroyl, N-oleoyl, fatty amines such as dodecyl amine, oleoyl amine, and the like (e.g., see U.S. Pat. No. 6,638,513)).

In a specific embodiment of the present disclosure, the conjugate modifies cellular uptake relative to unconjugated material. In a related embodiment, the oligosialic acid derivative conjugate increases cellular uptake relative to unconjugated material. In other embodiments, the conjugate decreases cellular uptake relative to unconjugated material. In this aspect, the efficiency of cellular uptake can be increased or decreased by linking to peptides or proteins that facilitate endocytosis. For example, a given oligosialic acid derivative can be linked to a ligand for a target receptor or large molecule that is more easily engulfed by endocytotic mechanisms, such as an antibody. The antibody or other ligand can then be internalized by endocytosis and the payload released by acid hydrolysis or enzymatic activity when the endocytotic vesicle fuses with lysosomes. As such, the conjugate may be one that increases endocytosis relative to unconjugated oligosialic acid derivative. To decrease cellular uptake, the conjugate can include a ligand that retains the oligosialic acid derivative on the surface of a cell, which can be useful as a control for cellular uptake, or in some instances decrease uptake in one cell type while increasing it in others.

Other features of the conjugates can include one where the conjugate reduces toxicity relative to unconjugated oligosialic acid derivative. In further embodiments, the conjugate targets a cancer cell relative to unconjugated material. Additional examples include a conjugate the oligosialic acid derivative with one or more molecules that complement, potentiate, enhance or can otherwise operate synergistically in connection with the oligosialic acid derivative. For instance, the oligosialic acid derivative can optionally have attached an anti-cancer drug for delivery to a site of a cancer cell to further facilitate tumor killing or clearance, e.g., an anti-proliferation moiety (e.g., VEGF antagonist, e.g., an anti-VEGF antibody), a toxin (e.g., an anti-cancer toxin, e.g., ricin, *Pseudomonas* exotoxin A, and the like), radionuclide (e.g. 90Y, 131I, 177L, 10B for boron neutron capture, and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

The oligosialic acid and conjugate compositions also include alpha (2→8) or (2→9) oligosialic acid derivatives having one or more re-N-acylated residues. For example, a re-N-acylated residue of specific interest comprises an amino protecting group. Exemplary amino protecting groups for use include, but are not necessarily limited to, carbamates, amides, N-alkyl and N-aryl amines, imine derivatives, enamine derivatives, N-sulfonyls, and the like. Further exemplary amine protecting groups include, but are not necessarily limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. In some embodiments, the re-acylated residues include an N-substituted group such as acryl, methacryl, haloacetyl, propionyl, methanesulfonyl, di and trihalo acetyl and the like. Re-acylated residues having an N-substituted group may therefore include a trihaloacyl group, such as trihaloacetyl and trihalopropionyl groups (e.g., trichloroacetyl, trifluoroacetyl, trichloropriopionyl, trifluoropriopionyl), and the like. Re-acylated residues having an N-substituted trihaloacetyl or proprionyl group are of specific interest, with trichloroacetyl groups being of particular interest.

A particular embodiment of interest is where the second molecule is an immunomodulator. By "immunomodulator" is intended a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid. Another embodiment includes an oligosialic acid derivative composition that contains one or more immunogenic excipients; in this embodiment, the oligosialic acid derivative can be conjugated or not. Nevertheless, a particular feature of the oligosialic acid derivative is that it is capable of inhibiting SEAM 2, SEAM 3 and/or DA2 binding to N-propionyl NmB polysialic acid.

Other examples include pharmaceutical compositions for use as vaccines, anti-cancer therapeutics that contain an oligosialic acid derivative of the present disclosure, as well as use of the derivatives for the generation of antibodies and the like. Compositions of particular interest include an antibody specific for an alpha (2→8) or (2→9) oligosialic acid derivative produced according to the sodium borohydride method discussed above. The antibody is capable of complement mediated bacteriolysis and opsonophagocytosis of *Neisseria meningitidis* group B (NmB) bacteria. Of particular interest are antibodies capable of binding neuraminic acid-containing antigens expressed by dividing or non-dividing Jurkat T-cell leukemia cells. An advantage of binding non-dividing and dividing cells is that the antibody can bind to non-dividing Jurkat T-cell leukemia cells better than SEAM 3. The antibodies can be polyclonal or monoclonal, and be of an animal (e.g., mouse), human or humanized, as well as fragments thereof. The antibodies of the present disclosure may also be conjugated, such as described above for the oligosialic acid derivatives.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification. A particular embodiment of interest is an isolated antibody specific for an alpha (2→8) or (2→9) oligosialic acid derivative that comprises a non-reducing end enriched for one or more de-N-acetylated residues and is resistant to degradation by exoneuraminidase. Examples include an antibody is capable of complement mediated bacteriolysis and opsonophagocytosis of *Neisseria meningitidis* group B (NmB) and group C (NmC) bacteria. Additional examples in clued an isolated antibody capable of binding neuraminic acid-containing antigens expressed by dividing or non-dividing Jurkat T-cell leukemia cells. In certain embodiments, the isolated antibody binds the non-dividing Jurkat T-cell leukemia cells better than SEAM 3. In embodiments, the isolated antibody is mouse. In a specific embodiment, the isolated antibody is specific for non-reducing end de-N-acetyl sialic acid residue. A featured aspect is a monoclonal antibody having a CDR polypeptide sequence selected from a CDR polypeptide sequence depicted in FIG. 19 or 20. A specific embodiment is monoclonal antibody DA2 having a light and heavy chain complementarity determining region (CDR) polypeptide sequence as depicted in FIGS. 19 and 20.

In other embodiments, the monoclonal antibody is a humanized monoclonal antibody. For instance, chimeric antibodies may also be provided, especially if the antibodies are to be used in preventive or therapeutic pharmaceutical preparations. Chimeric antibodies composed of human and non-human amino acid sequences may be formed from the mouse monoclonal antibody molecules to reduce their immunogenicity in humans by standard techniques known in the art.

Antibody fragments (e.g., such as F(ab')2, FV, and sFv molecules) may also be provided that are capable of exhibiting immunological binding properties of the parent monoclonal antibody molecule can be produced using known techniques as well. For instance, a phage-display system can be used to expand the monoclonal antibody molecule populations in vitro. Once generated, the phage display library can be used to improve the immunological binding affinity of the Fab molecules using known techniques. The coding sequences for the heavy and light chain portions of the Fab molecules selected from the phage display library can be isolated or synthesized, and cloned into any suitable vector for expression (e.g, bacterial, yeast, insect, amphibian and mammalian vector systems).

Compositions of specific interest, including pharmaceutical formulations, include those comprising an aggregate of a alpha (2→8) or (2→9) oligosialic acid derivative, including an aggregate of individual or a mixture of different alpha (2→8) or (2→9) oligosialic acid derivatives, and capable of being taken up by cells and expressed on the cell surface better than the corresponding non-aggregated derivative, for example, as gauged by the amount of the alpha (2→8) or (2→9) oligosialic acid derivative present on the cell surface relative to the appropriate control.

The aggregates can be molecular aggregates or microscopic aggregates. Aggregates of specific interest are particles, such as a microscopic particle. This includes an aggregate that is capable of being more readily taken up by the cell and expressed on the cell surface compared to the corresponding non-aggregated derivative. By "corresponding non-aggregated derivative" is intended the same derivative found in the aggregate in reference.

Another embodiment is a method of producing a composition comprising an aggregate of one or more an alpha (2→8) or (2→9) oligosialic acid derivatives, as well as the compositions produced by the methods. This method involves exposing an alpha (2→8) or (2→9) oligosialic acid derivative to an aggregating condition so as to form an aggregate. Thus the methods of production described above may further include the step of forming an aggregate of the isolated alpha (2→8) or (2→9) oligosialic acid derivative. Examples of the aggregating conditions include heating, addition of an excipient that facilitates aggregation, and the like.

By "aggregate" is intended a particle comprising an aggregated complex of individual monomers of a molecule and having a combined molecular weight that is a multiple of the molecular weight of an individual monomer of the complex. For example, an aggregate of one or more monomers of an alpha (2→8) or (2→9) oligosialic acid derivative include an aggregate complex having a particle molecular weight that is 10× or more of the molecular weight of an individual monomer in the aggregated monomer complex. This includes an aggregate having a particle with a molecular weight of greater than about 50,000, to greater than about 250,000 Daltons, to greater than 500,000 Daltons, to greater than 750,000 Daltons, to greater than 1,000,000 Daltons up to a particle having a uniform particle size that is readily visible by light microscopy, e.g., under a standard low magnification light microscope (e.g., 40× magnification).

Thus, the aggregate can be a molecular or microscopic particle. For microscopic particles, the optimal aggregate can be selected by varying the mean aggregate diameter, e.g., 1 um to 20 μm, and usually about or smaller than the diameter of a cell targeted for exposure and uptake of the material of interest, e.g., cells are usually approximately 1-20 μm in diameter. For non-visible molecular particles, as well as the microscopic particles, the desired aggregate can be selected by measuring uptake and internalized by cells. In each instance, the aggregate of the alpha (2→8) or (2→9) oligosialic acid derivative is capable of being taken up and internalized by cells better than non-aggregated derivative relative to each other, a control, and/or both.

As noted above, the aggregate can be formed by admixing a non-aggregated forms of one or more alpha (2→8) or (2→9) oligosialic acid derivatives under aggregating conditions, by partial degradation or partial hydrolysis of a alpha (2→8) or (2→9) oligosialic acid derivative under aggregating conditions, forming an aggregate of the alpha (2→8) or (2→9) oligosialic acid derivative with an aggregating excipient, or a combination thereof. By "aggregating condition" is intended chemical-physical conditions that cause an otherwise soluble material to form an aggregated substance in solution. For instance, a alpha (2→8) or (2→9) oligosialic acid derivative can be heated (e.g., 30° C.-70° C.) for an appropriate period of time (e.g., 1 hr to overnight) so as to form an aggregate. Typically, the temperature and duration of exposure are selected to reduce or inhibit microbial growth (e.g., reduce the potential for contamination) while not destroying the desired activity of the aggregate.

In another embodiment, the alpha (2→8) or (2→9) oligosialic acid derivative comprises a non-reducing end that is a de-N-acetyl residue, such as neuraminic acid, and the aggregate is formed by exposing the derivative to aggregating conditions. The sodium borohydride method described above and/or treatment with exoneuraminidase enriches for non-reducing end de-N-acetyl residues which aggregate when heated forming particles that are readily taken up by cells. This also applies to other alpha (2→8) or (2→9) oligosialic of sialic acid, including non-derivatized alpha (2→8) or (2→9) oligosialic acid as well as derivatized alpha (2→8) or (2→9) oligosialic acid.

Thus the present disclosure also provides a method of producing an aggregate of an alpha (2→8) or (2→9) oligosialic acid or alpha (2→8) or (2→9) oligosialic acid derivative. This method involves exposing an alpha (2→8) or (2→9) oligosialic acid or an alpha (2→8) or (2→9) oligosialic acid derivative having a non-reducing end that is resistant to degradation by exoneuraminidase to aggregating conditions, and isolating the aggregate.

In another embodiment, the aggregate of an alpha (2→8) or (2→9) oligosialic acid derivative is formed by the addition of one or more excipients capable of facilitating aggregation of the derivative. Of particular interest are substances capable of facilitating aggregation such as aluminum hydroxide.

Accordingly, the present disclosure further provides various methods for use of the compositions of the disclosed herein. One feature of the methods is that the oligosialic acid derivatives of the present disclosure find particular use in eliciting antibodies that can be useful in inhibiting the growth of cancerous cells in a subject. This method involves administering to the subject an effective amount of a pharmaceutically acceptable formulation that comprises an antibody specific for an alpha (2→8) or (2→9) oligosialic acid derivative bearing a reducing end enriched for de-N-acetyl residues and resistant to degradation by exoneuraminidase. In this embodiment, the administering facilitates reduction in viability of cancerous cells exposed to the antibody.

Another embodiment is a method of eliciting antibodies to a cancerous cell in a subject that bears a de-N-acetylated sialic acid (deNAc SA) epitope. This method involves administering to a subject an immunogenic composition comprising an isolated alpha (2→8) or (2→9) oligosialic acid derivative bearing a non-reducing end enriched for de-N-acetyl residues and resistant to degradation by exoneuraminidase, where the administering is effective to elicit production of an antibody that specifically binds to a deNAc SA epitope of the cancerous cell.

Another embodiment is a method of eliciting antibodies to bacteria that bear a de-N-acetylated sialic acid (deNAc SA) epitope, such as those found on polysaccharide capsules of *Neisseria* (e.g., *N. meningitidis*, particularly *N. meningitidis* Groups B and C) and *E. coli* K1. This method involves administering to a subject an immunogenic composition comprising an isolated alpha (2→8) or (2→9) oligosialic acid derivative bearing a reducing end enriched for de-N-acetyl residues and resistant to degradation by exoneuraminidase, where the administering is effective to elicit production of an antibody that specifically binds to a deNAc SA epitope of a bacteria.

By a "deNAc SA epitope" is intended a molecule that has (i) maximal cross-reactivity with an antibody against polysialic acid in which one or more residues is a de-N-acetyl neuraminic acid residue, and (ii) has minimal to no cross-reactivity with an antibody against normal polysialic acid, especially as presented on a non-cancerous mammalian, e.g., human, cell surface. Thus in certain embodiments the minimal deNAc SA epitope is a disaccharide of sialic acid residues in which one or both residues contain a free amine at the C5 amino position; when one of the two residues is de-N-acetylated, the second residue contains an N-acetyl group (but, in some embodiments, not an N-propionyl group). The disaccharide unit defining this minimal epitope may be at the reducing end, the non-reducing end, or within a polymer of sialic acid residues (e.g., within a polysaccharide). De-N-acetylated residues in the context of polysialic acid (PSA) containing N-acylated residues are immunogenic and elicit antibodies that are reactive with the deNAc SA epitope, but are minimally reactive or not detectably reactive with human PSA antigens. For example, the de-N-acetylated NmB polysaccharide epitope was identified using a murine anti-N-propionyl *Neisseria meningitidis* group B (N-Pr NmB) polysaccharide mAb (monoclonal antibodies), SEAM 3, described in Granoff et al., 1998, J Immunol 160:5028 (anti-N-Pr NmB PS mAbs); U.S. Pat. No. 6,048,527 (anti-NmB antibodies); and U.S. Pat. No. 6,350,449 (anti-NmB antibodies).

In the methods of treatment of cancer, administering of the antibody specific for an alpha (2→8) or (2→9) oligosialic acid derivative, or an immunogenic composition that includes such derivative facilitates a reduction in viability of cancerous cells exposed to the antibody and/or oligosialic acid derivative. Advantages of these methods are that the antibody generated by administration of alpha (2→8) or (2→9) oligosialic acid derivatives can be directly or indirectly cytotoxic to cancer cells containing a deNAc SA epitope. Thus can have the effect of retarding or otherwise arresting cell growth, and even inducing apoptosis, leading to cell death. Another advantage is that the cytotoxicity of the antibody can be dose dependent, and thus adjustable. Specific examples of cancerous cells amenable to treatment by the methods include melanoma, leukemia, or neuroblastoma.

In a related embodiment, the subject being treated possesses a deNAc SA epitope. The epitope can be present inside a cell or expressed on the cell surface, such as a cancer cell or a bacteria. This aspect can be beneficial in the context of the methods of the present disclosure in that cells expressing or presenting a deNAc SA epitope can be more amenable to treatment with an antibody and/or oligosialic acid derivative of the present disclosure. Of course the antibody and/or oligosialic acid derivative can be administered to a subject that is naïve with respect to the deNAc SA epitope, for example, where therapy is initiated at a point where presence of the epitope is not detectable, and thus is not intended to be limiting. It is also possible to initiate antibody and/or oligosialic acid derivative therapy prior to the first sign of disease symptoms, at the first sign of possible disease, or prior to or after diagnosis of a primary cancer and/or metastases of a cancer having a detectable deNAc SA epitope (e.g., a ganglioside or other glycoconjugate that is at least partially de-N-acetylated).

Another embodiment involves screening for the deNAc SA epitope in combination with antibody and/or oligosialic acid derivative therapy. In this method, cells from a subject undergoing treatment, or being tested for susceptibility to treatment, with antibody and/or oligosialic acid derivative are screened for the presence of a deNAc SA epitope. This can be accomplished using an antibody or antibody fragment that binds to the epitope (e.g., an antibody specific for an oligosialic acid derivative of the present disclosure, or a SEAM 3 monoclonal antibody (ATCC Deposit No. HB-12170)). Of particular interest is the monoclonal antibody DA2 or an antibody with similar activity against non-reducing end de-N-acetyl sialic acid residues. As with cancer therapies in general, an advantage of this approach is the ability to select individuals with a cellular proliferation disorder or stage of disorder likely to be more responsive to antibody and/or oligosialic acid derivative therapy compared to those that are not. Another advantage of targeting a subject with cells bearing a deNAc SA epitope is that progress over the treatment course can be monitored, and therapy, including dosing regimens, amounts and the like can be adjusted accordingly.

In practicing the methods, routes of administration (path by which the antibody and/or oligosialic acid derivative is brought into contact with the body) may vary, where representative routes of administration for the oligosialic acid derivative are described in greater detail below. In certain embodiments, the oligosialic acid derivative is administered by infusion or by local injection. It also can be administered prior, at the time of, or after other therapeutic interventions, such as surgical intervention to remove cancerous cells. The antibody and/or oligosialic acid derivative can also be administered as part of a combination therapy, in which at least one of an immunotherapy, a cancer chemotherapy or a radiation therapy is administered to the subject (as described in greater detail below).

In the methods, an effective amount of an antibody and/or oligosialic acid derivative is administered to a subject in need thereof. In particular, antibody and/or oligosialic acid derivatives of specific interest are those that inhibit growth of a cancer cell in a host when the compounds are administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the antibody and/or oligosialic acid derivative composition, the treating clinician's assessment of the medical situation, and other relevant factors. It is expected that the amount will fall in a relatively broad range that can be determined through routine trials. For example, the amount of antibody and/or oligosialic acid derivative employed to inhibit cancer cell growth is not more than about the amount that could otherwise be irreversibly toxic to the subject (i.e., maximum tolerated dose). In other cases the amount is around or even well below the toxic threshold, but still in an immunoeffective concentration range, or even as low as threshold dose. In embodiments involving use of the alpha (2→8) or (2→9) oligosialic acid derivatives to elicit an immunoprotective and/or immunotherapeutic immune response against a cancer cell and/or a bacterial infection (e.g., *Neisseria* and/or *E. coli* K1), the amount of alpha (2→8) or (2→9) oligosialic acid derivative administered is an amount effective to elicit an immunoprotective or immunotherapeutic immune response in the subject against a cancer cell and/or bacterial infection, where amount to effect such immune response may vary according to a variety of subject—specific factors, such as those exemplified above. Where the alpha (2→8) or (2→9) oligosialic acid derivative is administered to effect an anti-deNAc SA antibody response, the antibodies elicited can provide for specific binding of deNAc SA epitopes on a target antigen with little or no detectable binding to host-derived polysialic acid.

Individual doses are typically not less than an amount required to produce a measurable effect on the subject, and may be determined based on the pharmacokinetics and pharmacology for absorption, distribution, metabolism, and excretion ("ADME") of the antibody and/or oligosialic acid derivative, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the antibody is typically via injection and often intravenous, intramuscular, intratumoral, or a combination thereof.

Disposition of the antibody and/or oligosialic acid derivative and its corresponding biological activity within a subject is typically gauged against the fraction of antibody and/or oligosialic acid derivative present at a target of interest. For example, an oligosialic acid derivative once administered can accumulate as a component of polysialic acid, a glycoconjugate or other biological target that concentrates the material in cancer cells and cancerous tissue. Thus dosing regimens in which the antibody and/or oligosialic acid derivative is administered so as to accumulate in a target of interest over time can be part of a strategy to allow for lower individual doses. This can also mean that, for example, the dose of antibody that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC50 of a given antibody and/or oligosialic acid derivative for inhibiting binding of SEAM 2, SEAM 3 and/or DA2, such as described in the SEAM 3 Inhibition Assay described herein. By "IC50" is intended the concentration of a drug required for 50% inhibition in vitro. Alternatively, the effective amount can be gauged from the EC50 of a given oligosialic acid derivative. By "EC50" is intended the plasma concentration required for obtaining 50% of a maximum effect in vivo.

In general, with respect to the antibody and/or oligosialic acid derivatives of the present disclosure, an effective amount is usually not more than 200× the calculated IC50. Typically, the amount of an antibody and/or oligosialic acid derivative that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

In other embodiments, an effect amount is not more than 100× the calculated EC50. For instance, the amount of antibody and/or oligosialic acid derivative that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays such as those described herein and illustrated in the Experimental section, below.

In a specific embodiment, the IC50 is calculated by inhibiting antibody binding in vitro. This aspect can be carried out by assessing the ability of an oligosialic acid derivative of interest to inhibit SEAM 2, SEAM 3 and/or DA2 antibody binding to dodecylamine N-propionyl NmB polysialic acid or N-propionyl NmB polysialic acid, such as described in the experimental examples for inhibition of SEAM 3 binding by dodecylamine N-propionyl NmB polysialic acid. In general, the procedure is carried out by standard ELISA in which the plates are coated with dodecylamine N-propionyl NmB polysialic acid or N-propionyl NmB polysialic acid as described in the examples at a concentration of about 10 μg/ml, and then processed and employed as described in the experimental examples to determine inhibition of antibody binding and the IC50. These antibodies and others suitable for various aspects of this purpose can be employed (e.g., SEAM-2 (ATCC Deposit No. CRL-12380), SEAM 3 (ATCC Deposit No. HB-12170), SEAM-18 (ATCC Deposit No. HB-12169), and SEAM-12 (ATCC Deposit No. CRL-12381).

As noted above, another feature of the methods is that the antibody and/or oligosialic acid derivative can be administered to the subject in combination with one or more other therapies. For example, a therapy or treatment other than administration of antibody and/or oligosialic acid derivative composition can be administered anywhere from simultaneously to up to 5 hours or more, e.g., 10 hours, 15 hours, 20 hours or more, prior to or after the oligosialic acid derivative. In certain embodiments, the antibody and/or oligosialic acid derivative and other therapeutic intervention are administered or applied sequentially, e.g., where the antibody and/or oligosialic acid derivative is administered before or after another therapeutic treatment. In yet other embodiments, the antibody and/or oligosialic acid derivative and other therapy are administered simultaneously, e.g., where the antibody and/or oligosialic acid derivative and a second therapy are administered at the same time, e.g., when the second therapy is a drug it can be administered along with the antibody and/or oligosialic acid derivative as two separate formulations or combined into a single composition that is administered to the subject. Regardless of whether administered sequentially or simultaneously, as illustrated above, the treatments are considered to be administered together or in combination for purposes of the present disclosure.

Antibody and/or oligosialic acid derivatives which find use in the present methods and may be present in the compositions include, but are not limited to those with appropriate specificity and antigenicity so as to elicit an antibody that can affect growth of a cancer or bacterial cell. As such, antibody and/or oligosialic acid derivative with such specificity aid in achieving the intended end result of modifying cellular proliferation of a cancer cell or a bacterial cell while minimizing unwanted side effects and toxicity in accordance with the methods. Put differently, the antibody and/or oligosialic acid derivatives employed need not be identical to those disclosed in the Examples section below, so long as the antibody and/or oligosialic acid derivatives are able to elicit an immune response against and/or inhibit growth of a cancerous cell or a bacterial cell. Thus, one of skill will recognize that a number of antibody and/or oligosialic acid derivatives (described in more detail below), can be made without substantially affecting the activity of the antibody and/or oligosialic acid derivatives. This includes compositions of pharmaceutically acceptable salts (e.g., hydrochloride, sulfate salts), solvates (e.g., mixed ionic salts, water, organics), hydrates (e.g., water). For the oligosialic acid compositions, they may be provided in prodrug forms thereof (e.g., esters, acetyl forms), anomers (e.g., α/β mutarotation), tautomers (e.g., keto-enol tautomerism) and stereoisomers (e.g., β-D-isomer). It also includes various alpha (2→8) or (2→9) oligosialic acid derivative compositions that contain one or more immunogenic excipients, such as an adjuvant, carrier and the like, as well as non-immunogenic alpha (2→8) or (2→9) oligosialic acid derivative compositions that are essentially devoid of adjuvant or other immunogenic excipients.

Prodrugs of the oligosialic acid derivatives of the present disclosure are also contemplated. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates. O-acetylated prodrugs are of particular interest. For example, one or more hydroxyl groups of an oligosialic acid derivative of the present disclosure can be O-acetylated.

Whether or not a given oligosialic acid derivative or conjugate thereof is suitable for use according to the present disclosure can be readily determined using various assays, such as those employed in the Experimental section, below. Generally, an oligosialic acid derivative is suitable for use in the methods if it elicits an immune response in a subject that facilitates inhibition of growth of a target cell by at least about 2 to 10-fold, usually by at least about 50-fold and sometimes by at least about 100-fold to 200-fold relative to a normal control cell, as determined using the cell based assays, such as those described in the Experimental section, below. In certain embodiments, an oligosialic acid derivative is one that elicits an antibody that reduces viability of a target cell (such as a particular bacterial cell, cancer cell or cell line), arrests growth and/or induces apoptosis of a target cell, and/or induces cell death, as observed in the cell-based assays described in the Experimental section below when generating an immune response against the cell (e.g., cytotoxicity from enhancing deNAc SA epitope of a bacterial or cancer cell, and making it more susceptible to killing by a secondary antibody such as described herein or SEAM 3, and/or one or more aspects of the immune system).

It will also be appreciated that once isolated, some of the smaller oligosialic acid derivatives can be characterized and made by other techniques, including semi-synthetic as well as standard chemical synthesis. For instance, such oligosialic acid derivatives can be prepared conventionally by techniques known to one of skill in the art, including as described herein and in the Examples. CMP-N-acylated sialic acid analogs and sialyltransferases may also be used in a semi-synthetic approach (e.g., Wakarchuk et al. (2008) *Glycobiology* 18:177). Representative references describing various synthesis approaches, intermediates, precursors, analysis, as well as the synthesis and preparation of conjugates, diagnostics and the like, include U.S. Pat. Nos. 4,315,074; 4,395,399; 4,719,289; 4,806,473; 4,874,813; 4,925,796; 5,180,674; 5,246,840; 5,262,312; 5,278,299; 5,288,637; 5,369,017; 5,677,285; 5,780,603; 5,876,715; 6,040,433; 6,133,239; 6,242,583; 6,271,345; 6,323,339; 6,406,894; 6,476,191; 6,538,117; 6,797,522; 6,927,042; 6,953,850; 7,067,623; and 7,129,333; the disclosures of which are herein incorporated by reference. See also, the following references: "Solid Support Oligosaccharide Synthesis and Combinatorial Carbohydrate Libraries," Peter H. Seeberger Ed, Wiley-Interscience, John Wiley & Sons, Inc, N Y, 2001; Plante et al., Science (2001) 291(5508):1523; Marcaurelle et al., Glycobiology, 2002, 12(6): 69R-77R; Sears et al., Science (2001) 291:2344-2350; Bertozzi et al., Chemical Glycobiology (2001) Science 291:2357-2364; MacCoss et al., Org. Biomol. Chem., 2003, 1:2029; and Liang et al. Science (1996) 274(5292):1520; Kayser et al J Biol. Chem. 1992 267:16934, Keppler et al Glycobiology 2001, 11:11R; Luchansky et al Meth. Enzymol. 2003, 362:

249; Oetke et al Eur. J. Biochem. 2001, 268:4553; and WO/1997/045436; the disclosures of which are herein incorporated by reference.

Pharmaceutically acceptable salts of the oligosialic acid derivatives can be prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanot, 2-diethylaminoethanol, lysine, arginine, histidine, and the like. The reaction is conducted in water, alone or in combination with an inert, water-miscible organic solvent, at a temperature of from about 0° C. to about 100° C., and can be at room temperature. The molar ratio of the oligosialic acid compounds to base used are chosen to provide the ratio desired for any particular salts. For preparing, for example, the ammonium salts of the free acid starting material, the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Pharmaceutical Formulations

Also provided are pharmaceutical compositions containing the antibodies and/or oligosialic acid derivatives employed in the methods of treatment. The term "antibody and/or oligosialic acid derivative composition" is used herein as a matter of convenience to refer generically to compositions comprising an antibody and/or oligosialic acid derivative of the present disclosure, including conjugates. Antibody and/or oligosialic acid derivative compositions can comprise an antibody and/or oligosialic acid derivative, conjugate thereof, or both. Compositions useful for modifying the growth of cells, particularly bacterial and cancer cells, are contemplated by the present disclosure. This includes the compositions comprising an aggregate in particular, as they are readily taken up by cells. Adjuvants may also be used to enhance the effectiveness of the vaccine compositions disclosed herein.

Adjuvants can be added directly to the vaccine compositions or can be administered separately, either concurrently with or shortly after, vaccine administration. Examples of known suitable adjuvants that can be used in humans include, but are not necessarily limited to, alum, aluminum phosphate, aluminum hydroxide, MF59 (4.3% w/v squalene, 0.5% w/v Tween 80, 0.5% w/v SPAN® 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™(WO 90/14837; Chapter 10 in Vaccine design: the subunit and adjuvant approach, eds. Powell & Newman, Plenum Press 1995), containing 5% Squalene, 0.5% TWEEN® 80, and 0.5% SPAN® 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™adjuvant system (RAS), (Ribi Immunochem, Hamilton, MT) containing 2% Squalene, 0.2% TWEEN® 80, and one or more bacterial cell wall components such as monophosphorylipid A (MPL), trehalose dimycolate (TDM), and cell wall skeleton (CWS), preferably MPL +CWS (DETOX™); (2) saponin adjuvants, such as QS21 or STIMULON™(Cambridge Bioscience, Worcester, MA) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg *Curr opin Mol Ther*2001 3:15-24; Roman et al., *Nat. Med.*, 1997, 3, 849-85; Weiner et al., *PNAS USA*, 1997, 94, 10833-10837; Davis et al, *J. Immunol*, 1998, 160, 870-876; Chu etal., *J. Exp. Med*, 1997, 186, 1623-1631; Lipford et al, Ear. *J. Immunol.*, 1997, 27, 2340-2344; Moldoveami el al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al, *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157,2116-2122; Messina et al, *J. Immunol*, 1991, 147, 1759-1764; Yi et al, *J. Immunol*, 1996, 157,4918-4925; Yi et al, *J. Immunol*, 1996, 157, 5394-5402; Yi et al, *J. Immunol*, 1998, 160, 4755-4761; and Yi et al, *J. Immunol*, 1998, 160, 5898-5906; International patent applications WO 96/02555, WO 98/16247, WO 98/18810, WO 98/40100, WO 98/55495, WO 98/37919 and WO 98/52581] i.e. containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21) +3dMPL +IM2 (optionally +a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-gIycero-3-hydroxyphosphoryloxy)-ethylamine MTP-PE), and the like. Adjuvants suitable for human use are of particular interest where the subject is a human. Of specific interest are the inulin-based adjuvants, which can be beneficial particularly in vaccines against both pathogens and cancer (Petrovsky N. (2006) Vaccine 24Suppl 2:S2-26-9.)

The antibody and/or oligosialic acid derivative compositions, e.g., in the form of a pharmaceutically acceptable salt, can be formulated for oral, topical or parenteral administration for use in the methods, as described above. In certain embodiments, e.g., where an antibody and/or oligosialic acid derivative is administered as a liquid injectable (such as in those embodiments where they are administered intravenously or directly into a tissue), an antibody and/or oligosialic acid derivative formulation is provided as a ready-to-use dosage form, or as a reconstitutable storage-stable powder or liquid composed of pharmaceutically acceptable carriers and excipients.

Methods for producing and formulating antibody and/or oligosialic acid derivatives suitable for administration to a subject (e.g., a human subject) are well known in the art. For example, antibody and/or oligosialic acid derivatives can be provided in a pharmaceutical composition comprising an effective amount of an antibody and/or oligosialic acid derivative and a pharmaceutical excipients (e.g., saline). The pharmaceutical composition may optionally include other additives (e.g., buffers, stabilizers, preservatives, and the like). An effective amount of antibody and/or oligosialic acid derivative is generally an amount effective to provide for enhancing an anti-bacterial or anti-cancer response in a subject for a desired period. A therapeutic goal (e.g., reduction in tumor load or protection against bacterial infection or propagation) can be accomplished by single or multiple doses under varying dosing regimen.

By way of illustration, the antibody and/or oligosialic acid derivative compositions can be admixed with conventional pharmaceutically acceptable carriers and excipients (i.e., vehicles) and used in the form of aqueous solutions, tablets, capsules, elixirs, suspensions, syrups, wafers, patches and the like, but usually the antibody and/or oligosialic acid derivative will be provided as an injectable. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations include croscarmellose, microcrystalline cellulose, corn starch, sodium starch glycolate and alginic acid. Preservatives and the like may also be included.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Additionally, it may be desirable to add a coloring agent to make the dosage form more attractive in appearance or to help identify the product.

The compounds of the present disclosure and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the present disclosure and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of the present disclosure and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the antibody and/or oligosialic acid derivative composition is administered as a single pharmaceutical formulation. It also may be administered with an effective amount of another agent that includes other suitable compounds and carriers, and also may be used in combination with other active agents. The present disclosure, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present disclosure may further contain other active agents as are well known in the art.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more alpha (2→8) or (2→9) oligosialic acid derivatives. Similarly, unit dosage forms for injection or intravenous administration may comprise the alpha (2→8) or (2→9) oligosialic acid derivative(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

Optionally, the pharmaceutical composition may contain other pharmaceutically acceptable components, such a buffers, surfactants, antioxidants, viscosity modifying agents, preservatives and the like. Each of these components is well-known in the art. See, e.g., U.S. Pat. No. 5,985,310, the disclosure of which is herein incorporated by reference.

Other components that can be suitable for use in the formulations of the present disclosure can be found in Remington's Pharmaceutical Sciences, Mack Pub. Co., 18th edition (June 1995). In an embodiment, the aqueous cyclodextrin solution further comprise dextrose, e.g., about 5% dextrose.

Utility: Exemplary Applications & Related Embodiments

The methods find use in a variety of applications, where in many applications the methods are modulating at least one cellular function, such as mediation of polysialic acid structure and inhibition of cancerous cell growth, or are modulating an immune response, such in immunization of a subject to elicit antibodies that bind a deNAc SA epitope such as may be borne on a cancerous or bacterial cell (e.g., *Neisseria* or *E. coli* K1).

In the context of modulating at least one cellular function as well as in the context of eliciting anti-cancer cell antibodies, the methods and compositions find use in treating cellular proliferation disorders. Thus, a representative therapeutic application is the treatment of cellular proliferative disease conditions in general, e.g., cancers and related conditions characterized by abnormal cellular proliferation concomitant. Such disease conditions include cancer/neoplastic diseases and other diseases characterized by the presence of unwanted cellular proliferation, e.g., hyperplasias, and the like. As indicated, cellular proliferation disorders include those that abnormally express the deNAc SA epitope, which can be determined using anti-deNAc SA antibody or derivatives thereof.

In the context of modulating an immune response to elicit anti-bacterial antibodies, the methods and compositions find use in eliciting immunoprotective and/or immunotherapeutic immune response against bacteria that bear a deNAc SA, as in capsular polysaccharide of a deNAc SA epitope-bearing *Neisseria* (e.g., *N. meningitidis*, e.g., *N. meningitidis* Groups B and C) or *E. coli* K1.

Of particular interest are antibodies that have antigen binding specificity for the oligosialic acid derivatives described herein or the antigen binding specificity of mAb SEAM 3. Of particular interest are antibodies that specifically bind a deNAc SA epitope with little or no detectable binding to human polysialic acid. Examples of such antibodies include those having a light chain polypeptide comprising CDR1, CDR2 and CDR3 of the variable region of a SEAM 3 or DA2 light chain polypeptide and a heavy chain polypeptide comprising CDR1, CDR2, and CDR3 of the variable region of the heavy chain polypeptide. Additional examples of such antibodies include those having a light chain polypeptide comprising CDR1, CDR2 and CDR3 of the variable region of a DA2 light chain polypeptide and a heavy chain polypeptide comprising CDR1, CDR2, and CDR3 of the variable region of the heavy chain polypeptide. Such antibodies include chimeric antibodies, humanized antibodies, and the like.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells, or so as to protect against disease caused by bacterial infection, which protection can include elimination of detectable bacterial cells; and/or (iii) relief, that is, causing the regression of clinical symptoms.

A variety of hosts are treatable according to the methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans. In the context of anti-bacterial vaccination methods, of interest are hosts that are susceptible to disease that can be caused by infection by a deNAc SA epitope-bearing bacteria, such as *Neisseria* (e.g., *N. meningitidis*, e.g., *N. meningitidis* Groups B and C) or *E. coli* K1.

The methods find use in, among other applications, the treatment of cellular proliferative disease conditions in which an effective amount of the antibody or oligosialic acid derivative composition is administered to the subject in need thereof. Treatment is used broadly as defined above, e.g., to include prevention or at least an amelioration in one or more of the symptoms of the disease, as well as a complete cessation thereof, as well as a reversal and/or complete removal of the disease condition, e.g., cure.

Compositions of the present disclosure can comprise a therapeutically effective amount of an antibody or oligosialic acid derivative composition, as well as any other compatible components, as needed. By "therapeutically effective amount" is meant that the administration of that amount to an individual, either in a single dose, as part of a series of the same or different antibody or oligosialic acid derivative compositions, is effective to inhibit the growth of a cancerous cell in a subject. Such therapeutically effective amount of antibody or oligosialic acid derivative composition and its impact on cell growth includes cooperative and/or synergistic inhibition of cell growth in conjunction with one or more other therapies (e.g., immunotherapy, chemotherapy, radiation therapy etc.) As noted below, the therapeutically effective amount can be adjusted in connection with dosing regimen and diagnostic analysis of the subject's condition (e.g., monitoring for the present or absence of a cell surface epitopes using a SEAM 3 antibody or antibody specific for an oligosialic acid derivative) and the like.

The amount administered to an animal, particularly a human, in the context of the present disclosure should be sufficient to affect a prophylactic or therapeutic response in the animal over a reasonable time frame, and varies depending upon the goal of the administration, the health and physical condition of the individual to be treated, age, the taxonomic group of individual to be treated (e.g., human, non-human primate, primate, etc.), the degree of resolution desired, the formulation of the antibody or oligosialic acid derivative composition, the treating clinician's assessment of the medical situation, and other relevant factors. One skilled in the art will also recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Thus it is expected that the amount will fall in a relatively broad range, but can nevertheless be routinely determined through various features of the subject such as note above.

Also, suitable doses and dosage regimens can be determined by comparisons to anticancer or immunosuppressive agents that are known to affect the desired growth inhibitory or immunosuppressive response. Such dosages include dosages which result in the low dose inhibition of cell growth, without significant side effects. In proper doses and with suitable administration of certain compounds, the compounds of the present disclosure can provide for a wide range of intracellular effects, e.g., from partial inhibition to essentially complete inhibition of cell growth. This is especially important in the context of the present disclosure, as this differential inhibition can potentially be used to discriminate between cancer cells and highly proliferative non-malignant cells. Dosage treatment may be a single dose schedule or a multiple dose schedule (e.g., including ramp and maintenance doses). As indicated, the antibody or oligosialic acid derivative composition may be administered in conjunction with other agents, and thus doses and regiments can vary in this context as well to suit the needs of the subject.

The compositions of the present disclosure can be provided in a pharmaceutically acceptable excipient, which can be a solution such as an aqueous solution, often a saline solution, or they can be provided in powder form. The antibody or oligosialic acid derivative compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of antibody or oligosialic acid derivative of the present disclosure in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

The antibody or oligosialic acid derivative compositions (which may be optionally conjugated) can be used alone or in combination with other therapies (e.g., antibacterial agents, other anti-cancer agents, and the like). When used in combination, the various compositions can be provided in the same or different formulations. Where administered in different formulations, the compositions can be administered at the same or different dosage regimen (e.g., by the same or different routes, at the same or different time (e.g., on the same or different days)), and the like). In general, administration of the antibody or oligosialic acid derivative composition can be performed serially, at the same time, or as a mixture, as described in more detail below. Administration can be serial, with repeated doses of antibody or oligosialic acid derivative composition. Exemplary dosage regimens are described below in more detail.

In general, administration of an antibody or oligosialic acid derivative composition is accomplished by any suitable route, including administration of the composition orally, bucally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 18th ed., Mack Publishing Company, NY (1995).

It is recognized that when administered orally, antibody or oligosialic acid derivatives should be protected from digestion. This is typically accomplished either by complexing the antibody or oligosialic acid derivative with a composition to render it resistant to acidic and enzymatic hydrolysis or by packaging in an appropriately resistant carrier such as a liposome. Means of protecting a compound of interest from digestion are well known in the art.

In order to enhance serum half-life, antibody or oligosialic acid derivative preparations that are injected may also be encapsulated, introduced into the lumen of liposomes, prepared as a colloid, or other conventional techniques may be employed which provide an extended serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antibody or oligosialic acid derivative compositions as a mixture or in serial fashion.

The compositions also can be administered to subject that is at risk of disease to prevent or at least partially arrest the development of disease and its complications. A subject is "at risk" where, for example, the subject exhibits one or more signs or symptoms of disease, but which are insufficient for certain diagnosis and/or who has been or may be exposed to conditions that increase the probability of disease. For example, the antibody or oligosialic acid derivative compositions can also be administered to subject that is at risk of a cancer, has a cancer, or is at risk of metastasis of a cancer having a cell surface deNAc SA epitope (e.g., a cell surface ganglioside that is at least partially de-N-acetylated).

Antibody or oligosialic acid derivative compositions are administered to a host in a manner that provides for the inhibition of growth of a cancerous cell, which may include monitor cell histology, viability, biological marker profile and the like (e.g., monitoring for the presence or absence of selective deNAc SA epitopes etc.). Antibody or oligosialic acid derivative compositions can be administered serially or overlapping to maintain a therapeutically effective amount as believed needed for the desired end result (e.g., inhibition of cancerous cell growth). Typically, each dose and the timing of its administration is generally provided in an amount that is tolerated by the health of the subject, and can be based on IC50 and/or the EC50 as noted above. Thus amounts can vary widely for a given treatment.

Therapeutic response to the dose or treatment regime may be determined by known methods (e.g. by obtaining serum from the individual before and after the initial immunization, and demonstrating a change in the individual's status as noted above, for example an immunoprecipitation assay, or an ELISA, or a bactericidal assay, or a Western blot, or flow cytometric assay, or the like). The dosing may include washout periods to allow for clearance of the initial material, followed by halting or resumption of treatment. Thus dosage strategies can be modified accordingly.

In one embodiment, the antibody or oligosialic acid derivative composition is administered at least once, usually at least twice, and in some embodiments more than twice. In a related embodiment, the antibody or oligosialic acid derivative composition is administered in combination along a dosing schedule and course in conjunction with chemotherapy. In another embodiment, the antibody or oligosialic acid derivative composition is administered in combination with a dosing schedule and course in conjunction with immunotherapy. In yet another embodiment, the antibody or oligosialic acid derivative composition is administered in combination with a dosing schedule and course in conjunction with radiation therapy. Each individual dose of the antibody or oligosialic acid derivative composition may be administered before, during or after the complementary therapy such as immunotherapy, chemotherapy, or radiation therapy. As can be appreciated, combination therapies using an antibody or oligosialic acid derivative composition may be adjusted for a given end need.

Exemplary Cancer Therapies

The antibody and oligosialic acid derivative compositions find use in a variety of cancer therapies (including cancer prevention and post-diagnosis cancer therapy) in a mammalian subject, particularly in a human. Subjects having, suspected of having or at risk of developing a tumor are contemplated for therapy and diagnosis described herein. Samples obtained from such subject are likewise suitable for use in the methods of the present disclosure.

More particularly, antibody and oligosialic acid derivative compositions described herein can be administered to a subject (e.g. a human patient) to, for example, facilitate reduction of viability of cancerous cells, e.g., to reduce tumor size, reduce tumor load, and/or improve the clinical outcome in patients. In particular, antibody and oligosialic acid derivative compositions can be used to disrupt the cell cycle of the cancer cell, and facilitate entry of the cell into apoptosis, e.g., by inducing cancerous cells to enter the pre-G0 cell cycle phase.

In certain embodiments, the antibody and oligosialic acid derivative compositions may be advantageously used in an anti-cancer therapy, particularly where the cancerous cells present a deNAc SA epitope on an extracellularly accessible cell surface (e.g., a deNAc SA epitope on an at least partially de-N-acetylated ganglioside or other glycoconjugate). In one embodiment, the cancer is one that presents a SEAM 3-reactive antigen and/or a DA2-reactive antigen. Cancers that present a SEAM 3-reactive antigen and/or a DA2-reactive antigen can be identified by methods known in the art. Exemplary methods of detection and diagnosis are described below.

Where the anti-cancer therapy comprises administration of an antibody and/or oligosialic acid derivative composition, the anti-cancer therapy can be particularly directed to dividing (replicating, proliferating) cancerous cells. As shown in the Examples below, antibody raised against oligosialic acid derivatives were particularly effective against cancerous cells bearing the epitope specifically bound by SEAM 3 and/or DA2 antibody. For example, the level of extracellularly accessible antigen bound by SEAM 3 is increased during cell division as compared to non-dividing cells, and binding of SEAM 3 drives the cell toward anaphase (into pre-G0). Since most cancers are more rapidly dividing than normal cells of the same type, cells that possess a SEAM 3-reactive antigen are attractive for antibody and oligosialic acid derivative-based cancer therapy. Also, the antibodies identified herein to the oligosialic acid derivatives of the present disclosure exhibit enhanced binding relative to binding by SEAM 3 to the OS-conjugate vaccine-derived antigen relative to normal PSA control, thus having clinical benefits in addition to SEAM 3. For example, antibodies generated using an oligosialic acid derivative composition made by the methods described herein such as DA2 may bind a SEAM 3 reactive antigen with an improved binding affinity and/or binding avidity relative to normal PSA control. In another example, antibodies generated using an oligosialic acid derivative composition made by the methods described herein such as DA2 may bind an epitope of a SEAM 3 reactive antigen that is different than the epitope bound by the SEAM 3 monoclonal antibody relative to normal PSA control. As illustrated in the examples, DA2 was highly effective in binding as well as killing cancer cells bearing a DA2-reactive antigen.

Thus the present disclosure particularly provides anti-cancer therapy directed toward cancerous cells involving administration of antibody and/or oligosialic acid derivative compositions having an epitope recognized by a SEAM 3 and/or DA2 mAb. Cancers particularly amenable to antibody and/or oligosialic acid derivative therapy can be identified by examining markers of cellular proliferation (e.g., Ki-67 antigen) and/or by examining the presence/accessibility of the deNAc SA epitope bound by SEAM 3 and/or DA2 in dividing cells or by the antibodies specific for the oligosialic acid derivatives of the present disclosure (e.g., as in an in vitro assay).

Cancers having a cell surface-accessible deNAc SA epitope include those having an at least partially de-N-acetylated ganglioside and/or a protein having a sialic acid modification that contains a deNAc SA epitope. Cancers having de-N-acetylated gangliosides have been described.

The presence of de-N-acetyl sialic acid residues in normal human tissue appears to be transient and very low abundance, being found only in a few blood vessels, infiltrating mononuclear cells in the skin and colon, and at moderate levels in skin melanocytes. It is prevalent only in abnormal cells, such as melanomas, leukemias and lymphomas. Since expression of high levels of deNAc SA antigens (e.g., de-N-acetyl gangliosides) occurs predominantly in cancer cells, treatment with antibody and/or oligosialic acid derivative compositions can be used to induce cytotoxicity, and can block tumor growth. In addition, antibody and/or oligosialic acid derivative compositions can be used therapeutically to effect/prevent adhesion and invasion of cancer cells in other tissues.

Exemplary cancers presenting a deNAc SA epitope include cancer cells presenting a de-N-acetyl ganglioside containing a de-N-acetyl sialic acid residue (e.g. GM2alpha, GM1alpha, GD1beta, GM1b, GD1c, GD1alpha, GM3, GM2, GM1, GD13, GT13, GT1halpha, GD3, GD2, GD1b, GT1b, GQ1b, Gomega1halpha, GT3, GT2, GT1c, GQ1c, and GP1c). Of particular interest are gangliosides that contain two or more sialic acid residues linked by alpha 2-8 glycosidic bonds (e.g., GD1c, GT13, GD3, GD1b, GT1b, GQ1b, Gomega1halpha, GT3, GT1c, GQ1c, and GP1c) in which at least one residue is de-N-acetylated. In some embodiments, the ganglioside that contains two or more sialic acid residues linked by alpha 2-8 glycosidic bonds is a ganglioside other than GD3 and/or other than GM3. In some embodiments, the target of the cancer is a deNAc SA epitope other than one present on a de-N-acetylated ganglioside (e.g., a de-N-acetylated residue of a sialic acid-modified protein).

In one embodiment antibody and/or oligosialic acid derivative compositions can be used to treat cancers that present a SEAM 3 and/or DA2 reactive antigen on a cell surface, including cancers that exhibit an extracellularly accessible SEAM 3 and/or DA2-reactive antigen during cell division.

In another embodiment antibody and/or oligosialic acid derivative compositions can be used to treat cancers that present deNAc SA epitope on a cell surface, including cancers that exhibit an extracellularly accessible reactive antigen during cell rest.

It should be noted that while deNAc SA epitopes and/or SEAM 3 and/or DA2-reactive antigens may be expressed at higher levels on a cancer cell compared to a non-cancerous cell, this is not a limitation of the therapies disclosed herein. For example, where the cancer involves a cell type that can be replenished (e.g., B cell, T cell, or other cell of hematopoietic origin, as in leukemias and lymphomas), inhibition of normal cell growth can be acceptable since damage to a subject by depleting such cells can be treated (e.g., with drugs to stimulate repopulation of normal cells, e.g., GM-CSF, EPO, and the like).

The methods relating to cancer contemplated herein include, for example, use of antibody and/or oligosialic acid derivative therapy alone or in combination with deNAc SA antigens as a anti-cancer vaccine or therapy, as well as use of antibodies generated using deNAc SA antigens in anti-cancer vaccines (e.g., by passive immunization) or therapies. The methods are useful in the context of treating or preventing a wide variety of cancers, including carcinomas, sarcomas, leukemias, and lymphomas.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium. In some embodiments, the methods do not include treatment of melanoma (i.e., the cancer is other than melanoma). In other embodiments, the methods do not include treatment of lymphoma (i.e., the cancer is other than lymphoma). In certain embodiments, the methods of the present disclosure are used to treat cancer cells known to express de-N-acetyl gangliosides include melanomas and some lymphomas. As noted above, cancers that overexpress the precursor gangliosides GM3 and GD3 are likely to also express the greatest amount of de-N-acetyl gangliosides on the cell surface.

Combinations with Other Cancer Therapies

Therapeutic administration of the antibody and/or oligosialic acid derivative compositions can include administration as a part of a therapeutic regimen that may or may not be in conjunction with additional standard anti-cancer therapeutics, including but not limited to immunotherapy, chemotherapeutic agents and surgery (e.g., as those described further below). In addition, therapeutic administration of the antibody and/or oligosialic acid derivative compositions can also be post-therapeutic treatment of the subject with an anti-cancer therapy, where the anti-cancer therapy can be, for example, surgery, radiation therapy, administration of chemotherapeutic agents, and the like. Use of monoclonal antibodies, particularly monoclonal antibodies that can provide for complement-mediated killing, and/or antibody-dependent cellular cytotoxicity-mediated killing, of a target cell are of particular interest (e.g., treatment with an anti-deNAc SA epitope antibody (e.g., DA2, SEAM 3 or an antibody specific for an oligosialic acid derivative of the present disclosure) after identification of a primary tumor composed of cells expressing a deNAc SA epitope (e.g., a de-N-acetyl ganglioside)). Cancer therapy using antibody and/or oligosialic acid derivative compositions of the present disclosure in combination with immunotherapy that employs PSA antigen/anti-deNAc SA epitope antibodies is of particular interest (U.S. Ser. No. 11/645,255 and PCT Application No. US2006/048850; incorporated herein by reference).

For example, the antibody and/or oligosialic acid derivative compositions can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the alpha (2→8) or (2→9) oligosialic acid derivative is used in connection with surgical intervention, the antibody and/or oligosialic acid derivative compositions can be administered prior to, at the time of, or after surgery to remove cancerous cells, and may be administered systemically or locally at the surgical site. The antibody and/or oligosialic acid derivative compositions alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the antibody and/or oligosialic acid derivative-based therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In the treatment of some individuals with the compounds of the present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Particular applications in which the methods and compositions find use include those described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

Production of Anti-Alpha (2→8) or (2→9) Oligosialic Acid Derivative Antibody Response Alpha (2→8) or (2→9) oligosialic acid derivatives, including conjugates thereof, as described herein can be used in eliciting an anti-bacterial antibody response, as well as in eliciting an anti-cancer cell antibody response. In general immunization is accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that alpha (2→8) or (2→9) oligosialic acid derivatives and related compounds described herein (e.g., conjugates), when administered orally, should be protected from digestion. This is typically accomplished either by complexing the alpha (2→8) or (2→9) oligosialic acid derivative with a composition to render it resistant to acidic and enzymatic hydrolysis or by packaging in an appropriately resistant carrier such as a liposome. Means of protecting a compound of interest from digestion are well known in the art.

In order to enhance serum half-life, the antigenic preparations that are injected may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

The compositions are administered to suitable subject, e.g., a subject that is at risk from acquiring a Neisserial disease or at risk of developing a cancer bearing a deNAc SA epitope (e.g., as present in a SEAM 3 and/or DA2-reactive antigen) to prevent or at least partially arrest the development of disease and its complications. An amount adequate to accomplish this is defined as a "therapeutically effective dose." Amounts effective for therapeutic use will depend on, e.g., the antigen composition, the manner of administration, and a variety of subject-specific parameters such as the weight and general state of health of the subject, any or all of which may be modified according to the judgment of the clinician.

Single or multiple doses of the antigen compositions may be administered depending on the dosage and frequency required and tolerated by the patient, and route of administration. In general, immunization is provided to as to elicit an immune response in the subject, where the compounds of the present disclosure can provide an advantage that immunization does not elicit detectable antibodies that significantly cross-react with polysialic acid in the subject (stated differently, elicits no clinically relevant autoantibody response directed against host sialic acid), and can include production of antibodies bactericidal for N. meningitidis as well as for E. coli K1 and/or production of antibodies that inhibit cancer cell proliferation.

In particular embodiments, the antigen compositions described herein are administered serially. First, an immunogenically effective dose of an alpha (2→8) or (2→9) oligosialic acid derivative (which may be conjugated to a carrier, and may be with or without excipients) is administered to a subject. The first dose is generally administered in an amount effective to elicit an immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient, usually about 0.005 mg to about 0.015 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first antigen composition of alpha (2→8) or (2→9) oligosialic acid derivative, a therapeutically effective dose of a second antigen composition (e.g. alpha (2→8) or (2→9) oligosialic acid derivative, optionally conjugated and with or without excipients) is administered to the subject after the subject has been immunologically primed by exposure to the first dose. The booster may be administered days, weeks or months after the initial immunization, depending upon the patient's response and condition.

The presence of a desired immune response may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) and/or demonstrating that the magnitude of the immune response to the second injection is higher than that of a control subject immunized for the first time with the composition used for the second injection (e.g. immunological priming). Immunologic priming and/or the existence of an immune response to the first antigen composition may also be assumed by waiting for a period of time after the first immunization that, based on previous experience, is a sufficient time for an immune response and/or priming to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

In certain embodiments, a therapeutically effective dose of a third antigen composition prepared from is administered to the subject after the individual has been primed and/or mounted an immune response to the second antigen composition. The methods disclosed herein also contemplate administration of of a fourth, fifth, sixth or greater booster immunization, using either a fourth, fifth or sixth antigen composition.

The subject may be immunologically naïve with respect to *Neisseria meningitidis* or *E. coli* K1 or a deNAc SA epitope-bearing cancer. For immunoprevention, the alpha (2→8) or (2→9) oligosialic acid derivative can be administered prior the first sign of disease symptoms, or at the first sign of possible or actual exposure to infection or disease (e.g., due to exposure or infection by *Neisseria* or *E. coli* K1).

Passive Immunization and Other Antibody-Based Therapies

In addition, anti-alpha (2→8) or (2→9) oligosialic acid derivative antibodies generated using the methods described herein can be used to provide for passive immunotherapy, e.g., to treat or prevent *N. meningitidis*-mediated or *E. coli* K1-mediated disease in mammalian subjects. Particularly, the antibodies generated using the de-N-acetylated PS or conjugates thereof according to the present disclosure can be provided in a pharmaceutical composition suitable for administration to a subject, so as to provide for passive protection of the subject against *N. meningitidis* of *E. coli* K1 disease, or for treatment of cancer.

More particularly, immunoprotective antibodies generated according to the methods described herein and that recognize *Neisserial* PS or *E. coli* K1 epitopes can be administered to a subject (e.g. a human patient) to induce passive immunity against a Neisserial disease, either to prevent infection or disease from occurring, or as a therapy to improve the clinical outcome in patients with established disease (e.g. decreased complication rate such as shock, decreased mortality rate, or decreased morbidity, such as deafness). Where the antibodies are administered to effect a cancer therapy, the antibodies can optionally have attached a drug for targeting to the cancer cell to effect tumor killing or clearance, e.g., a toxin (e.g., ricin), radionuclide, and the like.

Diagnostics

Antibodies reactive with a deNAc SA epitope can be used to detect deNAc SA antigens in a biological sample obtained from a subject having or suspected of having cancerous cells having a cell surface accessible deNAc SA epitope (e.g., a de-N-acetylated cell surface ganglioside or glycoconjugate) using anti-deNAc SA epitope antibodies in immunodiagnostic techniques as described in (See U.S. Ser. No. 11/645,255 and PCT Application No. US2006/048850; incorporated herein by reference). Such antibodies also find use in detection of deNAc SA antigens in a biological sample obtained from a subject having or suspected of having bacteria having cell surface accessible deNAc SA epitopes, e.g., bacteria having polysaccharide containing a deNAc SA epitope, e.g., *Neisseria* (e.g., *Neisseria meningitidis*, particularly *N. meningitidis* Groups B and C), *E. coli* K1. The present disclosure provides additional antibodies suitable for this purpose, particularly in the context of detection of cancer cells given their ability to recognize and bind a deNAc SA epitope on both dividing and non-dividing cells. Such diagnostics can be useful to identify patients amenable to the therapies disclosed herein, and/or to monitor response to therapy. Further, such antibodies can have or be selected to have antigen-binding properties such that the antibodies exhibit little or no detectable binding to host (e.g., mammalian, especially human) polysialic acid, thereby providing for decreased risk of false positive results.

Briefly, the antigen binding specificity of anti-deNAc SA epitope antibodies can be exploited in this context, to facilitate detection of deNAc SA epitopes on a cancerous or bacterial cell in a sample with little or no detectable binding to host-derived PSA, thereby reducing the incidence of false positive results. Such detection methods can be used in the context of diagnosis, identification of subject suitable to antibody and/or oligosialic acid derivative-based therapy where the antibody specifically binds an deNAc SA epitope and/or a SEAM 3 and/or DA2-reactive antigen, monitoring of therapy (e.g., to follow response to therapy), and the like.

Suitable immunodiagnostic techniques include, but are not necessarily limited to, both in vitro and in vivo (imaging) methods. Where the methods are in vitro, the biological sample can be any sample in which a deNAc SA antigen may be present, including but not limited to, blood samples (including whole blood, serum, etc.), tissues, whole cells (e.g., intact cells), and tissue or cell extracts. Assays can take a wide variety of forms, such as competition, direct reaction, or sandwich type assays. Exemplary assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-deNAc SA epitope antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing deNAc SA epitopes under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with anti-deNAc SA epitope antibody according to the present disclosure. A biological sample containing or suspected of containing a deNAc SA antigen (e.g., a tumor antigen having a deNAc SA epitope, such as a de-N-acetylated ganglioside), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound deNAc SA antigen from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and deNAc SA antigen form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing deNAc SA antigen to provide for formation of particle-antibody-deNAc SA antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which a deNAc SA antigen may be present, including but not limited to, blood samples (including whole blood, serum, etc.), tissues, whole cells (e.g., intact cells), and tissue or cell extracts containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments, particularly as in embodiments involving detection of cancer cells, it may be desirable to conduct the assay using a sample from the subject to be diagnosed that contains intact, living cells.

DeNAc SA antigen detection can then be assessed on an extracellular surface of the cells, and can further be assessed during cell division.

Diagnostic assays can also be conducted in situ. For example, anti-deNAc SA epitope antibodies can be detectably labeled, administered to a subject suspected of having a cancer characterized by cell surface expression of a deNAc SA epitope, and bound detectably labeled antibody detected using imaging methods available in the art.

The diagnostic assays described herein can be used to determine whether a subject has a cancer that is more or less amenable to therapy using antibody and/or oligosialic acid derivative-based therapy, as well as monitor the progress of treatment in a subject. It also may be used to assess the course of other combination therapies (e.g., deNAc SA antigen vaccine and/or anti-deNAc SA antigen antibody therapy as described in (U.S. Ser. No. 11/645,255 and PCT Application No. US2006/048850; incorporated herein by reference). Thus, the diagnostic assays can inform selection of therapy and treatment regimen by a clinician.

Where the methods are in vitro, the biological sample can be any sample in which a SEAM 3 and/or DA2-reactive antigen may be present, including but not limited to, blood samples (including whole blood, serum, etc.), tissues, whole cells (e.g., intact cells, i.e., cells that have not been subjected to permeabilization), or cell lysates (e.g., as obtained from treatment of a tissue sample). For example, the assay can involve detection of a SEAM 3 and/or DA2-reactive antigen on cells in a histological tissue sample. For example, the tissue sample may be fixed (e.g., by formalin treatment) and may be provided embedded in a support (e.g., in paraffin) or frozen unfixed tissue.

The SEAM 3 and/or DA2-reactive antigen can be detected by detection of specific binding of an antibody, usually a monoclonal antibody (mAb), that has the antigen-binding specificity of SEAM 3 and/or DA2. In this embodiment, the SEAM 3 and/or DA2-reactive antigen may be present on the cell surface at any stage of the cell cycle, including during cell division. Of note is that in some instances, cancers that present a SEAM 3 and/or DA2-reactive antigen during cell division may present a lower or no detectable level of SEAM 3 and/or DA2-reactive antigen when the cell is quiescent (i.e., not undergoing cell division). However, as illustrated in the examples below, SEAM 3 and/or DA2-reactive antigen can be detected in non-dividing cells by detecting SEAM 3 and/or DA2-reactive antigen in a permeabilized test cell. A test cancer cell that exhibits a pattern of staining with a SEAM 3 and/or DA2 antibody (or an antibody having the antigen binding specificity of SEAM 3 and/or DA2) that is distinct from a pattern of antibody staining in a normal cell is identified as a cancerous cell that exhibits a SEAM 3 and/or DA2-reactive antigen. Such cancers are thus amenable to therapy with an antibody that specifically binds the SEAM 3 and/or DA2-reactive antigen (e.g., the mAb SEAM 3 and/or the mAb DA2).

The above-described assay reagents, including the antibodies generated by immunization with a deNAc SA antigen according to the methods described in U.S. Ser. No. 11/645,255 and PCT Application No. US2006/048850, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Kits & Systems

Also provided are kits and systems that find use in practicing the methods, as described above. For example, kits and systems for practicing the methods may include one or more pharmaceutical formulations that include antibody and/or oligosialic acid derivative. As such, in certain embodiments the kits may include a single pharmaceutical composition present as one or more unit dosages. In yet other embodiments, the kits may include two or more separate pharmaceutical compositions.

Thus the kits can include one or more of, depending upon the intended use of the kit, the compositions described herein, such as: an oligosialic acid derivative and/or antibody specific thereto, cells suitable related for assays or screening, an anti-deNAc SA epitope antibody, and the like. Other optional components of the kit include: buffers, etc., for administering an oligosialic acid derivative and/or antibody specific thereto, and/or for performing a diagnostic assay. The various components of the kit may be present in separate containers or certain compatible components may be pre-combined into a single container, as desired.

In addition to the above components, the kits may further include instructions for practicing the methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In a specific embodiment, a kit is provided for use in treating a host suffering from a cellular proliferative disease condition. This kit includes a pharmaceutical composition comprising an oligosialic acid derivative and/or antibody specific thereto, and instructions for the effective use of the pharmaceutical composition in a method of treating a host suffering from a cancerous condition by inhibiting the growth of a cancer cell in a subject, or by providing for an anti-deNAc SA immune response, e.g., to elicit antibodies that bind a cancer cell bearing a deNAc SA epitope. Such instructions may include not only the appropriate handling properties, dosing regiment and method of administration, and the like, but can further include instructions to optionally screen the subject for a de-N-acetylated sialic acid (deNAc SA) epitope. This aspect can assist the practitioner of the kit in gauging the potential responsiveness of the subject to treatment with an oligosialic acid derivative and/or antibody specific thereto, including timing and duration of treatment relative to the type and growth stage of the cancer. Thus in another embodiment, the kit may further include an antibody or other reagent for detecting a de-N-acetylated sialic acid (deNAc SA) epitope on an extracellularly accessible surface of a cancer cell, such as SEAM 3 and/or DA2. In another embodiment, the kit includes one or more alpha (2→8) or (2→9) oligosialic acid derivatives that comprise a conjugate with a detectable label, such as a fluorophore.

In another specific embodiment, a kit is provided for use in immunizing a host at risk of, or having, a disease or disease symptom of infection by a bacteria bearing a deNAc SA epitope, e.g., a deNAc SA epitope on a bacterial polysaccharide capsule (e.g., Neisseria (e.g., N. meningitidis, especially Groups B and C N. meningitidis), E. coli K1). This kit includes a pharmaceutical composition comprising an oligosialic acid derivative and/or antibody specific thereto, and instructions for the effective use in immunization or treatment of a host having, or at risk of, bacterial infection. Such instructions may include not only the appropriate handling properties, dosing regiment and method of administration, and the like, but can further include instructions to optionally screen the subject for a de-N-acetylated sialic acid (deNAc SA) epitope. This aspect assists the practitioner of the kit in gauging the potential responsiveness of the subject to immunization with an oligosialic acid derivative and/or antibody specific thereto. Thus in another embodiment, the kit may further include an antibody or other reagent for detecting a de-N-acetylated sialic acid (deNAc SA) epitope on an extracellularly accessible surface of a cancer cell, such as SEAM 3 and/or DA2.

The term "system" as employed herein refers to a collection of an oligosialic acid derivative and/or antibody specific thereto and one or more second therapeutic agents, present in single or disparate compositions that are brought together for the purpose of practicing the methods. For example, separately obtained oligosialic acid derivative and/or antibody specific thereto and chemotherapy dosage forms brought together and coadministered to a subject are a system according to the present disclosure.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Preparation of Alpha (2→8)N-Acetyl Neuraminic Acid Oligosaccharides (OS)

Colominic acid (100 mg, Sigma-Aldrich, Saint Louis, Mo.), which is PSA isolated from the capsule of *Escherichia coli* K1 bacteria, was dissolved in 5 ml of 20 mM HCl and heated to 50° C. for 2 hrs. After cooling to ambient temperature, the pH was increased to 8-9 with 2M NaOH. The solution was dialyzed (1 kDa cutoff tubing, Spectrapor obtained from Thermo-Fisher Scientific, Waltham, Mass.) in water and lyophilized.

Example 2

Sodium Borohydride Treatment of Oligosaccharides

The lyophilized OS (100 mg) from Example 1 were combined with 10 mg of sodium borohydride (Sigma-Aldrich) in 5 ml of water and left at ambient temperature overnight. Over the course of several hours, the pH of the solution rises from approximately 8.5 to approximately 10. The reaction mixture was dialyzed in water and lyophilized as described above in Example 1. The resulting OS antigen was determined to contain about 33% neuraminic acid residues, and contain a mixture of chains having a degree of polymerization of about 2-20.

Example 3

Analysis of Sodium Borohydride-Treated Oligosaccharides

Sodium borohydride-treated OS of Example 2 were separated by ion exchange chromatography on an Äkta™ FPLC fitted with a 5 ml HiTrap Q FF™ anion exchange column (GE Healthcare Bio-Sciences Corp., Piscataway, N.J.). 20 mg of OS were dissolved in 0.5 ml of 20 mM Bis-Tris buffer (Sigma-Aldrich), pH 8 and injected onto the column. OS were eluted from the column with a 0M to 0.5M gradient of sodium sulfate in 20 mM Bis-Tris buffer. The amount of sialic acid and de-N-acetyl sialic acid in each 1 ml fraction was determined by resorcinol assay described in Example 6, below. Also, the ability of each fraction to inhibit binding of SEAM 3 to N-propionyl NmB polysaccharide dodecylamine was determined by inhibition ELISA as described in Example 5, below.

The results are summarized in the graph shown in FIG. 1. Essentially all of the OS retained by the column contained both sialic acid and de-N-acetyl sialic acid. The ratio ranged from roughly 3:1 for the short oligosaccharides eluting at low salt to 10:1 or more for the longer polysaccharides eluting with higher salt concentrations. Also, all fractions containing a mixture of sialic acid and de-N-acetyl sialic acid inhibited SEAM 3 binding.

After dialysis in water and lyophilization each fraction contained 1 mg or less of OS. Treatment of selected fractions with excess amounts of the exoneuraminidase SIALIDASE A (Prozyme, San Leandro, Calif.) did not decrease the amount of OS or affect the ability of the OS to inhibit SEAM 3 binding. Since exoneuraminidases are unable to degrade PSA that terminate at the non-reducing end with a de-N-acetyl residue (i.e. neuraminic acid), the results suggest that de-N-acetylation resulting from sodium borohydride treatment is occurring, at least in part if not wholly at the non-reducing end of the OS.

It is also possible that borohydride, boranes, or borates produced by reaction of borohydride with the OS results in the formation of boron-OS complexes. However, several samples of OS derivatives that are good inhibitors of SEAM 3 binding were tested for the presence of boron by azomethine (Sigma-Aldrich) colorimetric assay (Zenki et al, Fresenius' J Anal Chem, 1989, 334:238) and by inductively coupled plasma mass spectroscopy (performed by Galbraith Laboratories, Inc., Knoxville, Tenn. An amount corresponding to mole fraction of less than 1% could be detected.

Figure 2:
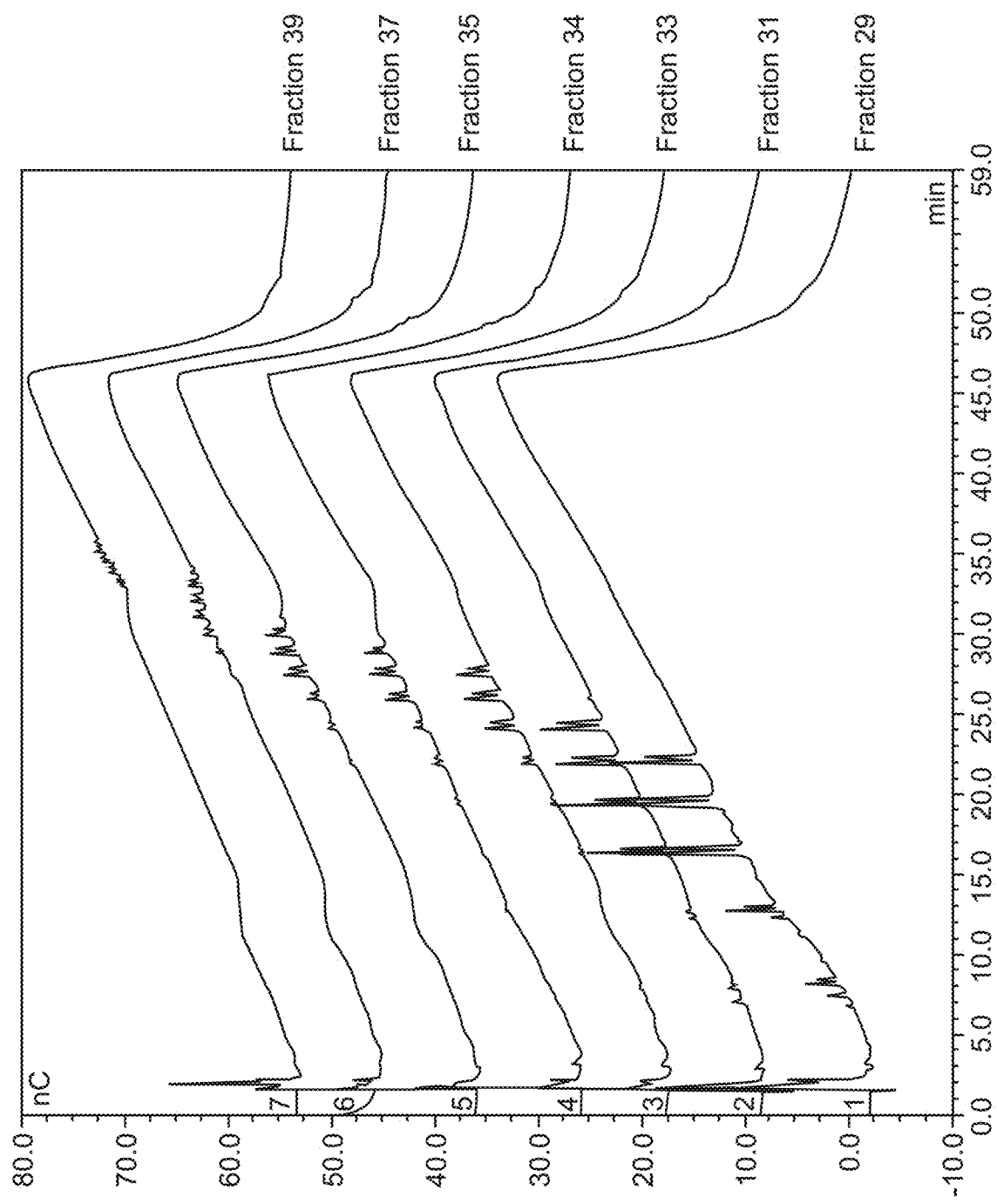
Figure 3:
Figure 4:
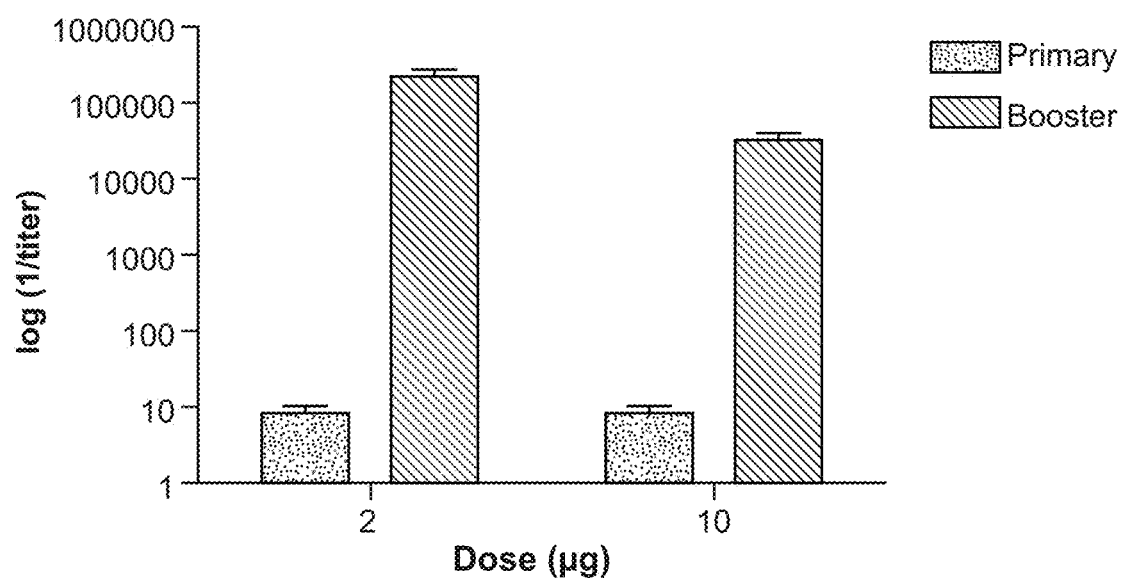

The OS fractions were further analyzed by high performance anion exchange chromatography with pulsed amperometric detection (HPAC-PAD) to determine the length of OS in each fraction. The results for selected fractions are shown in FIG. 2. The fraction having shortest OS that were still able to inhibit SEAM 3 binding were in fraction 29 which contained a mixture of degree of polymerization (Dp) of 2 to 6 but mostly 4 to 6 (FIG. 2).

Example 4

Preparation of Dodecylamine Derivatives of N-Propionyl NmB PS

Twenty (20) mg of N-propionyl NmB polysaccharide (N-Pr NmB PS) oxidized with periodate prepared as described by Granoff et al (Granoff et al., J. Immunol, 1998, 160: 5028) was combined in water (5 ml) with 5 μl of dodecylamine (Thermo-Fisher). The pH was adjusted to 8 with 2M HCl and the mixture stirred for 3 hrs. Sodium cyanoborohydride (5 mg, Sigma-Aldrich) was added and the mixture was stirred at ambient temperature for 24 hours then dialyzed in water for 3 to 5 days to remove excess dodecylamine. The dodecylamine antigen (~1 mg/ml in PBS buffer) was stored at 4° C.

Example 5

Seam 3 Inhibitor Assay

ELISA plates for testing inhibitors of SEAM 3 binding were prepared by diluting the dodecylamine N-propionyl NmB derivative of Example 4 above 1:200 in PBS buffer and adding 100 μl per well of a 96 well microtiter plate (Immulon II HB, Dynatech, Chantilly, Va.). The plates were stored overnight at 4° C. before use in assays. The plates were washed with PBS buffer (5×) and blocked with PBS buffer containing 1% (weight/volume) of bovine serum albumin (Sigma; blocking buffer) for 1 hour at ambient temperature. The inhibitors were diluted in blocking buffer on the plate then SEAM 3 was added in blocking buffer (100 μl total per well). After incubating the plate overnight at 4° C., the plates were washed with PBS buffer (5×) and rabbit anti-mouse-alkaline phosphatase conjugate antibody (Zymed, South San Francisco, Calif.) diluted in blocking buffer was added. After incubating an additional hour, the plates were washed (5×) with PBS buffer and the bound antibody was detected by adding p-nitrophenyl phosphate substrate (Sigma-Aldrich) in 50 mM sodium carbonate buffer, pH 9, containing 1 mM $MgCl_2$. The absorbance at 405 nm after 60 minutes incubation at ambient temperature was measured using a BioRad Model 550 microtiter plate reader (Richmond, Calif.).

Example 6

Determination of Sialic Acid and Neuraminic Acid in PSA

The concentration of sialic acid and de-N-acetyl sialic acid in PSA derivative stock solutions or column fractions was determined by the Svennerholm resorcinol reaction (Svennerholm, L. (1957) Biochim. Biophys. Acta 24:604) modified as follows. Resorcinol working reagent was prepared by combining 9.75 ml of water, 0.25 ml of 0.1 M CuSO4.5H2O, 10 ml of 20 milligram per ml solution of resorcinol in water, and 80 ml of concentrated HCl. The resorcinol working reagent (300 μl) was combined with the sialic acid or de-N-acetyl sialic acid sample solution (up to 50 micrograms of sialic acid) or standard stock solution in water (300 μl) in a polypropylene deep well (2 ml) microtiter plate. The plate was sealed with a plate cover and heated in a boiling water bath for 30 minutes. After cooling to ambient temperature, isoamyl alcohol (600 μl) was added and mixed using a pipette. The phases were allowed to separate and the upper isoamyl alcohol layer was removed to a clean microtiter plate. 250 μl of the isoamyl alcohol extract and the lower aqueous solution were transferred separately to a polystyrene microtiter plate and the absorbance at 495 nm and 580 nm was measured.

The amount of N-acetyl sialic acid was determined from the absorbance of the isoamyl alcohol fraction at 580 nm and the amount of de-N-acetyl sialic acid was determined from the absorbance of the aqueous fraction at 495 nm in comparison to a standard curve for each. The amount of de-N-acetyl sialic acid was corrected for the amount of de-N-acetylation that occurs during the acid hydrolysis step of the assay by measuring the amount of de-N-acetylation that occurs in the sialic acid standard.

Example 7

Determining the Minimal Length of Oligosaccharide for Reactivity with Seam 3

Figure 5:
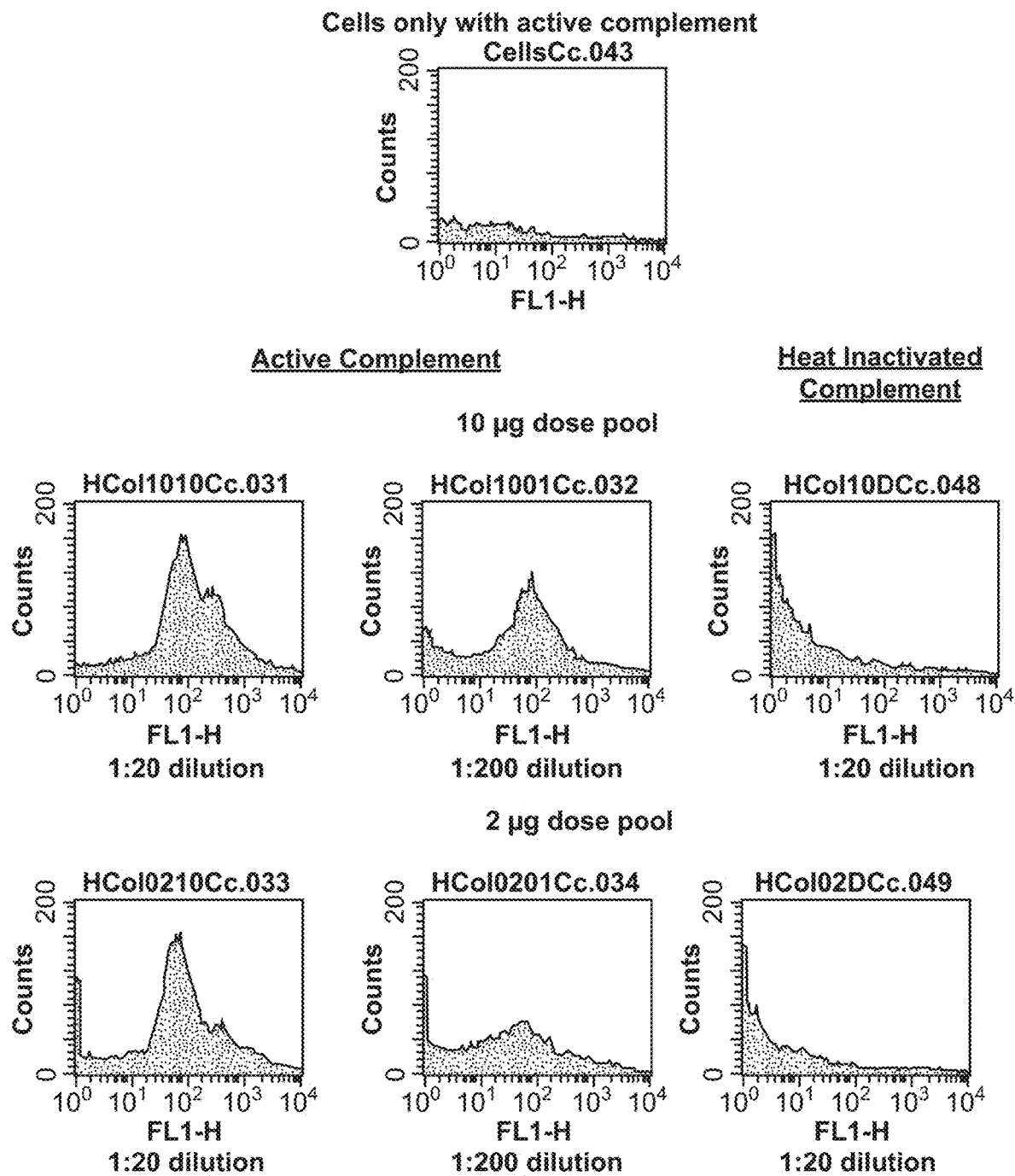

To prepare a vaccine that is intended to elicit antibodies and have specificities similar to that of SEAM 3 it is necessary to determine the minimal alpha (2→8) neuraminic acid OS length that is reactive with SEAM 3. Longer PSA has the potential to elicit antibodies that are reactive with other human PSA antigens. To determine the minimal length OS recognized by SEAM 3, N-acetyl neuraminic acid monomer, and alpha (2→8) linked dimer, trimer, and tetramer (10 mg each, EY Scientific Laboratories, San Mateo, Calif.) were combined with 1 mg of sodium borohydride in water as described above. After dialysis and lyophilization, each oligomer was tested by ELISA for the ability to inhibit binding of SEAM 3 to N-Pr NmB PS-dodecylamine. The results are summarized in Table 1. None of the untreated control OS (i.e., OS that had not been treated with sodium borohydride) were able to inhibit SEAM 3 binding. As shown in Table 1, a borohydride-treated oligosaccharide as short as a tetramer exhibits all of the activity of the much longer nominal polysaccharide antigen N-Pr NmB PS.

TABLE 1

Specificity of SEAM 3 determined by inhibition ELISA

| Inhibitor | Dp* | $[IC_{50}]$ (μg/ml)+ |
|---|---|---|
| N-Propionyl PSA | >20 | 0.08 |
| Re-N-Acetyl PSA | >20 | 1.6 |
| Tetramer | 3 | 0.02 |
| Trimer | 2 | 1.9 |
| Dimer | 1 | 51 |
| NmC PS# | >20 | >200 |

*Excluding the reducing end residue, which is reduced and the non-reducing end residue that may be de-N-acetylated and/or form a complex with boron.
+Concentrations of sialic acid in the stock solutions used in the inhibition experiments were determined by resorcinol assay.
NeuNmC PS, NmW PS and NeuNmW PS were also tested with similar results to NmC PS (NmC PS, and NmW PS are *N. meningitidis* group C and W, respectively, capsular polysaccharides)

Example 8

Preparation of a OS-Tetanus Toxoid Conjugate Vaccine

Sodium borohydride-treated OS prepared as described above (20 mg) was oxidized with sodium periodate (6 μmol or 1 equivalent for every 10 residues) for 1 hr in 2 ml of 0.1M sodium acetate buffer, pH 6.5. Ethylene glycol (100 μl of a 10% (volume/volume) solution in water) was added to destroy any remaining periodate and the solution was dialyzed in water. OS (10 mg) was combined with 5 mg of tetanus toxoid (BioVeris Corp., Gaithersburg, Md.) in 5 ml of PBS buffer. The solution was stirred overnight at ambient temperature in a brown glass Reacti-Vial (Pierce Chemical Company, Rockford, Ill.). The following day, 5 mg of sodium cyanoborohydride was added and stirring of the mixture was continued for 2 days. The reaction mixture was dialyzed (10-14 kDa cutoff membrane) in PBS buffer. The vaccine preparation was sterile filtered (0.22μ), aliquoted and stored at −80° C. until used. The vaccine solution contained 2.4 mg/ml sialic acid and 1.2 mg/ml de-N-acetyl sialic acid determined by resorcinol assay and 1.5 mg/ml protein as determined by BCA assay (Bio-Rad). To demonstrate that the OS antigen was covalently linked to tetanus toxoid, a portion of the vaccine was separated on a 4%-15% sodium dodecyl sulfate-polyacrylamide gel (Bio-Rad) and tested for reactivity with SEAM 3 by Western blot. Bound SEAM 3 was detected using a rabbit anti-mouse IgG polyclonal antibody conjugated to horse radish peroxidase (Zymed) and Western Lighting® chemiluminescence reagents (PerkinElmer Life and Analytical Sciences, Waltham, Mass.). As shown in FIG. 3, SEAM 3 binds to the high molecular weight tetanus toxoid derivative running at the top of the gel. The tetanus toxoid derivative is referred to herein as "OS-tetanus toxoid" conjugate.

Example 9

Evaluating the Immunogenicity in CD1 Mice

OS-tetanus toxoid conjugates prepared above were used to evaluate immunogenicity in CD1 mice as follows. Groups of 10 female CD1 mice (6-8 weeks old, Charles River Laboratories, Wilmington, Mass.) were immunized with either 2 μg or 10 μg of total (i.e. N-acetyl plus de-N-acetyl) sialic acid OS-tetanus toxoid conjugate vaccine in 50% 0.9% saline/50% Freund's complete adjuvant (Pierce) emulsion by ip injection. Ten days after the first dose, blood samples were obtained by lancet of the submandibular vein and tested by ELISA using OS conjugated to bovine serum albumin (BSA, Pierce) (referred to as "DeNAc-BSA") prepared as described above for the OS-tetanus toxoid conjugate. Four weeks after the first dose, a second dose was given with Incomplete Freund's adjuvant (Pierce). Again, 10 days after the second dose, blood samples were obtained from the mice for testing.

FIG. 4 shows the mean titers for each group determined by ELISA using OS conjugated to bovine serum albumin (BSA, Imject, Pierce Chemical Co., Rockford, Ill.) as described in Example 14). The immune response to 2 μg and 10 μg doses were similar and increase approximately 100-fold between the primary and booster doses. The result shows that the vaccine is highly immunogenic and elicits an antigen-specific antibody response.

Example 10

Evaluating Functional Activity of Post-2$^{nd}$ Dose Antisera with *Neisseria Meningitidis* Group B Bacteria The ability of antibodies elicited by immunization with OS-tetanus toxoid conjugate vaccine to activate deposition of human complement components on NmB bacteria was determined as described by Welsch et al (Welsch et al, J Infec Dis, 2003, 188:1730). Briefly, the NmB strain NMB was grown to an OD620 nm of 0.6 in Muller-Hinton media containing 0.3% glucose. The cells were pelleted and washed with Dulbecco's PBS (Invitrogen, Carlsbad, Calif.) containing 1% (weight/volume) BSA (Sigma-Aldrich) (D-BSA) and resuspended in half the volume D-BSA of the original growth media. The bacteria (30 μl) were combined with the pooled antisera from mice immunized with either 2

μg or 10 μg was diluted to 1:20 or 1:200 in D-BSA. Human complement from a donor tested for the absence of antibodies to NMB was added to a concentration of 5% (volume/volume) in a total volume of 200 μl. The reaction was allowed to proceed for 30 minutes at ambient temperature with occasional agitation. The cells were pelleted, washed with 200 μl of D-BSA and FITC-conjugated sheep anti-human C3c antibody (BioDesign International, Saco, Me.) was added in D-BSA. After 30 minutes incubation on ice with occasional agitation, the cells were pelleted, resuspended in sterile filtered PBS buffer containing 0.5% (weight/volume) formaldehyde and analyzed by flow cytometry (BD FACSCalibur System, BD Biosciences, San Jose, Calif.). The results are shown in FIG. 5.

Figure 6:
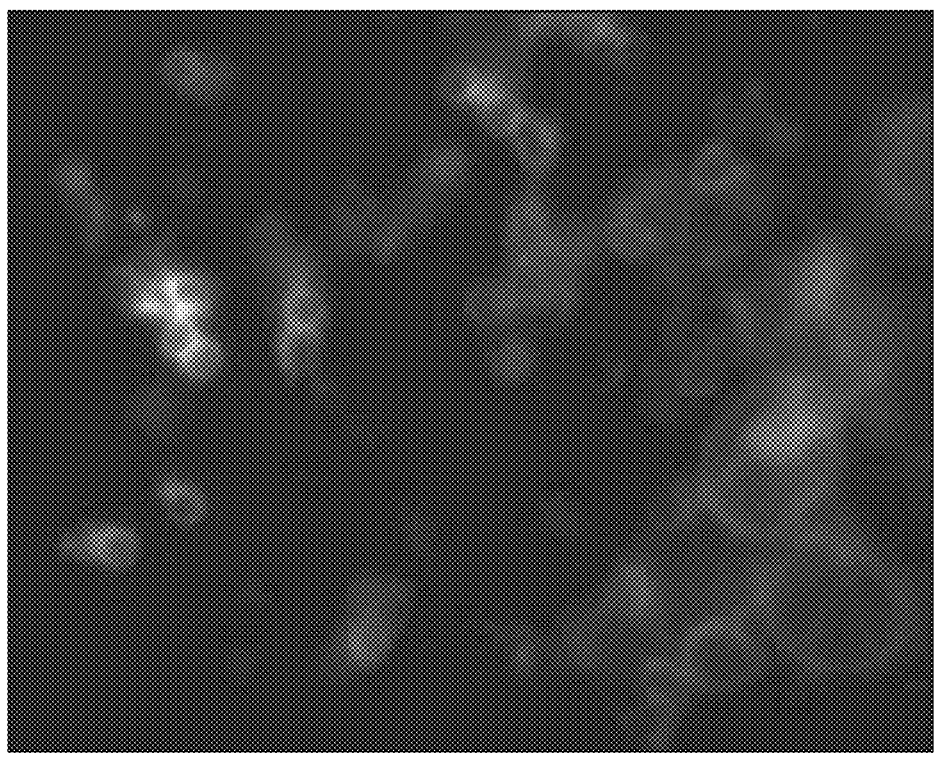

Deposition of complement components on the cell surface increases the fluorescence of the cells and is indicated by the shift in fluorescence peak to the right of the graph. The antibody activation is indicated by the lack of fluorescence of cells alone with active complement or antisera with heat-inactivated complement. The bacteria from flow cytometry were analyzed further by microscopy using a Zeiss Axioplan (Carl Zeiss, Inc.) fluorescence microscope. FIG. 6 shows a micrograph (200×) of bacterial cells after incubation with complement and pooled antisera diluted 1:200 from CD1 mice immunized with a 10 μg booster dose of the OS-tetanus toxoid conjugate vaccine stained with the FITC-conjugated sheep anti-human C3c antibody. In this cluster of cells, numerous highly fluorescent diplococci can be seen. The high level of fluorescence indicates the presence of complement factors that mediate bacteriolysis and opsonophagocytosis bound to the surface of the cells. In contrast, no fluorescent cells were observed in the negative controls (cells only with complement or antisera with heat inactivated complement). Activation of complement factor deposition on the cell surface of NmB bacteria is correlated with protection against disease caused by NmB (Welsch et al, J Infec Dis, 2003, 188:1730).

Figure 7:
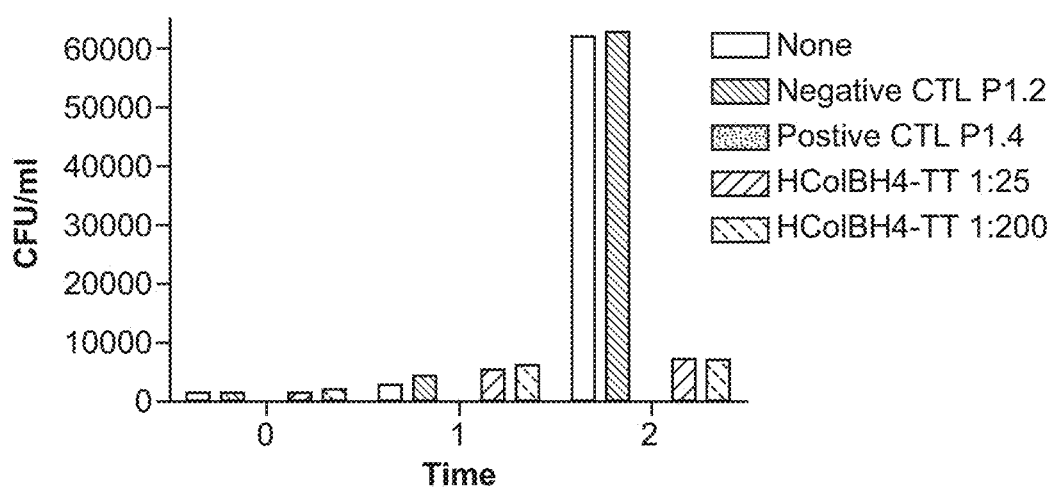

An alternative approach to evaluating the ability of antibodies elicited by a vaccine to protect against disease caused by NmB is to determine whether the antisera can lyse or inhibit the growth of NmB ex vivo in human blood. In this experiment, antisera (pooled antisera from CD1 mice immunized with 10 μg of OS-tetanus toxoid conjugate vaccine) and the test bacteria (approximately 1000 CFU of NmB strain NZ98/254 freshly grown in Muller-Hinton media as described above) are combined in freshly obtained human blood from a donor who lacks antibodies to the test strain in sterile glass vials. The blood is drawn from the donor with the thrombin inhibitor hirudin (50 mg/ml, 1 μl per ml of blood drawn, Refludan®, Berlex Laboratories, Montville, N.J.) in the syringe needle. Aliquots and diluted aliquots of the mixture are plated onto chocolate agar plates (Remel, Lenexa, Kans.) to determine the CFU/ml at the start of the experiment and at 1 hr and 2 hr intervals. The results of testing the antisera in the ex vivo human blood model of meningococcal bacteremia are shown graphically in FIG. 7.

In the absence of antibody or in the presence of 50 μg/ml of a negative control mAb anti-porin P1.2, an initial inoculation of about 1500 CFU increases to ~7000 CFU at 1 hr and ~60,000 CFU after 2 hrs. However, in the presence of 2 μg/ml of the positive control mAb, anti-porin P1.4, all of the bacteria are killed. Similarly, both 1:25 and 1:200 dilutions of the test vaccine antisera result in a decrease in the number of viable bacteria compared to the controls of 10-fold. While the CFU/ml at time 0 and at 1 hr are approximately the same as the negative control reactions, after 2 hrs no further growth of the bacteria is observed (~7000 CFU/ml). The result shows that the antibody activates protective mechanisms present in human blood (complement mediated bacteriolysis and/or opsonophagocytosis) that decreases the viability of the bacteria in human blood. Thus, antibodies elicited by the vaccine described herein have the potential to protect against disease caused by NmB.

Example 11

Figure 8:
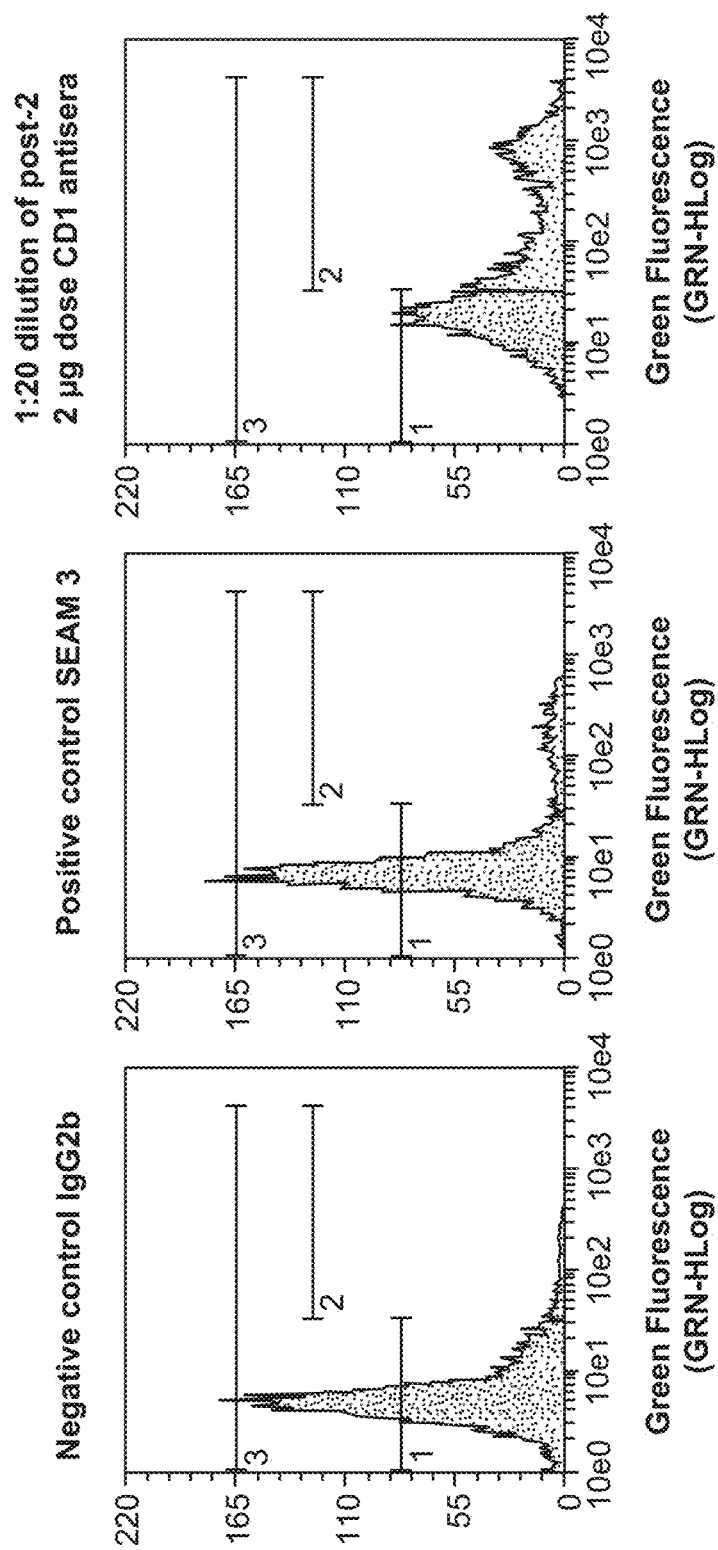

Binding of Vaccine Elicited Antibodies to PSA Derivatives Expressed by the Jurkat T-Cell Leukemia Cell Line SEAM 3 binds to neuraminic acid-containing PSA antigens expressed by the T-cell leukemia cell line Jurkat (U.S. Ser. No. 11/645,255 and PCT Application No. US2006/048850; incorporated herein by reference). To measure binding of antibodies elicited by OS-conjugate vaccine, Jurkat cells were spun at 1000×g for 5 minutes and fixed with ice-cold 1% (v/v) formaldehyde. After 20 minutes the cells were pelleted by centrifugation (as above) and incubated in a blocking solution of 3% (v/v) goat serum for 1 hour. After blocking, the pooled antisera from CD1 mice immunized with the 2 doses of 2 μg of total sialic acid OS-tetanus toxoid conjugate vaccine was added and incubated overnight at 4° C. The cells were washed twice by pelleting and resuspension in ice-cold PBS. Secondary antibody (FITC-conjugated goat anti-mouse IgG (Fab)$_2$, Jackson Immunoresearch, West Grove, Pa.) was incubated with the cells for at least 1 hour at 4° C. in the dark. After another series of spins and washes (3 times) binding was analyzed by a Guava EastCyte flow cytometer (Guava Technologies, Hayward, Calif.). Control samples were treated with an isotype matched irrelevant antibody (Southern Biotech, Birmingham, Ala.), which was used to create baseline fluorescence. The results of the Jurkat cell binding experiment are shown in FIG. 8.

Antibody binding to the cells is indicated by the shift to greater fluorescence (shift to the right of the histogram). Less than 5% of cells are positive for binding with the negative control irrelevant isotype matched IgG2b mAb. The positive control mAb SEAM 3 binding results in a small shift to higher fluorescence (mean fluorescence 210 AU) and 12% of the cells are positive for binding. Only a fraction of the cells are positive as the antigen is expressed on the surface of cells mainly during cell division. In contrast, binding of antibodies from the post-boost pooled antisera from the 2 μg dose of OS-tetanus toxoid conjugate diluted 1:20 results in a large increase in fluorescence (450 AU) and 35% of the cells are positive. Thus, the OS-tetanus toxoid conjugate vaccine elicits antibodies that are reactive with neuraminic acid-containing antigens expressed by Jurkat T-cell leukemia cells.

Example 12

Preparation of DeNac, NPrSia and TcAc Vaccine Antigens

De-N-acetyl poly α(2→8) neuraminic acid (DeNAc) PSA Colominic acid (100 mg, Sigma-Aldrich) and sodium borohydride (10 mg) were suspended in water (8.8 ml). After adding NaOH (1.8 ml of 50% solution; Thermo-Fisher) to a final NaOH concentration of 2M, the solution was heated to between 90° C. and 100° C. for 2 hrs. After cooling the solution to ambient temperature, 2M HCl was added to adjust the pH to 8. Precipitates were removed by centrifugation, the supernatant solution was dialyzed two times in 4 L of water (1 kDa Spectrum Spectra/Por* 7 dialysis membrane; Thermo-Fisher) and lyophilized. The resulting DeNAc antigen was determined to contain about 98% neuraminic acid residues (i.e., de-N-acetyl neuraminic acid or "Neu"), and contains a mixture of chains having a degree of polymerization of about 2-20.

N-Trichloroacetyl (TcAc) PSA DeNAc PSA (50 mg) was suspended in water (5 ml) and the pH adjusted to 8-9 with 2M NaOH. Trichloroacetyl chloride (Sigma-Aldrich) was added to the stirred solution in 5 0.1 ml aliquots over a period of 1 hr. The pH was maintained between 8 and 9 by adding 2 M NaOH. The reaction mixture was dialyzed in water and lyophilized as described above. The resulting TcAc antigen was determined to contain about 63% neuraminic acid residues, and contain a mixture of chains having a degree of polymerization of about 2-20.

N-propionyl (NPr) PSA and sialic acid-treated N-propionyl (NPrSia) PSA NPr PSA was prepared as described for TcAc PSA except that propionic anhydride (Sigma-Aldrich) was used in place of the acid chloride. The resulting NPr antigen was determined to contain about 21% neuraminic acid residues, and contain a mixture of chains having a degree of polymerization of about 30.

Exoneuraminidases are unable to degrade or degrade much slower PSA that contains neuraminic acid at the non-reducing end (T. Bhandari and G. Moe, unpublished). Therefore, a portion (20 mg) of NPr PSA was further treated with the exoneuraminidase SIALIDASE A (Prozyme) to increase the fraction of molecules that terminate at the non-reducing end in neuraminic acid. The polysaccharide was incubated with SIALIDASE A (10 al of 1 U/ml stock, Prozyme) in the 50 mM sodium phosphate buffer, pH 7 at 37° C. for two days. The reaction mixture was dialyzed in water and lyophilized as described above. The resulting NPrSia antigen was determined to contain about 7% neuraminic acid residues, and contain a mixture of chains having a degree of polymerization of about 2-20.

Example 13

Preparation of Tetanus Toxoid Conjugate (PS-TT) Vaccines

DeNAc, NPr, NPrSia, and TcAc antigens were oxidized with periodate and conjugated to tetanus toxoid (TT) as in Example 8 The PS-TT vaccine preparations (DeNAc-TT, NPr-TT, NPrSia-TT, TcAc-TT and OS-TT) were sterile filtered (0.22µ), aliquoted and stored at −80° C. until used. The composition of the vaccine solutions are summarized in Table 2. NeuNAc (N-acetyl neuraminic acid) and Neu (de-N-acetyl neuraminic acid) were determined by resorcinol assay as described in Example 6. The protein concentration was determined by BCA assay (Bio-Rad).

Figure 9:
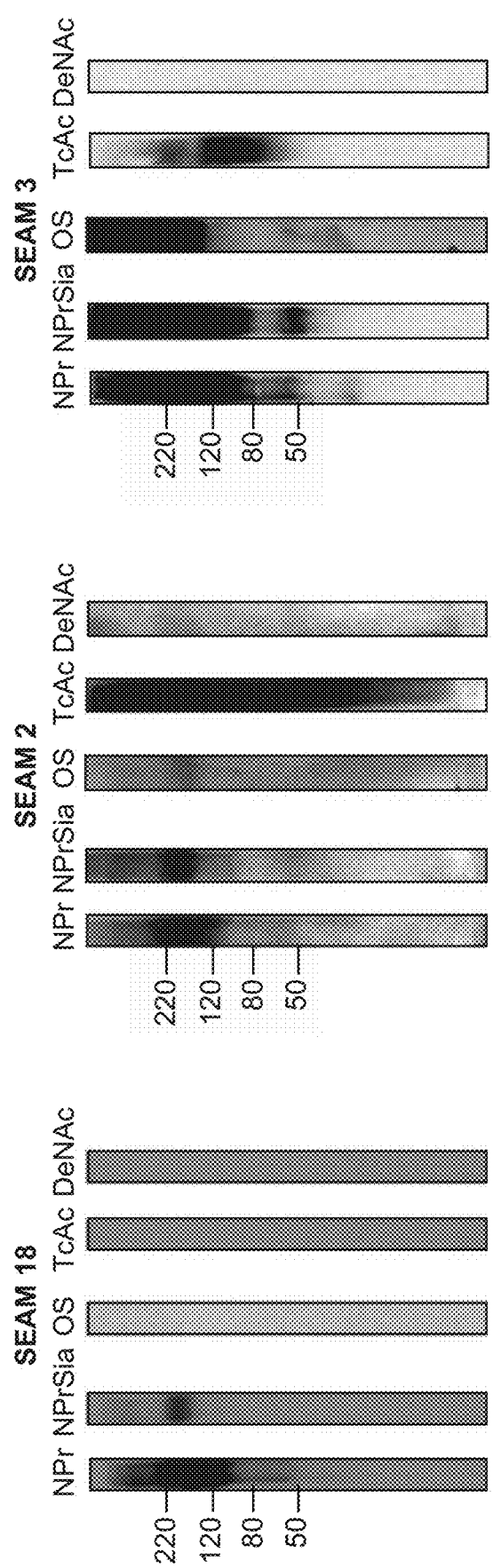

To demonstrate that the antigens were covalently linked to TT and to compare the reactivity of the conjugate vaccines with non-autoreactive mAbs SEAM 2 and 3 and autoreactive mAb SEAM 18 (Granoff et al., J. Immunol, 1998, 160: 5028), a portion of the vaccines were separated on a 4%-15% sodium dodecyl sulfate-polyacrylamide gel (Bio-Rad) and tested for reactivity with the mAbs by Western blot. Bound mAb was detected using a rabbit anti-mouse IgG polyclonal antibody conjugated to horse radish peroxidase (Zymed) and Western Lighting® chemiluminescence reagents (PerkinElmer Life and Analytical Sciences, Waltham, Mass.). As shown in FIG. 9, SEAM 2 binds to the TcAc-TT and NPr-TT conjugate vaccines (high molecular weight derivative running at the top of the gel), SEAM 3 binds to the NPr-TT and NPrSia-TT, and OS-TT conjugate vaccines, and SEAM 18 binds to the NPr-TT conjugate vaccine. None of the mAbs bind to the DeNAc-TT conjugate vaccine.

TABLE 2

NeuNAc, Neu, and protein composition of PS-TT vaccines.

| Vaccine | NeuNAc (mg/ml) | Neu (mg/ml) | Percent Neu | Total Sialic Acid (mg/ml) | Protein (mg/ml) |
|---|---|---|---|---|---|
| NPr-TT | 3.3 | 0.9 | 21 | 4.2 | 3.1 |
| NPrSia-TT | 4.2 | 0.3 | 7 | 4.5 | 3.1 |
| OS-TT | 2.4 | 1.2 | 33 | 3.6 | 2.4 |
| TcAc-TT | 2.2 | 3.7 | 63 | 5.9 | 3.6 |
| DeNAc-TT | 0.2 | 7.8 | 98 | 8 | 5.1 |

Example 14

Evaluating the Immunogenicity of PS-TT Vaccines in CD1 Mice

The immunogenicity of the PS-TT conjugates prepared in Example 13 was evaluated in CD1 mice as follows. Groups of 10 female CD1 mice (6-8 wk old, Charles River Laboratories, Wilmington, Mass.) were immunized with either 2 µg or 10 µg of total (i.e. N-acyl plus de-N-acetyl) sialic acid-TT conjugate vaccine in 50% 0.9% saline/50% Freund's complete adjuvant (Pierce) emulsion by ip injection. Blood samples were obtained by lancet of the submandibular vein 10 days after each injection and tested by ELISA.

Booster doses were given at post 28 days with incomplete Freund's adjuvant (Pierce) and titers of antisera obtained 10 days post immunization were evaluated. After 56 days post primary immuniation, the groups were split in half. Five mice from each group were given unconjugated PS and the other 5 conjugated PS, both without adjuvant. Since the immune response of the mice that had received the unconjugated PS was very weak, they were given a dose $3^{rd}$ dose of conjugate without adjuvant 112 days post primary immunization. Antisera from this fourth dose are designated 3-PS throughout, where 3 indicates the $3^{rd}$ immunization.

FIG. 10 shows the mean titers for each group determined by ELISA. The antibody titer elicited by the PS-TT vaccines was measured by ELISA using PS conjugated to BSA (PS-BSA) prepared as described above for the PS-tetanus toxoid conjugates (Example 8). Initially, antiserum from each mouse was tested individually, but since the titers were similar for all mice in the group, the antisera individual mice in each group were pooled and all further experiments were done with the pooled antisera. ELISA plates were prepared by diluting each PS-BSA conjugate 1:200 in PBS and adding 100 µl per well to a 96-well microtiter plate (Immulon IIHB). The plates were stored overnight at 4° C. before use. The plates were washed with PBS buffer 5 times and blocked with PBS buffer containing 1% (w/v) of BSA (blocking buffer) for 1 hr at ambient temperature. The antisera were added in blocking buffer at 1:100 dilution, followed by serial 3-fold dilutions. After overnight incubation at 4° C., the plates were washed with PBS buffer 5 times and rabbit anti-mouse-alkaline phosphatase conjugate antibody (Zymed) diluted 1:3000 in blocking buffer was added. After incubating an additional hour, the plates were washed (5×) with PBS buffer and the bound antibody was detected by adding 1 mg/ml p-nitrophenyl phosphate substrate (Sigma-Aldrich) in 50 mM sodium carbonate buffer, pH 9, containing 1 mM $MgCl_2$. The absorbance at 405 nm after 1 hr incubation at ambient temperature was measured using a BioRad Model 550 microtiter plate reader. Antisera were tested against the homologous antigen PS-BSA conjugate and against DeNAc-BSA.

FIG. 10 (upper panel) shows the titers for each group of pooled antisera against the homologous antigens and DeNAc PSA after each immunization as measured by ELISA. The titers for homologous antigens varied widely. For all vaccines, the titer elicited by the 10 µg dose was higher than that elicited by the 2 µg dose but did not increase after the second dose. The relative titers against homologous antigens were consistent for both dosages and for all post primary immunizations. The order of decreasing immunogenicity for homologous antigens was NPrSia>DeNAc>OS>TcAc, NPr. The TcAc-TT and NPr-TT vaccines elicited very low titers against the homologous antigens that did not increase after booster doses (FIG. 10).

The reactivity of the pooled antisera from each dose for the DeNAc-BSA antigen was also evaluated by ELISA. All of the PS-TT vaccines contained some fraction of Neu residues (Table 2) and all five vaccines elicited titers greater than >10,000 against DeNAc-BSA (FIG. 10, lower panel) that did not increase after the second immunization (FIG. 10). Even though the amount of Neu in each PS-TT vaccine and in each dose varied over a wide range (from ~0.3 µg/dose to ~10 µg/dose), all vaccines at both doses elicited anti-DeNAc titers of roughly the same magnitude. None of the antisera was reactive against unmodified PSA by ELISA (titer <1:50). The result suggests that the zwitterionic Neu component of all of the antigens is immunogenic and is the immunodominant determinant of the PS-TT vaccines.

Example 15

Figure 11A:
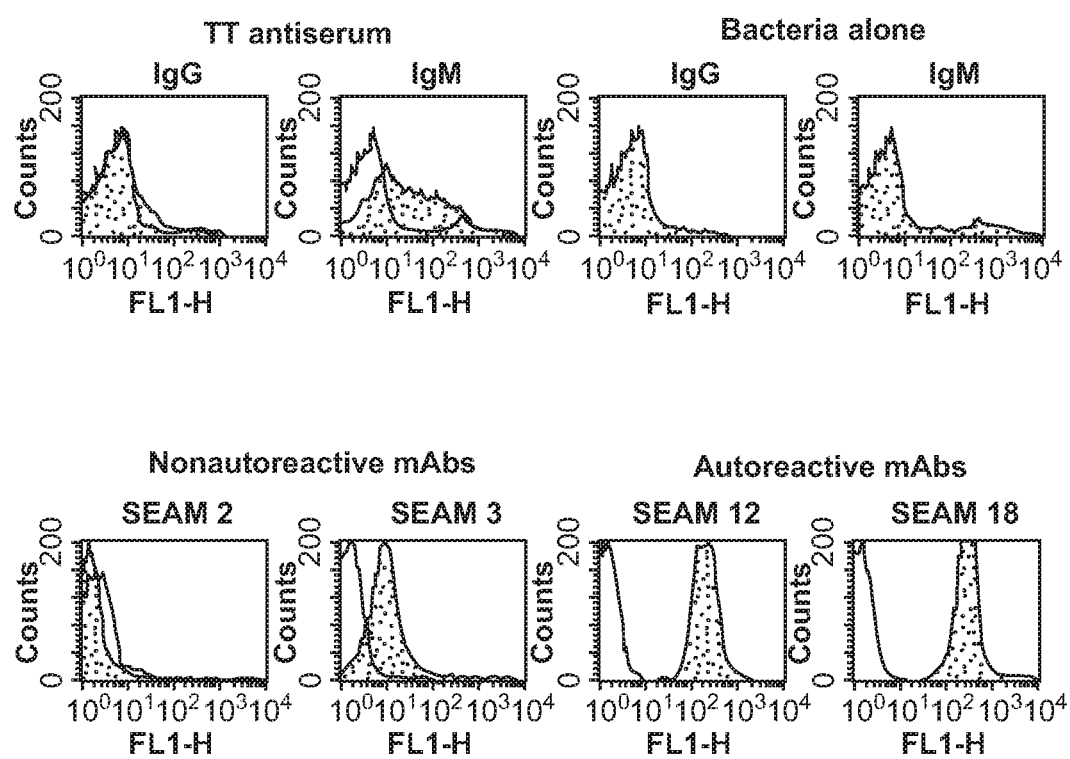
Figure 11A:
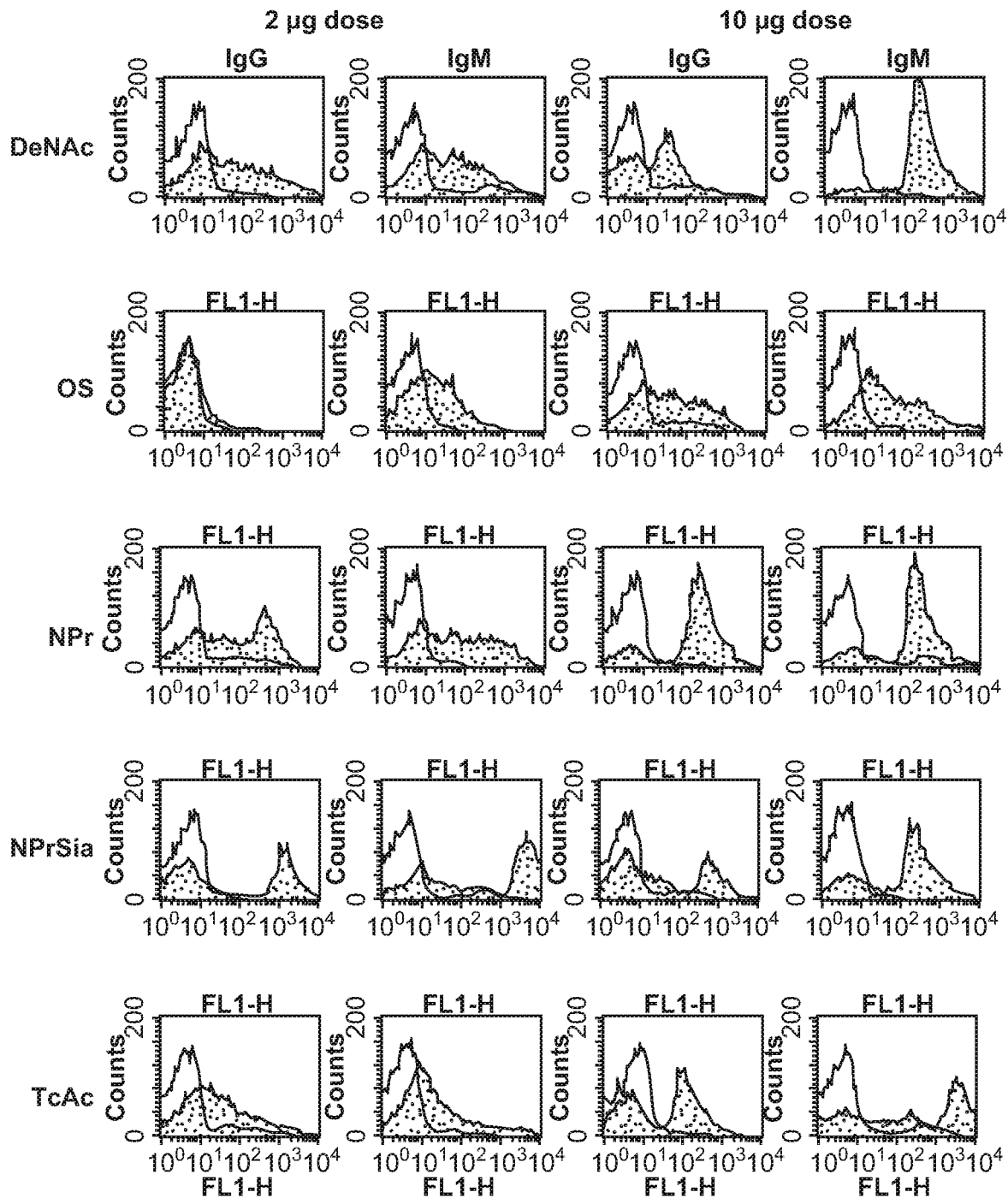

Evaluating Binding of PS-TT Antisera to *Neisseria Meningitidis* Group B (NmB) Bacteria The ability of the PS-TT vaccines to elicit antibodies that bind to NmB was tested by flow cytometry. The NmB strain NMB was grown to an $O.D._{620}$ of 0.6 in Mueller-Hinton media containing 0.3% glucose. The cells were pelleted, washed, and resuspended in 80% of the original volume in blocking buffer. The resuspended bacteria were added to the reaction mixture such that the final concentrations were 50% resuspended bacteria, 10% antiserum, and 40% blocking buffer. The mixture was incubated at 4° C. for 2 hr with periodic gentle agitation. The cells were pelleted and resuspended in 100 µl of a 1:300 dilution in blocking buffer of fluorescein isothiocyanate (FITC)-conjugated goat antimouse secondary antibodies. FITC-conjugated antibodies against IgG(H+L) $F(ab')_2$ and IgM (Jackson ImmunoResearch, West Grove, Pa.) as well as IgG1, IgG2a, IgG2b, and IgG3 (Bethyl Laboratories, Montgomery, Tex.) were used. After the secondary antibody was added, the tubes were incubated for 1 hr at 4° C. with periodic gentle agitation. The cells were pelleted and resuspended in 450 µl of PBS containing 0.5% formaldehyde (weight/volume), freshly made and filtered. The samples were immediately analyzed by flow cytometry (BD FACSCalibur System, BD Biosciences, San Jose, Calif.). As shown in FIG. 11A, all of the PS-TT vaccines except for the OS-TT 2 µg dose elicited both IgG and IgM antibodies after the third dose that bound to strain NMB. Although binding appeared to be relatively poor in some cases, binding by the "paradigm" mAbs SEAM 2 and 3 is also poor compared to the autoreactive mAb SEAM 12, which binds to the bacteria very strongly (FIG. 11A). The reasons for the apparently complex binding characteristics of two mAbs (SEAM 2 and 3) that are nonetheless protective have to do with the distinctive characteristics of the antigens recognized by the mAbs. Both SEAM 2 and 3 apparently recognize antigens that are non-capsular and are neither highly nor uniformly expressed over the entire surface of the bacteria. Immunization with the carrier tetanus toxoid protein alone also elicited polyreactive IgM but not IgG antibodies that could bind to NMB (FIG. 11A). In general, the 10 µg dose PS-TT antisera bound more strongly to the bacteria than the 2 µg dose antisera. The exception was NPrSia-TT, in which the pattern was reversed. IgG binding was somewhat stronger in the 10 µg dose antisera than the 2 µg, and the difference was even more pronounced with IgM.

Figure 11B:
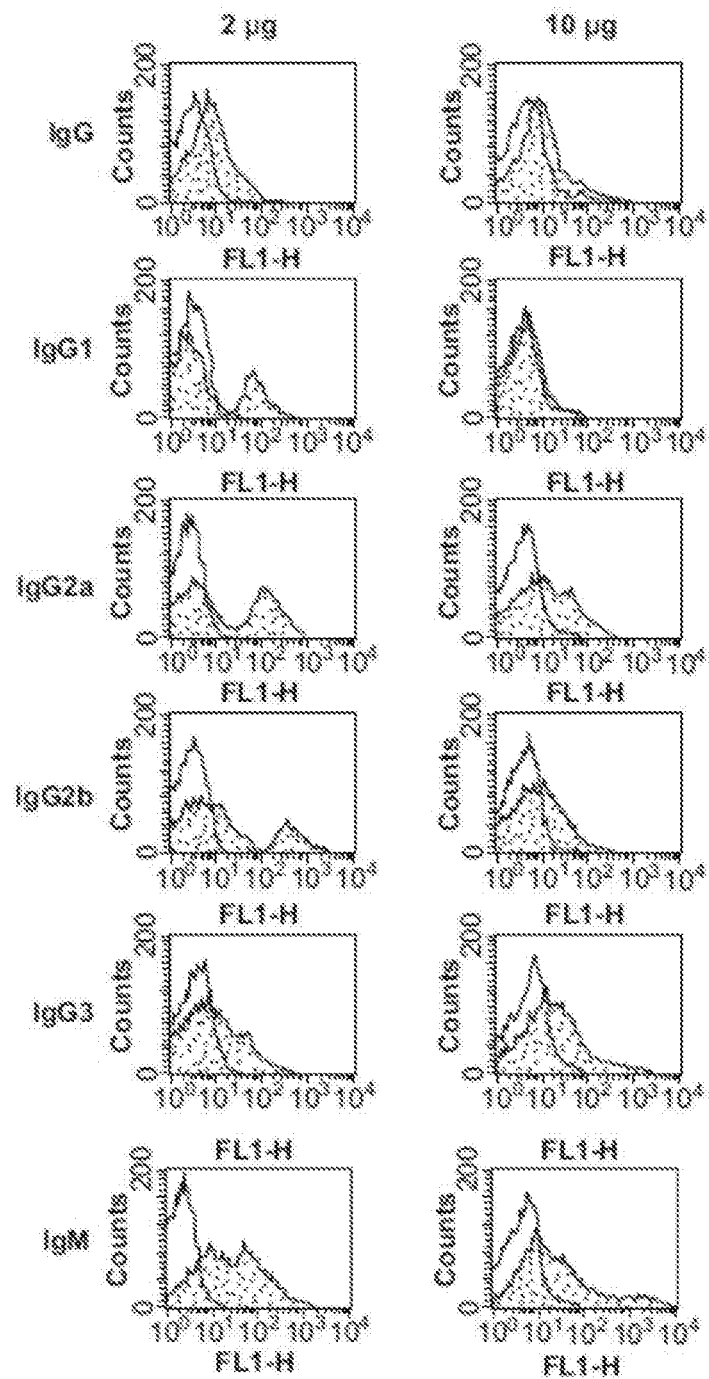

Some of the PS-TT antisera were further analyzed to determine which IgG subclasses bound to the bacteria. Representative data obtained with DeNAc-TT antisera is shown in FIG. 11B. With the exception of IgG1, all the antisera contained antibodies of all IgG subtypes that bound to the bacteria. DeNAc-TT (shown) was the only antiserum that contained IgG1 Ab. The amounts of bound IgG2a, IgG2b, and IgG3 were roughly the same. Since the antisera were all pooled samples of 5 mice each, it is possible that there could have been individual differences in the prevalence of IgG2a, IgG2b, and IgG3 Ab that were obscured by the pooling. The above results demonstrate that all of the PS-TT vaccines elicited anti-Neu-containing PSA antibodies and all of them were reactive with group B strain NMB.

Example 16

Figure 12A:
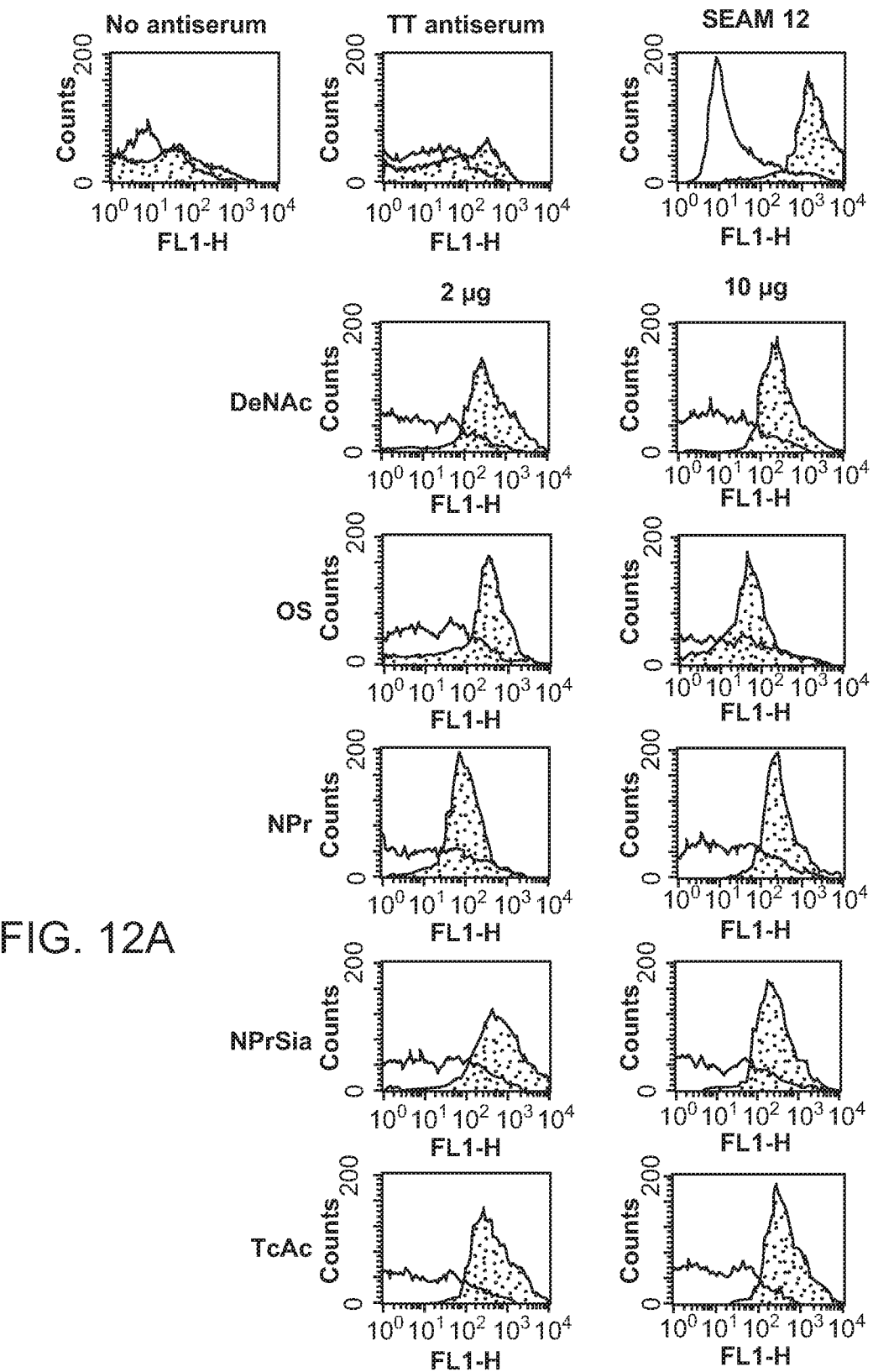
Figure 12B:
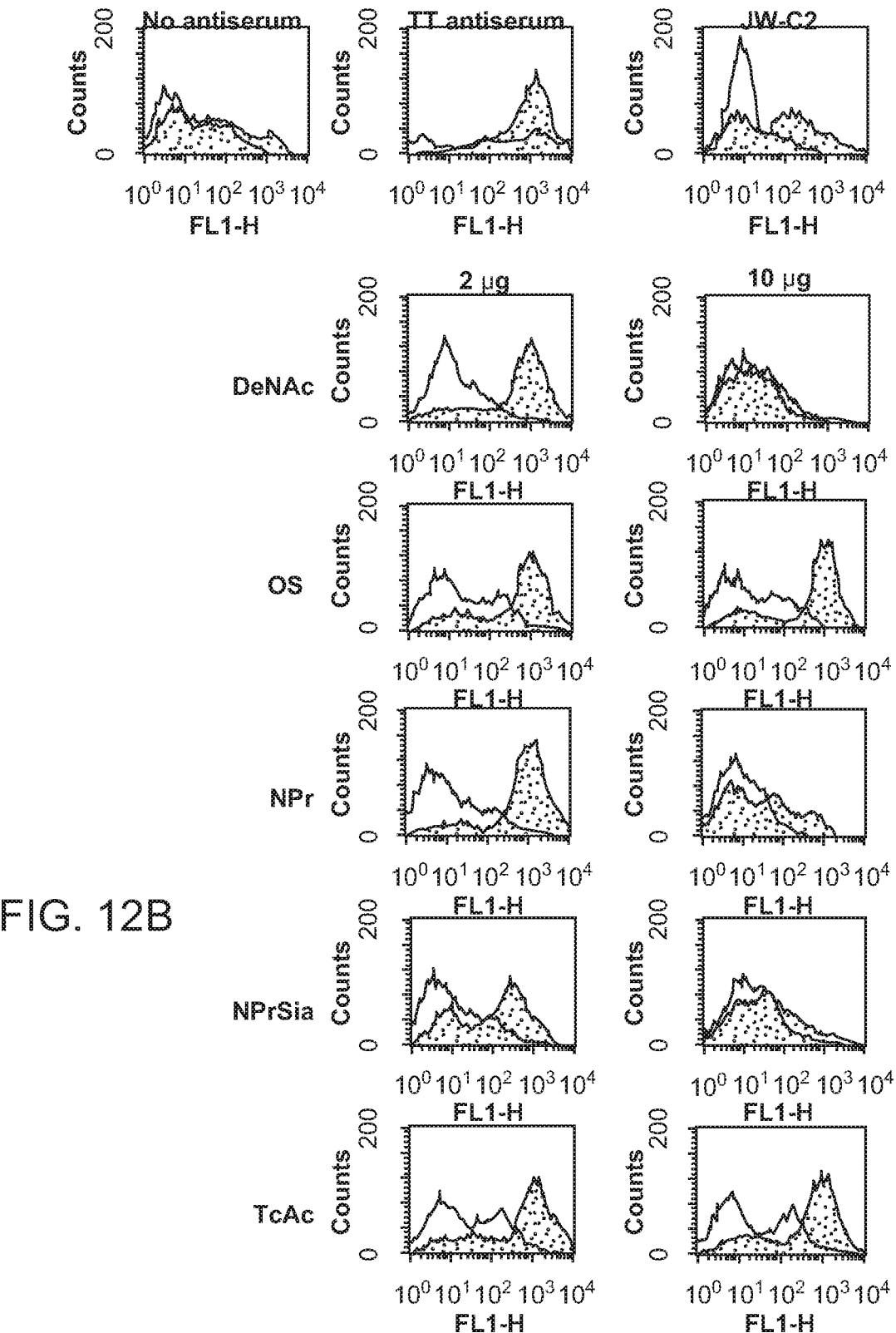

Evaluating Functional Activity of PS-TT Antisera with *Neisseria Meningitidis* Group B, C, X, Y, W135 Bacteria Activation of complement protein deposition. The ability of antibodies elicited by immunization with PS-TT conjugate vaccine antisera to activate deposition of human complement components on *Neisseria meningitidis* groups B, C, X, Y, and W135 bacteria was determined as described in Example 10. The results are shown in FIG. 12 FIGS. 12A and 12B.

Deposition of complement components on the cell surface increases the fluorescence of the cells and is indicated by the shift in fluorescence peak to the right of the graph. The antibody activation is indicated by the lack of fluorescence of cells alone with active complement or antisera with heat-inactivated complement.

The results demonstrate that all the antisera strongly activated complement deposition on NmB, and there was little difference in the amount of complement deposited between the antisera elicited by different antigens or 2 µg and 10 µg doses (data not shown). The consistency of complement activation is in accordance with the similarity seen in the anti-deNAc titers. It suggests that all the antigens were equally effective, and increasing the dose of PS did not increase the anti-Neu PSA antibody responses of the vaccines.

Recently, we discovered that SEAM 2, 3 and 18 (Granoff et al Id.) antibodies are reactive with and have functional activity against meningococcal strains from serogroups A, C, W135 as well as B (Flitter, B A and Moe, G R, unpublished). Therefore, we also measured the ability of the antisera to activate complement protein deposition on strains representative of all *N. meningitidis* serogroups. At least one of the antisera pools was able to activate complement protein deposition on group A, B, C, X, Y, or W135 strains. In particular, the 2 µg or 10 µg antisera pools activated complement protein deposition on group A, B, C, X and Y strains but not on W135 strains. Only the NPrSia antisera pools showed activity against group W135 strains. The results from the control tetanus toxoid only antisera were uninterpretable since the antisera had a very high background signal with heat inactivated complement, particularly with group C, Y and W135 strains. In contrast, all of the complement activation activity observed with the PS-TT conjugate vaccine elicited antisera was dependent on active complement.

The results suggest that all *Neisseria meningitidis* strains regardless of capsular group either express or acquire exogenously poly alpha (2→8) PSA antigens likely containing Neu and that vaccines eliciting anti-NeuPSA antibodies may be protective against disease caused by all meningococcal group strains, as activation of complement factor deposition on the cell surface of *N. meningitidis* bacteria is correlated with protection against disease (Welsch et al, J Infec Dis, 2003, 188:1730).

Serum Bactericidal Activity. Complement-mediated bactericidal activity was measured with *N. meningitidis* group B strain NMB and group C strain 4243 as follows. After overnight growth on chocolate agar (Remel), several colonies of *N. meningitidis* were inoculated into in Mueller-Hinton broth (starting $A_{620nm}$ of ~0.1) and the test organism was grown for approximately 2 hrs to an $A_{620nm}$ of ~0.6. After washing the bacteria twice in D-BSA approximately 300 to 400 CFU were added to the reaction mixture. The assays were performed with human complement from a donor that lacks bactericidal activity against the test strain in the absence of added antibody up to 40% complement. The final reaction mixture of 40 µL contained 20% (v/v) complement, antisera diluted in D-BSA buffer. CFU/ml in the reaction mixtures were determined after overnight growth on chocolate agar (Remel). Bactericidal titers or concentrations were defined as the serum dilution resulting in a 50% decrease in colony forming units (CFU) per ml after 60 minutes incubation of bacteria in the reaction mixture, compared to the control CFU per ml at time 0. Typically, bacteria incubated with the negative control antibody and complement showed a 150 to 200% increase in CFU/ml during the 60 minutes of incubation.

Although the PS-TT antisera were able to activate complement protein deposition on group B bacteria, none of the antisera were able to mediate bacteriolysis in the presence of complement. The mechanistic reasons for this are unknown, but similar functional characteristics are observed for the protective, non-autoreactive mAb SEAM 3 (Granoff et al., J. Immunol, 1998, 160: 5028; Moe et al., Infect. Immun. 2005, 73:2123). In contrast, the antisera pools for NPr, DeNAc, and TcAc (all 2 µg dose post 3rd injection) exhibited high titers against the group C strain showing that antibodies elicited by the vaccines can mediate complement-dependent bacteriolysis, which is the hallmark of protection against meningococcal disease (Goldschneider et al, J. Exp. Med., 1969, 129:1327).

TABLE 3

Serum bactericidal activity of PS-TT antisera pools against NmC strain 4243 with human complement.

| Antisera (2 µg dose) | 1/Titer | | |
|---|---|---|---|
| | Expt. 1 | Expt. 2 | Expt. 3 |
| TT alone | <8 | <8 | <16 |
| OS-TT | <8 | <8 | <16 |
| NPrSia-TT | <8 | <8 | <16 |
| NPr-TT | >256 | >256 | 2048 |
| DeNAc-TT | 256 | 96 | 8192 |
| TcAc-TT | >256 | 128 | 6144 |

Passive Protection in Infant Rats. Infant (4-6 days) Wistar rats were taken from the mothers and randomly divided into groups of 5 rats each. Each pup was given 100 µl of antiserum diluted 1:10 in sterile PBS containing 1% BSA (PBS-BSA) intraperitoneally and then returned to their mothers while the challenge bacteria were prepared. NmB strain M986 or NmC strain 4243 was grown to $O.D._{620}$ 0.6 in Mueller-Hinton broth with 0.3% glucose, washed, resuspended in PBS-BSA, and diluted to $10^4$ CFU/ml. Each rat pup was given 100 µl of bacteria, so the final challenge dose was ~1000 CFU/rat. The pups were returned to their mothers. The next day, the pups were anesthetized with isoflurane and blood was obtained by cardiac puncture using a heparanized needle. The animals were euthanized by $CO_2$ anoxia, and 100 µl, 10 µl, and 1 µl of the blood was plated on chocolate agar (Remel). The plates were incubated at 37° C., 5% $CO_2$ overnight then the colonies were counted.

Some of the PS-TT antisera were protective or partially protective against NmB or NmC bacteremia in the infant rat model of passive protection (FIG. 13). Protection was calculated by comparing the geometric mean CFU/ml of the vaccine-elicited antisera to the geometric mean CFU/ml of the antisera from mice immunized with the TT carrier protein alone. Four of the PS-TT antisera pools provided passive protection against strain M986 that was different from the TT antiserum. The antisera included NPrSia-TT 10 µg, DeNAc-TT 2 µg (p<0.05), NPr-TT 2 µg, and OS-TT 2 µg (p<0.01).

The 2 µg doses tended to be more protective than the 10 µg doses, although the difference was not quite significant (p=0.052). If the NPrSia-TT antiserum, which shows the opposite pattern, is removed from the analysis, the 2 µg doses were significantly more protective than the 10 µg doses (p=0.013). NPrSia-TT may be an exceptional antiserum. It is the only one in which the 10 µg doses bound more strongly to the bacteria than the 2 µg, and the NPrSia-TT vaccine formulation contained by far the least amount of neuraminic acid. It is possible that the NPrSia-TT 2 µg dose formulation simply did not contain enough neuraminic acid residues to elicit strong binding and protective antibodies. For the other PS-TT vaccines, the amount of Neu in the 2 µg dose appears to be sufficient to elicit the maximum anti-NeuPS antibody responses and the 10 µg dose did not convey any additional benefit.

Passive Protection in an Ex Vivo Human Blood Model of Meningococcal Bacteremia.

Figure 14:
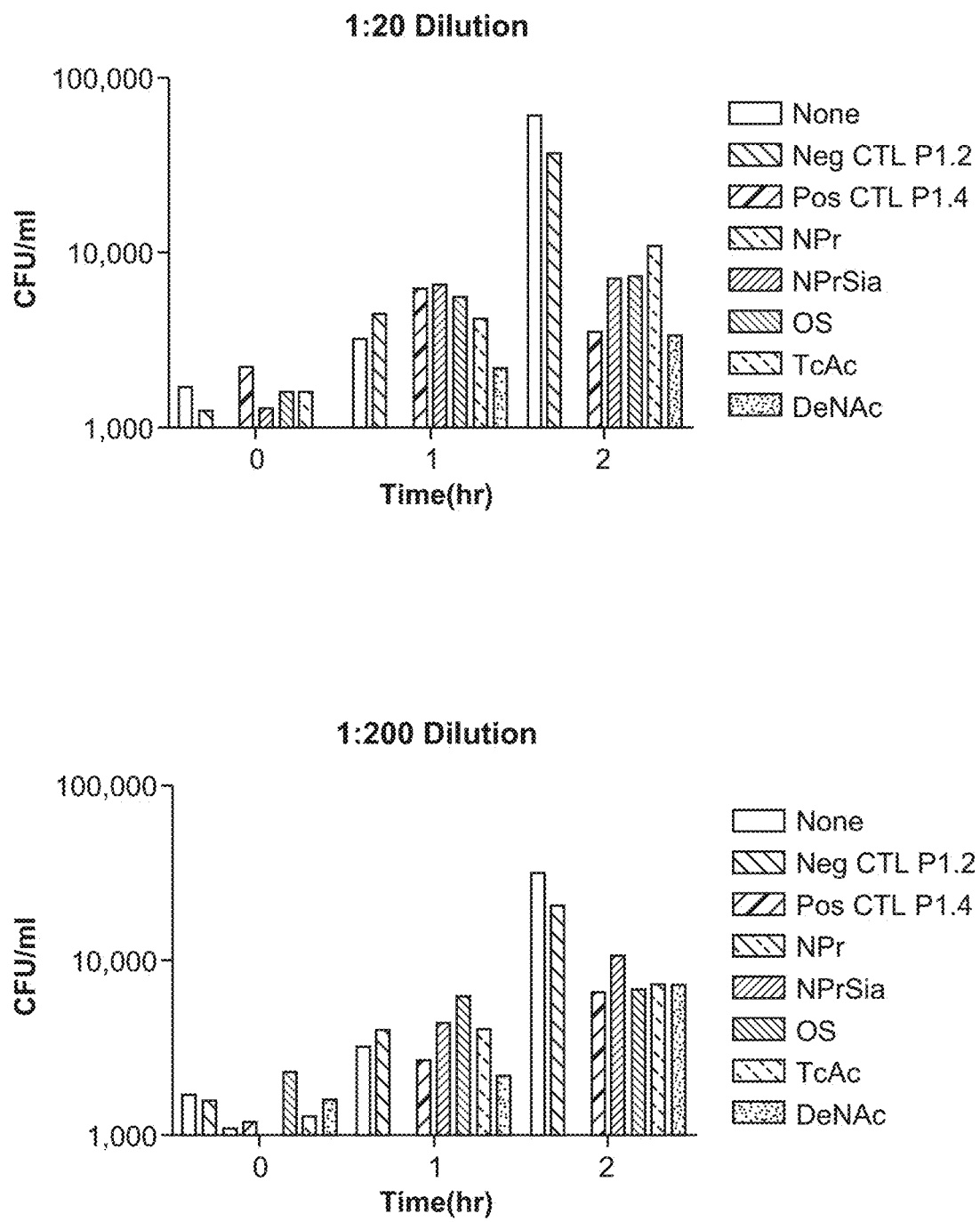

As note above in Example 10, an alternative approach to evaluating the ability of antibodies elicited by a vaccine to protect against disease caused by NmB is to determine whether the antisera can lyse or inhibit the growth of NmB ex vivo in human blood. Antisera (pooled antisera from CD1 mice immunized with 10 µg of PS-TT conjugate vaccines as described in Example 15) and the test bacteria (approximately 1000 CFU of NmB strain NZ98/254 freshly grown in Muller-Hinton media as described in Example 15 above) were combined in freshly obtained human blood from a donor who lacks antibodies to the test strain in sterile glass vials and prepared and tested as described in Example 15. The results of testing the antisera in the ex vivo human blood model of meningococcal bacteremia are shown graphically in FIG. 14, and are similar to the results of Example 15. Thus, antibodies elicited by the PS-TT vaccines described herein support application of the vaccines for protection against disease caused by N. meningitidis bacteria expressing a de-N-acetylated sialic acid (deNAc SA) epitope.

Example 17

Figure 15:
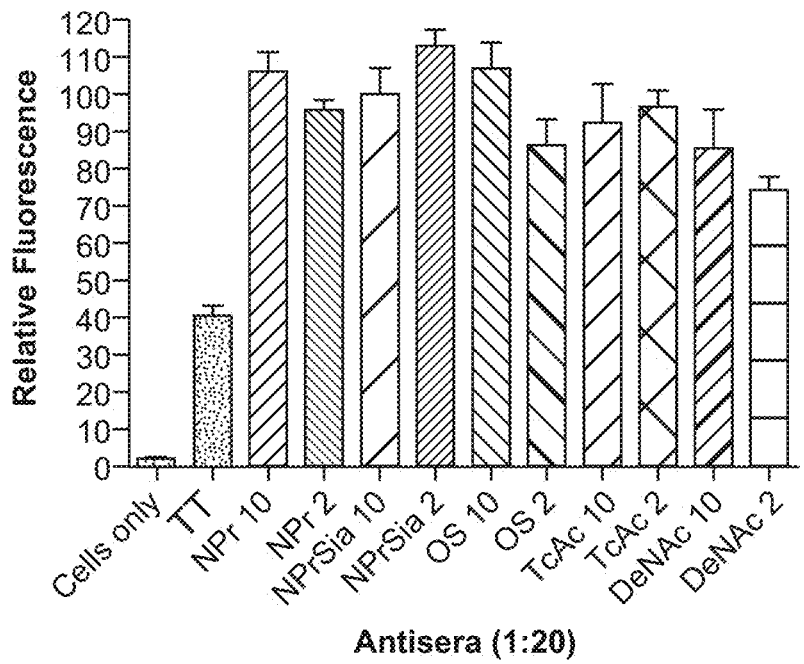

Binding of Vaccine Elicited Antibodies to PSA Derivatives Expressed by the Jurkat T-Cell Leukemia Cell Line To measure binding of antibodies elicited by the PS-TT conjugate vaccines prepared in Example 13, Jurkat cells were tested as described in Example 11 except that after blocking, pooled antisera from CD1 mice immunized with the 3 doses of 2 µg of total sialic acid PS-TT conjugate vaccine was added and incubated overnight at 4° C. The results of the Jurkat cell binding experiment are shown in FIG. 15. Although there is a small amount of non-specific binding of the TT negative control antisera compared to the cells only, all of the antisera pools showed strong binding to Jurkat cells as indicated by the increase in fluorescence of the gated cells. Thus, the results confirm that the PS-TT conjugate vaccines elicit antibodies that are reactive with neuraminic acid-containing antigens expressed by Jurkat T-cell leukemia cells.

Example 18

Activation of Complement Deposition by Vaccine Elicited Antibodies on Jurkat T-Cell Leukemia Cells, SK-MEL 28 Melanoma, and CHP-134 Neuroblastoma Cells Activation of complement-mediated cytotoxicity is an important mechanism for antibody dependent killing of cancer cells (Maloney et al, Semin Oncol, 2002. 29(1 Suppl 2):2). Therefore, the ability of PS-TT antisera to activate deposition of human complement proteins on CHP-134 neuroblastoma, Jurkat T-cell leukemia, and SK-MEL 28 melanoma cells was measured by flow cytometry.

Cells (approximately $10^5$ per well) were plated onto a flat bottom 96-well tissue culture plate (Nunc) and incubated with growth medium overnight before assay. Cells were detached from the plate (Jurkat cells are non-adherent) by either trypsin (SK-MEL-28) or Cell Dispersal Reagent (CDR, Guava Technologies) (CHP-134) before being collected into a 96-round bottom plate (Falcon), spun at 1000×g for 5 minutes, the supernatant was removed and the cells were resuspended in a 1:10 dilution of the PS-TT or TT (negative control) antisera (2 µg dose) or no antisera in 95 µl of standard cell culture medium (RPMI-1640 growth medium supplemented with 10% fetal bovine serum). Human complement (5 µl) from a donor with no intrinsic activity against the cancer cell lines was added and mixed. After 30 minutes at ambient temperature, the cells were pelleted by centrifugation (above), washed with PBS buffer and suspended in PBS buffer containing a 1:100 dilution of FITC-conjugated sheep anti-human C3c antibody (BioDesign International). After 30 minutes incubation at ambient temperature, the cells were pelleted and washed as before and finally resuspended in PBS buffer containing 1% formaldehyde. The relative fluorescence of the cells was using a Guava EastCyte flow cytometer (Guava Technologies). Control samples which contained no antisera, were used to establish baseline fluorescence.

Figure 16:
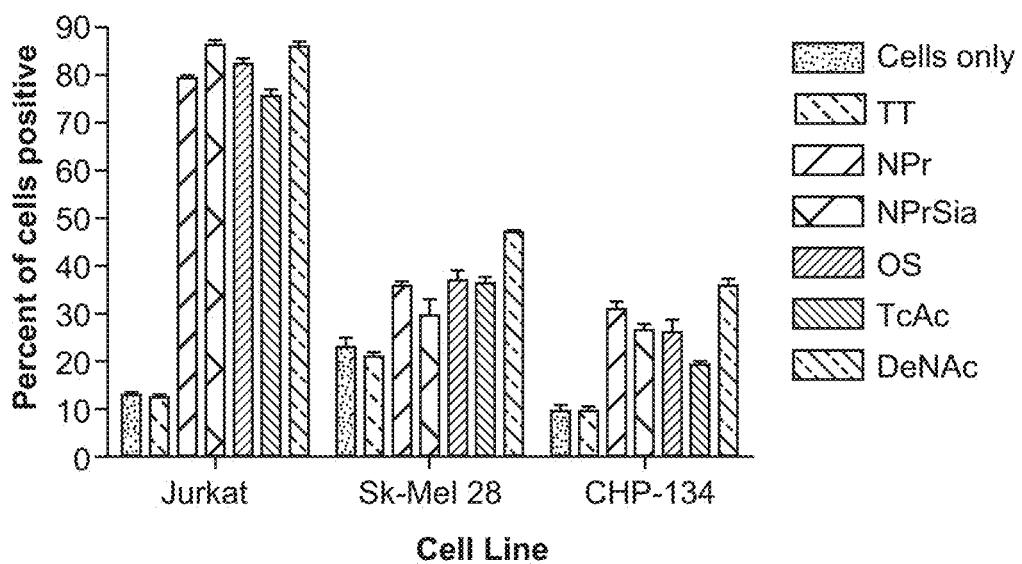

All of the PS-TT test antisera, but not the control TT only antisera, was able to activate complement protein deposition on all three cell lines (FIG. 16).

Example 19

Effect of Vaccine Elicited Antibodies on the Viability of Jurkat T-Cell Leukemia Cells The effect of PS-TT antisera on the viability of the human T-cell leukemia Jurkat cell line in culture was measured using a cell viability assay. Cells were incubated with a 1:20 dilution of the antisera for 24 hours. Jurkat cells were incubated at a concentration of $2\times10^5$ cells/ml in round-bottom 96-well plates (Falcon), 200 µl/well. Plates were then spun at 1,000×g for 5 minutes. The cells were resuspended in Guava ViaCount reagent and read on a Guava EasyCyte flow cytometer, using the Guava ViaCount assay (all from Guava Technologies).

Figure 17:
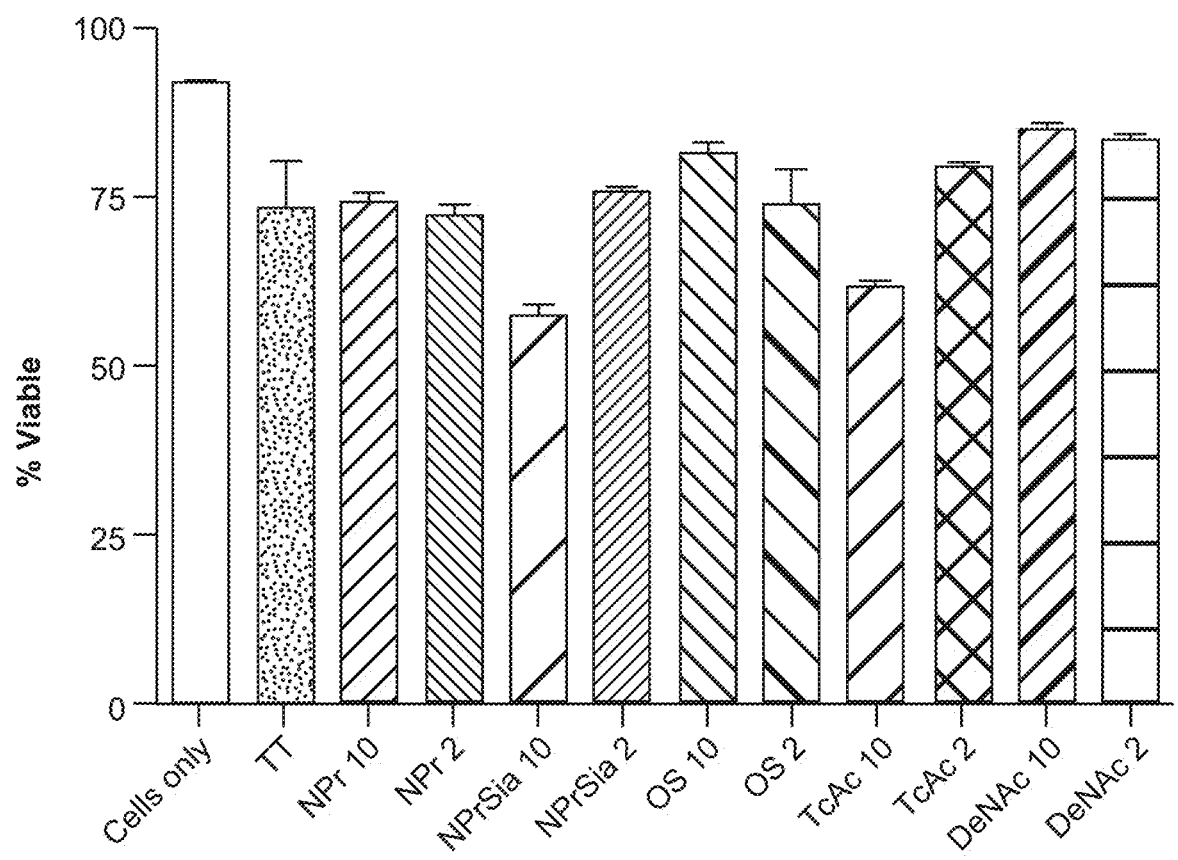

As shown in FIG. 17, antibodies elicited by the NPrSia-TT and TcAc-TT vaccines were able to reduce the viability of Jurkat cells.

Example 20

Immunohistochemical Analysis of TcAc-TT Vaccine Elicited Antibodies Binding to Antigens Expressed in Primary Human Cancers Cancer cell lines are clonal but can undergo changes when passaged many times in cell culture. Therefore, it is important to demonstrate that antigens recognized by antibodies elicited by the PS-TT vaccines are also present in primary human tumors. Also, for an immunotherapeutic approach to be useful, it is important that the antigens targeted are either not expressed or expressed at greatly reduced levels in normal tissues. Since the TcAc-TT antisera exhibited the greatest overall functional activity against meningococcal bacteria and Jurkat cells, the reactivity of the antisera with normal and cancerous tissues was evaluated by immunohistochemistry (IHC).

Frozen, unfixed tissue arrays containing 28 normal and cancer tissues including normal brain, breast, colon, skeletal muscle, kidney, liver, lung pancreas, prostate, skin, small intestine, stomach, ovary, and uterus and malignant tumors from the same tissues were obtained from BioChain Institute, Inc. (Hayward, Calif.). The slides were rinsed with PBS buffer then briefly washed with cold (−20° C.) acetone. Endogenous peroxidases were blocked by incubation with PEROXIDAZED 1 (Biocare Medical, Concord, Calif.) followed by washing with PBS buffer and blocked with 2.5% (volume/volume) normal horse serum (Vector Labs, Burlingame, Calif.) for 30 min. TT control and TcAc-TT antisera (2 µg dose) diluted in DA VINCI GREEN (Biocare Medical) were added and the slides incubated in a humid chamber overnight at 4° C. Unbound antibody was removed by buffer rinses. Bound antibody was then detected using AEC substrate (Vector Labs) following the manufacturer's directions. After additional washes, nuclei were counterstained using Mayer's hematoxylin QS (Vector). Finally, the slides were mounted in aqueous mounting medium (VECTRA-MOUNT™ AQ, Vector) and viewed using a Zeiss Axioplan microscope.

The TT and TcAc-TT antisera showed no or weak staining to the normal tissues and the TT antisera was not reactive with any of the tumor tissues. However, TcAc-TT antisera showed clear staining of skin melanoma metastasized to brain and adenocarcinomas of the pancreas, stomach, ovary, and uterus, and a renal cell carcinoma. An example comparing the TT and TcAc-TT staining of normal ovary and ovarian adenocarinoma is shown in FIG. 18. The results show that the antigens reactive with antibodies elicited by the TcAc-TT vaccine are expressed in only or at higher levels in several primary human tumors but not in normal human tissues.

Example 21

Production of Monoclonal Antibodies Using the DeNac-TT Conjugate Vaccine

Four to six weeks old female CD1 mice were immunized with the DeNAc-TT vaccine as described in Example 14. Three days after the $3^{rd}$ dose, mice were sacrificed and their spleen cells were fused with myeloma cells P3X63-Ag8.653 at a ratio of 5 spleen cells to 1 myeloma cells. After two weeks incubation in HAT selective medium, hybridoma supernatants were screened for antibody binding activity by ELISA, performed on microtiter plates coated with the DeNAc-BSA derivative (Example 9). A large number of positive wells (250) were identified. Cell culture supernatants from the DeNAc-BSA positive wells were then subjected to a second screen based on the ability of the antibody in the supernatant to activate complement deposition on Jurkat cells as described in Example 18. Of the original 250 DeNAc-BSA positive wells 11 were also positive for complement activation. Five (5) of the 11 hybridomas were cloned twice by limiting dilution and then expanded and frozen for subsequent use in tissue culture.

The subclasses of the monoclonal antibodies were determined using a mouse monoclonal antibody isotyping kit (Southern Biotech, Birmingham, AL). Among the selected mAbs, one IgM anti-DeNAc mAb, designated DA2, was used in all of the binding and functional studies described below. This monoclonal antibody was purified from tissue culture by ammonium sulfate precipitation and size exclusion chromatography (TOYOPEARL® HW-55F, Sigma-Aldrich) in buffer containing 2 mM arginine, 0.002% TWEEN® 20, 24 mM sucrose, pH 7 (all from Sigma-Aldrich). The IgM-containing fractions were combined, sterile filtered, lyophilized, and stored at −80° C. until used. The lyophilized mAb was resuspended in $1/10^{th}$ the original volume of sterile water for use in the experiments described below in Example 23. The DA2 mAB was found to be highly specific for any non-reducing end neuraminic acid residue, regardless of the adjacent residue or glycosidic linkage (data not shown).

Example 22

Cloning and Sequencing of Nucleic Acid Encoding the DA2 mAB

To investigate the molecular basis for antigen recognition, the variable region (V) gene of the DA2 murine mAb was cloned and sequenced as follows.

The variable region gene of the immunoglobulin heavy and light chains from a DA2-expressing mouse hybridoma cell line was amplified by PCR using degenerate primers and cloned using the TOPO TA Cloning® Kit (Invitrogen, Carlsbad, Calif.)ˉ (Invitrogen,) as described by Wang et al. (2000) J Immunol Methods 233, 167-77 using E. coli strain XL-2 Blue as a host. Plasmid DNA from individual transformants selected on LB-ampicillin plates was isolated using the Qiagen Mini Prep Kit (Qiagen) according to the manufacturer's instructions. The cloned V gene from three clones was sequenced by Davis Sequencing (Davis, Calif.).

The mAb nucleotide sequence of DA2 was analyzed using IGMT/V-QUEST and the mouse immunoglobulin nucleotide sequence data-base through the online web facilities of the international ImMunoGeneTics® information system (IMGT, on the internet at imgt.cines.fr) that was initiated and coordinated by Marie-Paule Lefranc (Université Montpellier II, CNRS, LIGM, IGH, IFR3, Montpellier, France).

The nucleic acid and amino acid sequences of the variable regions of the DA2 heavy chain polypeptide and light chain polypeptide are provided in FIGS. 19 and 20 with the framework (denoted by, e.g., FR1—IMTG) and CDR regions indicated as defined by the International Immunogenetics Information System (IMGT) definitions (Lefranc et al. IMGT, the international ImMunoGeneTics information System®. Nucl. Acids Res., 2005, 33, D593-D597).

Example 23

Effect of mAb DA2 on the Viability of Human Melanoma Cell Line SK-MEL 28

To determine the effect of DA2 (1, 0.5, and 0.25 µg/ml) and an irrelevant IgM (Southern Biotech) control mAb (5 µg/ml) on cell viability, the mAbs were incubated in centuplicate with SK-MEL 28 cells for 48 hrs. The cells were then analyzed by flow cytometry. Cell viability was determined using ViaCount Reagent (Guava Technologies), as per manufacturer's instructions. Briefly, cells were cleaved from the tissue culture plate, collected by centrifugation and resuspended in ViaCount Reagent. Cell viability was analyzed using a program on the Guava EasyCyte flow cytometer that had preset gates for live, apoptotic, and dead cells. DA2 was found to reduce the number of viable cells, and increases the number of apoptotic and dead cells compared to the irrelevant control mAb at all concentrations tested (FIG. 21). In data not shown, DA2 can inhibit the growth Neisseria meningtidis strains from serogroups A, B, C, X, Y, and W135.

Thus, SEAM 3 and DA2 which have different fine antigenic specificities but recognize in common PS antigens containing Neu at the non-reducing end both have functional activity against Neisseria meningitidis and cancer cells that express Neu-containing sialic acid antigensetc.]

It was also found that OS derivatives made from PSA alpha (2→9) capsular material of N. meningitidis serogroup C contain the immunodominant Neu-epitope recognized by the DA2 monoclonal antibody. As such, the data indicate that a new class of OS alpha (2→9) derivative vaccines (including mixtures of alpha (2→8) and (2→9) glycosidic linkages) can be applied in a similar manner as described for OS alpha (2→8) derivatives.

The above results demonstrate that the shortest oligosialic acid or oligosaccharide (OS) contained a mixture of degree of polymerization (Dp) of 2 to 6, but mostly 4 to 6, and that a tetramer exhibits all of the activity of the much longer derivatives. The results also demonstrate that a vaccine composed of OS derivative with these features is highly immunogenic and elicits an antigen-specific antibody response that (i) activates protective mechanisms present in human blood (complement mediated bacteriolysis and/or opsonophagocytosis) that decreases viability of the bacteria in human blood, and (ii) is reactive with neuraminic acid-containing antigens expressed by cancer cells.

In addition, methods have been described for producing and characterizing defined PS-TT vaccines including DeNAc-TT, NPrSia-TT, TcAc-TT and OS-TT. Extensive characterization of antisera against the PS-TT vaccines further supports the finding that the smallest OS vaccine derivatives bearing a non-reducing end de-N-acetyl sialic acid residue contains the minimal features necessary for effective vaccine activity. Surprisingly, while the TcAc-TT vaccine elicited very low titers against the homologous antigen, antisera against TcAc-TT exhibited a broad spectrum of activity against both Neisseria meningitidis serogroups and cancer cells. Moreover, it was found that the NPrSia-TT, TcAc-TT and OS-TT conjugate vaccines as well as the unconjugated antigens having a degree of polymerization (dp) of about 2-20, particularly a dp of about 2-10 or less, exhibited an IC50 of less than about 0.1 µg/ml for inhibiting binding SEAM 2 (TcAc) or SEAM 3 (NPrSia-TT and OS-TT) to NPr or dodecylamine-NPr, further illustrating that the OS vaccine derivatives bearing a non-reducing end de-N-acetyl sialic acid residue contains the minimal features necessary for effective vaccine activity.

It was also found that in addition to OS derivatives produced from PSA alpha (2→8) precursor material (such as obtainable from N. meningitidis serogroup B or E. Coli K1), OS derivatives derivable from PSA alpha (2→9) material (such as from N. meningitidis serogroup C) exhibit similar properties, supporting a new class of PS-TT vaccines comprising alpha (2→9), or a mixture of alpha (2→8) and alpha (2→9), glycosidic linkages. For example, capsular polysaccharide isolated from E. coli K92 strains (Devi et al. Proc. Natl. Acad. Sci. USA, 1991, 88:7175). PS vaccines containing alpha (2→9) glycosidic linkages can have particular advantages for application against N. meningitidis serogroup C.

The results also demonstrate that while the PS-TT vaccines have a range of different activities, the non-reducing end de-N-acetyl neuraminic acid residue component present in the OS derivatives (i) is found in all of the PS-TT antigens, (ii) is immunogenic and the immunodominant determinant of the PS-TT vaccines, and (iii) PS-TT antisera for all vaccines were able to activate complement factor deposition on the cell surface of Neisseria meningitidis groups B, C, X, Y, and W135, which is a known correlate of protection against disease caused by these bacteria. Moreover, all of the PS-TT antisera were able to activate complement protein deposition on different cancer cells, and it was demonstrated that reactive antigens were expressed in only or at higher levels in several primary human tumors but not in normal human tissues. Lastly, a non-reducing end Neu-specific monoclonal antibody DA2 was isolated, sequenced, propagated, and found to bind with higher affinity to the immunodominant epitope than any of the SEAM antibodies, as well as reduce the number of viable cancer cells, and increases the number of apoptotic and dead cells compared to the irrelevant control mAb at all concentrations tested.

It is evident from the above results and discussion that OS derivatives and vaccines can be produced to exhibit protective effects against disease caused by N. meningitidis, particularly serogroups B and C. It also is evident that the OS derivatives and antibodies generated thereto, including DA2, are applicable for detecting a cancerous cell in a subject, inhibiting growth of a cancerous cell in a subject, eliciting antibodies in a subject, eliciting antibodies to a cancerous cell, and the like. As such, the compositions and methods disclosed herein find use in a variety of different applications and represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of eliciting antibodies in a mammalian subject, wherein the antibodies specifically bind to bacteria comprising a de-N-acetylated sialic acid (deNAc SA) epitope, the method comprising:

administering to the subject an immunogenically effective dose of an immunogenic composition comprising an isolated partially de-N-acetylated alpha (2→8) or (2→9) oligosialic acid derivative having a degree of polymerization ranging from 2 to 20, a reducing end and non-reducing end, and having de-N-acetyl sialic acid residues selectively at the non-reducing end such that the alpha (2→8) or (2→9) oligosialic acid derivative is enriched for de-N-acetylated sialic acid residues at its non-reducing end and is resistant to degradation by exoneuraminidase, wherein said alpha (2→8) or (2→9) oligosialic acid derivative is conjugated to a carrier protein and said administering is effective to elicit production of said antibodies that specifically bind to a deNAc SA epitope of said bacteria, and wherein the alpha (2→8) or (2→9) oligosialic acid derivative of the conjugate is prepared by treating an alpha (2→8) or (2→9) oligosialic acid precursor having a reducing end and a non-reducing end and containing N-acetyl sialic acid residues with sodium borohydride under conditions suitable to produce the partially de-N-acetylated alpha (2→8) or (2→9) oligosialic acid derivative.

2. The method of claim 1, wherein the bacteria are *Neisseria meningitides* group B, *Neisseria meningitides* group C, or *Escherichia coli* K1.

3. The method of claim 1, wherein said non-reducing end of said oligosialic acid derivative is a de-N-acetylated neuraminic acid residue.

4. The method of claim 1, wherein said oligosialic acid derivative comprises one or more N-acyl groups other than N-acetyl residues.

5. The method of claim 1, wherein said oligosialic acid derivative has a degree of polymerization ranging from 2 to 10.

6. The method of claim 1, wherein the sodium borohydride is in an aqueous solution at a pH ranging from 8 to 11.

7. The method of claim 6, wherein the treatment with the sodium borohydride is carried out at ambient temperature.

8. A method of eliciting antibodies in a mammalian subject, wherein the antibodies specifically bind to bacteria comprising a de-N-acetylated sialic acid (deNAc SA) epitope, the method comprising:

administering to the subject an immunogenically effective dose of an immunogenic composition comprising an isolated partially de-N-acetylated alpha (2→8) or (2→9) oligosialic acid derivative having a degree of polymerization ranging from 2 to 20, a reducing end and non-reducing end, and having de-N-acetyl sialic acid residues selectively at the non-reducing end so that the alpha (2→8) or (2→9) oligosialic acid derivative is enriched for de-N-acetylated sialic acid residues at its non-reducing end and is resistant to degradation by exoneuraminidase, wherein said alpha (2→8) or (2→9) oligosialic acid derivative is conjugated to a carrier protein and said administering is effective to elicit production of said antibodies that specifically bind to a deNAc SA epitope of said bacteria, and wherein preparation of the alpha (2→8) or (2→9) oligosialic acid derivative of the conjugate comprises treating an alpha (2→8) or (2→9) oligosialic acid precursor having a reducing end and a non-reducing end and containing N-acetyl sialic acid residues or a partially de-N-acetylated alpha (2→8) or (2→9) oligosialic acid under non-oxidizing acid hydrolysis conditions suitable to produce the partially de-N-acetylated alpha (2→8) or (2→9) oligosialic acid derivative.

9. The method of claim 8, wherein the treating under the non-oxidizing acid hydrolysis conditions is performed in an acidic buffer at a temperature of 25° C. to 90° C. for 1 to 30 hours.

10. The method of claim 8, wherein the bacteria are *Neisseria meningitidis* group B, *Neisseria meningitidis* group C, or *Escherichia coli* K1.

11. The method of claim 8, wherein said non-reducing end of said oligosialic acid derivative is a de-N-acetylated neuraminic acid residue.

12. The method of claim 8, wherein said oligosialic acid derivative comprises one or more N-acyl groups other than N-acetyl residues.

13. The method of claim 8, wherein said oligosialic acid derivative has a degree of polymerization ranging from 2 to 10.

14. The method of claim 1, wherein the carrier protein is an immunomodulator.

15. The method of claim 14, wherein the immunomodulator is a tetanus toxoid.

16. The method of claim 8, wherein the carrier protein is an immunomodulator.

17. The method of claim 16, wherein the immunomodulator is a tetanus toxoid.

* * * * *

SEQUENCE LISTING

```
<160> NUMBER OF SEQ ID NOS: 4

<210> SEQ ID NO 1
<211> LENGTH: 336
<212> TYPE: DNA
<213> ORGANISM: mus musculus
<220> FEATURE:
<221> NAME/KEY: CDS
<222> LOCATION: (0)...(0)

<400> SEQUENCE: 1
gaggtgaagc tggaacagac tcgacctgaa ctggggaagc ctggggcttt gatgacgata      60
tcctgcaagg tttctggtta ctctttcact ggctactaca tgagctgagt gaagcaaagt     120
cctgaaaata gccttgagtg gattggagag attaatccta gcactggtgg tagtacctac     180
aaccagaagt tcaaggccaa ggccacattg actgtagaca aatcctccag cacagcctac     240
atgcagctca agagcctgac atctgaggac tctgcagtct attactgtgc aagaagggga     300
ttctcctatg ctatggacta ctggggtcaa ggaacc                              336

<210> SEQ ID NO 2
```

```
<211> LENGTH: 111
<212> TYPE: PRT
<213> ORGANISM: mus musculus

<400> SEQUENCE: 2

Glu Val Lys Leu Glu Gln Thr Arg Pro Glu Leu Gly Lys Pro Gly Ala
1               5                   10                  15

Leu Met Thr Ile Ser Cys Lys Val Ser Gly Tyr Ser Phe Thr Gly Tyr
            20                  25                  30

Tyr Met Ser Val Lys Gln Ser Pro Glu Asn Ser Leu Glu Trp Ile Gly
        35                  40                  45

Glu Ile Asn Pro Ser Thr Gly Gly Ser Thr Tyr Asn Gln Lys Phe Lys
50                  55                  60

Ala Lys Ala Thr Leu Thr Val Asp Lys Ser Ser Ser Thr Ala Tyr Met
65                  70                  75                  80

Gln Leu Lys Ser Leu Thr Ser Glu Asp Ser Ala Val Tyr Tyr Cys Ala
                85                  90                  95

Arg Arg Gly Phe Ser Tyr Ala Met Asp Tyr Trp Gly Gln Gly Thr
            100                 105                 110

<210> SEQ ID NO 3
<211> LENGTH: 324
<212> TYPE: DNA
<213> ORGANISM: mus musculus
<220> FEATURE:
<221> NAME/KEY: CDS
<222> LOCATION: (0)...(0)

<400> SEQUENCE: 3
gacattgtga tgacacagac tacagcttct ttggctgtgt ctctagggca gagagccacc      60
atctcctgca gagccagtga aagtgttgaa tattatggca caagtttaat gcagtggtac     120
caacagaaac caggacagcc acccaaactc ctcatctatg ctgcatccaa cgtagaatct     180
ggggtccctg ccaggtttag tggcagtggg tctgggacag acttcagcct caacatccat     240
cctgtggagg aggatgatat tgcaatgtat ttctgtcagc aaagtaggaa ggttccttac     300
acgttcggag gggggaccaa gctg                                             324

<210> SEQ ID NO 4
<211> LENGTH: 108
<212> TYPE: PRT
<213> ORGANISM: mus musculus

<400> SEQUENCE: 4

Asp Ile Val Met Thr Gln Thr Thr Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Tyr Thr Phe Gly Gly Gly Thr Lys Leu
            100                 105
```